US008895752B2

(12) United States Patent
Rossignol et al.

(10) Patent No.: US 8,895,752 B2
(45) Date of Patent: Nov. 25, 2014

(54) ALKYLSULFONYL-SUBSTITUTED THIAZOLIDE COMPOUNDS

(75) Inventors: Jean-Francois Rossignol, St. Petersburg, FL (US); J. Edward Semple, Tampa, DE (US)

(73) Assignee: Romark Laboratories L.C., Tampa, FL (US)

( * ) Notice: Subject to any disclaimer, the term of this patent is extended or adjusted under 35 U.S.C. 154(b) by 0 days.

(21) Appl. No.: 13/353,686

(22) Filed: Jan. 19, 2012

(65) Prior Publication Data

US 2012/0122939 A1    May 17, 2012

Related U.S. Application Data

(63) Continuation of application No. 12/184,760, filed on Aug. 1, 2008, now Pat. No. 8,124,632.

(60) Provisional application No. 60/953,758, filed on Aug. 3, 2007, provisional application No. 61/046,956, filed on Apr. 22, 2008, provisional application No. 61/056,369, filed on May 27, 2008.

(51) Int. Cl.
| | |
|---|---|
| *C07D 277/00* | (2006.01) |
| *A61K 31/425* | (2006.01) |
| *C07D 417/12* | (2006.01) |
| *C07D 277/46* | (2006.01) |

(52) U.S. Cl.
CPC ............ *C07D 277/46* (2013.01); *C07D 417/12* (2013.01)
USPC .......................................... 548/184; 514/369

(58) Field of Classification Search
CPC ...... C07D 277/54; C07D 277/46; A61K 31/426
USPC .......................................... 548/184; 514/369
See application file for complete search history.

(56) References Cited

U.S. PATENT DOCUMENTS

| | | | |
|---|---|---|---|
| 3,950,351 A | 4/1976 | Rossignol et al. |
| 4,337,081 A | 6/1982 | Gay |
| 4,343,945 A | 8/1982 | Gay |
| 4,416,683 A | 11/1983 | Burow, Jr. |
| 5,169,846 A | 12/1992 | Crooks |
| 5,578,621 A | 11/1996 | Rossignol |
| 6,020,353 A | 2/2000 | Rossignol |
| 6,136,835 A | 10/2000 | Camden |
| 6,849,254 B1 | 2/2005 | Brass et al. |
| 7,241,781 B2 | 7/2007 | Barrish et al. |

(Continued)

FOREIGN PATENT DOCUMENTS

| | | |
|---|---|---|
| CA | 2618646 A1 | 11/2007 |
| EP | 0 343 894 B1 | 6/1992 |

(Continued)

OTHER PUBLICATIONS

Database Registry [Online] Chemical Abstracts Service, Columbus, Ohio, US, 2000, XP002684230, retrieved from STN accession No. 304864-25-3, compounds 304864-25-3.

(Continued)

*Primary Examiner* — Shengjun Wang
(74) *Attorney, Agent, or Firm* — Foley & Lardner LLP

(57) ABSTRACT

A new class of alkylsulfonyl-substituted thiazolide compounds is described. These compounds show strong activity against hepatitis virus.

20 Claims, 3 Drawing Sheets

(56) References Cited

U.S. PATENT DOCUMENTS

| | | | |
|---|---|---|---|
| 8,541,457 B2 | 9/2013 | Fu et al. | |
| 2004/0082629 A1 | 4/2004 | Iwataki et al. | |
| 2004/0192746 A1 | 9/2004 | Sanner et al. | |
| 2004/0242518 A1 | 12/2004 | Chen et al. | |
| 2005/0090506 A1* | 4/2005 | Iwataki et al. | 514/256 |
| 2005/0112751 A1 | 5/2005 | Fang et al. | |
| 2006/0167053 A1 | 7/2006 | Iino et al. | |
| 2006/0194853 A1 | 8/2006 | Rossignol | |
| 2007/0004661 A1 | 1/2007 | Stein et al. | |
| 2007/0110685 A1 | 5/2007 | Auspitz et al. | |
| 2008/0097106 A1 | 4/2008 | Rossignol | |
| 2009/0176991 A1 | 7/2009 | Murray et al. | |
| 2010/0009970 A1 | 1/2010 | Johansen et al. | |
| 2010/0075964 A1 | 3/2010 | Busch et al. | |
| 2010/0081713 A1 | 4/2010 | Sharma et al. | |
| 2010/0331295 A1 | 12/2010 | Busch et al. | |

FOREIGN PATENT DOCUMENTS

| | | |
|---|---|---|
| GB | 2331748 A | 6/1999 |
| JP | S27-122 | 1/1952 |
| JP | 56-158703 A | 12/1981 |
| JP | 61-009978 A | 1/1989 |
| JP | 02-017177 A | 1/1990 |
| JP | 2003-335680 A | 11/2003 |
| SU | 910628 B | 3/1982 |
| WO | WO 95/28393 A1 | 10/1995 |
| WO | WO 00/02851 A1 | 1/2000 |
| WO | WO 00/26202 A2 | 5/2000 |
| WO | WO 02/092584 A1 | 11/2002 |
| WO | WO 03/015774 * | 2/2003 |
| WO | WO 2006/042195 A1 | 4/2006 |
| WO | WO 2006/122011 A2 | 11/2006 |
| WO | WO 2007/002559 A1 | 1/2007 |
| WO | WO 2007/008541 A2 | 1/2007 |
| WO | WO 2007/016228 A2 | 2/2007 |
| WO | WO 2007/076034 A2 | 7/2007 |
| WO | WO 2007/125103 A2 | 11/2007 |
| WO | WO 2010/107736 A2 | 9/2010 |
| WS | WO 03/103648 A1 | 12/2003 |

OTHER PUBLICATIONS

Korba et al., "Potential for Hepatitis C Virus Resistance to Nitazoxanide or Tizoxanide," Antimicrobial Agents and Chemotherapy, Nov. 2008, 52(11):4069-4071.
Rossignol et al., "Thiazolides, a New Class of Anti-influenza Molecules Targeting Viral Hemagglutinin at the Post-translation Level," J. Biol. Chem., Oct. 23, 2009, 284(43):29798-29808.
U.S. Appl. No. 12/777,383, filed May 11, 2010, Rossignol et al.
U.S. Appl. No. 12/821,571, filed Jun. 23, 2010, Rossignol et al.
Allen et al., "Identification and Characterization of Mutations in Hepatitis B Virus Resistant to Lamivudine," Hepatology, 1998, 27(6):1670-1677.
Amadi et al., "Effect of nitazoxanide on morbidity and mortality in Zambian children with cryptosporidiosis: a randomized controlled trial," The Lancet, Nov. 2, 2002, 360:1375-1380.
Angus et al., "Resistance fo Adefovir Dipivoxil Therapy Associated With the Selection of a Novel Mutation in the HBV Polymerase," Gastoenterology, 2003, 125:292-297.
Belen'kii et al., "Multiple drug effect analysis with confidence interval," Antiviral Research, 1994, 25:1-11.
Blight et al., "Efficient Initiation of HCV RNA Replication in Cell Culture," Science, Dec. 8, 2000, 290:1972-1974.
Blight et al., "Efficient Replication of Hepatitis C Virus Genotype 1a RNAs in Cell Culture," Journal of Virology, Mar. 2003, 77(5):3181-3190.
Broekhuysen et al,. "Nitazoxanide: pharmacokinetics and metabolism in man," International Journal of Clinical Pharmacology and Therapeutics, 2000, 38(8):387-394.
Chen et al., "The Natural History of Hepatitis C Virus (HCV) Infection," Int. J. Med. Sci., 2006, 3:47-52.

Database Caplus [Online] Chemical Abstract Service, XP002498889, Database Accession No. 2000:53572 abstract of WO 00/02851, 3 pages.
Database Caplus [Online] Chemical Abstract Service, XP002498890, Database Accession No. 2003:918699, abstract of JP2003 335680 A, 1 page.
Database Caplus [Online] Chemical Abstract Service, XP002498891, Database Accession No. 1964:468902, 1 page abstract of Bellone et al., "New substituted acetophenones and their derivatives," Annali di Chimica, Societa Chimia Italiana, Rome, Italy, vol. 5, No. 54, Jan. 1, 1964, 510-519.
Database Caplus [Online] Chemical Abstract Service, XP002498892, Database Accession No. 2000:53572 abstract of WO 00/26202, 3 pages.
Fox et al., "Nitazoxanide: A New Thiazolide Antiparasitic Agent," Review of Anti-Infective Agents, Apr. 15, 2005, 40:1173-1180.
Hoffman et al., "Antiparasitic Drug Nitazoxanide Inhibits the Pyruvate Oxidoreductases of *Helicobacter pylori*, Selected Anaerobic Bacteraial and Parasites, and *Campylobacter jejuni*," Antimicrobial Agents and Chemotherapy, Mar. 2007, 51(3):868-876.
International Search Report and Written Opinion mailed Aug. 23, 2010, in PCT/US2010/039638, 11 pages.
International Search Report and Written Opinion mailed Jul. 9, 2010, in PCT/US2010/034319, 10 pages.
Iyer et al., "Phosphorothioate Di- and Trinucleotides as a Novel Class of Anti-Hepatitis B Virus Agents," Antimicrobial Agents and Chemotherapy, Jun. 2004, 48(6):2199-2205.
Kabanov, Alexander V., "Polymer Genomics: An Insight into Pharmacology and Toxicology of Nanomedicines," Adv. Drug Deliv. Rev., Dec. 30, 2006, 58(15):1597-1621.
Korba et al., "Antisense oligonucleotides are effective inhibitors of hepatitis B virus replication in vitro," Antiviral Research, 1995, 28:225-242.
Korba et al., "Nitazoxanide, tizoxanide and other thiazoles are potent inhibitors of hepatitis B virus and hepatitis C virus replication," Antiviral Research, 2008, 77:56-63.
Korba et al., "Use of a standardized cell culture assay to assess activities of nucleoside analogs against hepatitis B virus replication," Antiviral Research, 1992, 19:55-70.
Lavanchy, D., "Hepatitis B virus epidemiology, disease burden, treatment, and current and emerging prevention and control measures," Journal of Viral Hepatitis, 2004, 11:97-107.
Locarnini, Stephen M.D., Ph.D., "Molecular Virology of Hepatitis B Virus," Seminars in Liver Disease, 2004, 24(Suppl. 1):3-10.
Musher et al., "Nitazoxanide for the Treatment of *Clostridium difficile* Colitis," CID, Aug. 15, 2006, 43:421-427.
Okuse et al., "Enhancement of antiviral activity against hepatitis C virus in vitro by interferon combination therapy," Antiviral Research, 2005, 65:23-34.
Ortiz et al., "Randomized clinical study of nitazoxanide compared to metronidazole in the treatment of symptomatic giardiasis in children from Northern Peru," Ailment Pharmacol. Ther., 2001, 15:1409-1415.
Pankuch et al., "Activities of Tizoxanide and Nitazoxanide Compared to Those of Five Other Thiazoles and Three Other Agents against Anaerobic Species," Antimicrobial Agents and Chemotherapy, Mar. 2006, 50(3):1112-1117.
Poland et al., "Influenza Virus Resistance to Antiviral Agents: A Plea for Rational Use," CID, May 1, 2009, 48:1254-1256.
Rao et al., "Design, Synthesis, and Biological Evaluation of 6-Substituted-3-(4-methanesulfonylphenyl)-4-phenylpyran-2-ones: A Novel Class of Diarylheterocyclic Selective Cyclooxygenase-2 Inhibitors," J. Med. Chem., 2003, 46:4872-4882.
Rossignol et al., "Effect of nitazoxanide for treatment of severe rotavirus diarrhea: randomized double-blind placebo-controlled trial," The Lancet, Jun. 13, 2006 online, 1-6.
Rossignol et al., "Effect of Nitazoxanide in Diarrhea and Enteritis Caused by *Cryptosporidium* Species," Clinical Gastroenterology and Hepatology, 2006, 4:320-324.
Rossignol at al., "Effect of Nitazoxanide in Persistent Diarrhea and Enteritis Associated with *Blastocystis hominis*," Clinical Gastroenterology and Hepatology, 2005, 3:987-991.

(56) References Cited

OTHER PUBLICATIONS

Rossignol et al., "Nitazoxanide in the treatment of viral gastroenteritis: a randomized double-blind placebo-controlled clinical trial," Aliment. Pharacol. Ther., 2006, 24:1423-1430.

Rossignol et al., "Treatment of Diarrhea Caused by *Giardia intestinalis* and *Entamoeba histolytica* or *E. dispar*: A Randomized, Double-Blind, Placebo-Controlled Study of Nitazoxanide," J. Infect. Diseases, 2001, 184:381-384.

Schiavi et al., "Preparation of *N-Tert*-butoxycarbonylthiourea opens the way to protected 2- aminothiazoles," Synthetic Communications, 2002, 32(11):1671-1674.

Sells et al., "Replicative Intermediates of Hepatitis B Virus in HepG2 Cells That Produce Infectious Virions," J. Virol., Aug. 1988, 62(8):2836-2844.

Stockis et al., "Nitazoxanide pharmacokinetics and tolerability in man during 7 days of 0.5 g and 1 g b.i.d. dosing," International Journal of Clinical Pharmacology and Therapeutics, 2002, 40(5):221-227.

Tellinghuisen et al., "Structure of the zinc-binding domain of an essential component of the hepatitis C virus replicase," Nature Letters, 2005, 435:374-379.

Tomei et al., "HCV antiviral resistance: the impact of in vitro studies on the development of antiviral agents targeting the viral NS5B polymerase," Antiviral Chemistry & Chemotherapy, 2005, 16:225-245.

Tong et al., "Identification and analysis of fitness of resistance mutations against the HCV protease inhibitor SCH 503034," Antiviral Research, 2006, 70:26-38.

Wong et al., "Update of viral hepatitis: 2005," Current Opinion in Gastroenterology, 2006, 22:241-247.

Yim et al., "Evolution of Multi-Drug Resistant Hepatitis B Virus During Sequential Therapy," Hepatology, Sep. 2006, 44(3):703-712.

Lipunova et al., "Fluorine-Containing Heterocycles: Xii. Fluorine-Containing Quinazolin-4-ones and Azolo[α]quinazolinone Derivatives," Russian Journal of Organic Chemistry, 2005, 41(7):1071-1080.

Masihi et al., "Low dose oral combination chemoprophylaxis with osletamivir and amantadine for influenza A virus infections in mice," J. Chemother., Jun. 2007, 19(3):295-303.

Santoro et al., "Thoazolides: A New Class of Broad-Spectrum Antiviral Drugs Targeting Virus Maturation," Antiviral Research, Program and Abstracts, The Twentieth International Conference on Antiviral Research, 2007, 74:A31 (11).

Boyer et al., "Synthesis and photosynthetic inhibition activity of substituted 5-(bis-trifluoromethyl)methyl)-2-aminothiazoles," Journal of Fluorine Chemistry, 2006, 1522-1527.

Database Registry [Online] Chemical Abstracts Service, Columbus, OH, US; 2000, XP002685340, retrieved from STN accession No. 304864-25-3 . https://register.epo.org/espacenet/application?number=EP10775367, one page.

Bellone et al., Annali di Chimica, 1964, V5 N54, 510-519, English summary on first page.

Mueller et al., "In Vitro Effects of Thiazolides on *Giardia lamblia* WB Cline C6 Cultured Axenically and in Coculture with Caco2 Cells," Antimicrobial Agents and Chemotherapy, Jan. 2006, 50(1):162-170.

Ziegler et al., "2-Aminothiazolesulfonamides," J. Org. Chem., 1960, 25:1454-1455.

Burger et al., "Isoterism and bioisoterism in drug design," Progress in Drug Research, Basel, 1991, 287-371.

Patani et al., "B oisoterism: A Rational Approach in Drug Design," Chem. Rev., 1996, 96(8):3147-3176.

\* cited by examiner

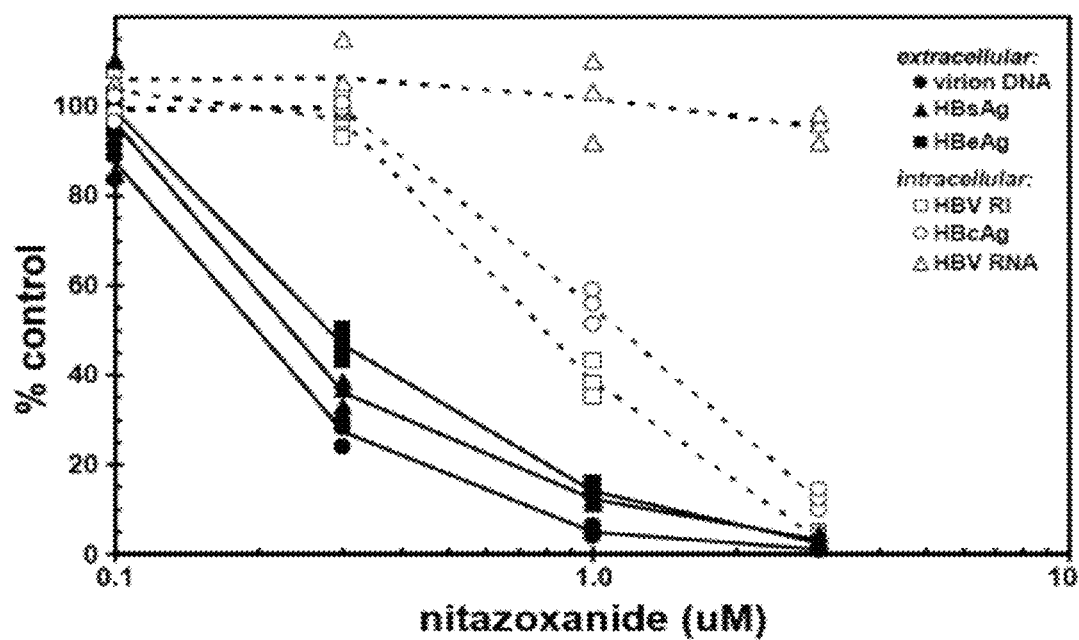

ALKYLSULFONYL-SUBSTITUTED THIAZOLIDE COMPOUNDS

CROSS-REFERENCE TO RELATED APPLICATIONS

This application is a Continuation of U.S. application Ser. No. 12/184,760, filed Aug. 1, 2008, which claims benefit of U.S. Provisional Application No. 60/953,758, filed Aug. 3, 2007, and U.S. Provisional Application No. 61/046,956, filed Apr. 22, 2008, and U.S. Provisional Application No. 61/056,369, filed on May 27, 2008, the entire contents of each of which are incorporated herein by reference.

STATEMENT REGARDING FEDERALLY SPONSORED RESEARCH OR DEVELOPMENT

The invention disclosed herein was made with Government support under NIAID contract NO1-AI-30046 to Georgetown University Medical Center. Accordingly, the U.S. Government may have certain rights in this invention.

BACKGROUND

The present application relates generally to the field of thiazolide compounds. In particular, the application relates to alkylsulfonyl-substituted thiazolide compounds.

Hepatitis B Virus (HBV) and Hepatitis C Virus (HCV) are major public health problems, causing more than an estimated 500 million chronic infections worldwide (Chen and Morgan, 2006; Lavanchy, 2004). Both viruses are a source of significant progressive liver disease, and are the major risk factors for nearly all cases of primary hepatocellular carcinoma (Chen and Morgan, 2006; Lavanchy, 2004; Wong and Lok, 2006). Licensed standards of care for both viral infections, while effective in many cases, are sub-optimal and do not result in virologic or clinical 'cures' in most individuals (Wong and Lok, 2006). The development of drug-resistance in HBV, including strains carrying resistance to multiple licensed agents is an emerging clinical problem, and drug-resistance for future HCV therapies is predicted to be a significant clinical issue (Tomei et al., 2005; Tong et al., Yim et al., 2006).

Thiazolide compounds such as nitazoxanide (NTZ) are anti-infective and possess activity against anaerobic bacteria, protozoa and viruses (Fox et al., 2005; Pankuch and Appelbaum, 2006; Rossignol et al., 2006a; Rossignol and El-Gohary, 2006). Originally developed as a treatment of intestinal protozoan infections, the antiviral properties of NTZ were discovered during the course of its development for treating cryptosporidiosis in patients with acquired immune deficiency syndrome (AIDS). NTZ is marketed in the United States for treating diarrhea and enteritis caused by *Cryptosporidium* spp or *Giardia lamblia* in adults and children down to 12 months of age (Alinia®, Romark Laboratories, Tampa, Fla. USA). Clinical trials have demonstrated effectiveness of NTZ in treating diarrhea and enteritis associated with enteric protozoan infections caused by *Cryptosporidium* spp, *G. lamblia*, *Entamoeba histolytica* and *Blastocystis hominis* (Amadi et al., 2002; Oritz et al., 2001; Rossignol et al., 2001, 2005, 2006b). Recent randomized double-blind clinical trials have demonstrated effectiveness of NTZ in treating *Clostridium difficile* colitis in adults, rotavirus gastroenteritis in young children, and rotavirus and norovirus gastroenteritis in adults (Musher et al, 2006; Rossignol et al, 2006a; Rossignol and El Gohary, 2006). The mechanism of action of NTZ against anaerobic organisms is attributed to interference with pyruvate:ferredoxin oxidoreductase (PFOR) enzyme-dependent electron transfer reactions, which are essential for anaerobic energy metabolism (Hoffman et al., 2006). Its mechanism of antiviral activity has not been fully elucidated.

Following oral administration of a 500 mg tablet, NTZ is partially absorbed from the gastrointestinal tract and rapidly hydrolyzed in plasma to form its active circulating metabolite, tizoxanide (TIZ). NTZ is not detected in plasma. Maximum serum concentrations of TIZ, reach approximately 10 μg/mL (37 μM) (Stockis et al., 2002) following oral administration of one 500 mg NTZ tablet (Alinia®) with food. TIZ is glucurono-conjugated in the liver and excreted in urine and bile. Approximately two-thirds of an oral dose pass through the intestinal tract and is excreted in feces as TIZ (Broekhuysen et al., 2000). The elimination half-life of TIZ from plasma is approximately 1.5 hours. TIZ does not inhibit cytochrome P450 enzymes, and therefore, no drug-drug interactions are expected (Broekhuysen et al., 2000; Stockis et al., 2002). The most commonly reported side-effects in clinical trials include mild abdominal pain, headache, diarrhea and nausea, which occur at rates similar to those reported for patients receiving placebo. While most of the clinical experience with NTZ has involved 3 to 14 days of treatment, continual use of the drug for periods as long as 4 years has been evaluated in patients with AIDS-related cryptosporidiosis without any significant drug-related adverse events (Fox et al., 2005; Rossignol, 2006).

Here, results of studies characterizing the activities of NTZ, TIZ and other new thiazolides are presented. In particular, the antiviral activity of 2-benzamido-5-alkylsulfonyl-thiazoles is demonstrated.

SUMMARY

Disclosed are thiazolide compounds or salts thereof. In some embodiments, the disclosed compounds have a formula (I)

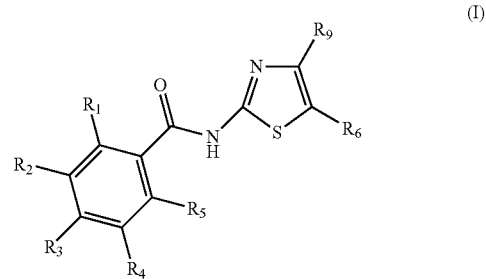

wherein $R_1$ through $R_6$ and $R_9$ are independently chosen from the group consisting of H, CN, $NO_2$, F, Cl, Br, I, —OH, —$PO(OR_a)(OR_b)_{0-1}$, ($C_1$-$C_6$)-alkyl, ($C_2$-$C_6$)-alkenyl, ($C_2$-$C_6$)-alkynyl, ($C_3$-$C_8$)-cycloalkyl, ($C_3$-$C_8$)-cycloalkyl-($C_1$-$C_4$)-alkyl, ($C_3$-$C_8$)-cycloalkyl-($C_2$-$C_4$)-alkenyl, ($C_3$-$C_8$)-cycloalkyl-($C_2$-$C_4$)-alkynyl, ($C_5$-$C_8$)-cycloalkenyl, ($C_5$-$C_8$)-cycloalkenyl-($C_1$-$C_4$)-alkyl, ($C_5$-$C_8$)-cycloalkenyl-($C_2$-$C_4$)-alkenyl, ($C_5$-$C_8$)-cycloalkenyl-($C_2$-$C_4$)-alkynyl, ($C_1$-$C_6$)-alkoxy, ($C_2$-$C_6$)-alkenyloxy, ($C_2$-$C_6$)-alkynyloxy, ($C_2$-$C_6$)-alkoxy-($C_1$-$C_4$)-alkyl, ($C_1$-$C_6$)-alkoxy-($C_1$-$C_4$)-alkyl, ($C_1$-$C_6$)-alkoxy-($C_2$-$C_4$)-alkenyl, ($C_1$-$C_6$)-alkoxy-($C_2$-$C_4$)-alkynyl, ($C_2$-$C_6$)-alkenyloxy, ($C_2$-$C_6$)-alkenyloxy-($C_1$-$C_4$)-alkyl, ($C_2$-$C_6$)-alkenyloxy-($C_2$-$C_4$)-alkenyl, ($C_2$-$C_6$)-alkenyloxy-($C_2$-$C_4$)-alkynyl, ($C_2$-$C_6$)-alkynyloxy, ($C_2$-$C_6$)-alkynyloxy-($C_1$-$C_4$)-alkyl, ($C_2$-$C_6$)-alkynyloxy-($C_2$-$C_4$)-alkenyl, ($C_2$-$C_6$)-alkenyloxy-($C_2$-$C_4$)-alkynyl, ($C_3$-$C_8$)- cycloalkoxy, (C₃-C₈)-cycloalkyl-(C₁-C₄)-alkoxy, (C₃-C₈)-cycloalkyl-(C₂-C₄)-alkenyloxy, (C₃-C₈)-cycloalkyl-(C₂-C₄)-alkynyloxy, (C₅-C₈)-cycloalkenyloxy, (C₅-C₈)-cycloalkenyl-(C₁-C₄)-alkoxy, (C₅-C₈)-cycloalkenyl-(C₂-C₄)-alkenyloxy, (C₅-C₈)-cycloalkenyl-(C₂-C₄)-alkynyloxy, (C₂-C₆)-alkoxy-(C₂-C₆)-alkylamino, (C₁-C₆)-hydroxyalkyl, (C₁-C₆)-acyl, (C₁-C₆)-acyloxy, aroyloxy, arylalkanoyloxy, arylalkenoyloxy, heteroaroyloxy, heteroarylalkanoyloxy, heteroarylalkenoyloxy, (C₁-C₆)-alkylamino, (C₂-C₆)-dialkylamino, (C₂-C₆)-alkylaminoalkyl, amido, (C₁-C₆)-alkylamido, (C₁-C₆)-dialkylamido, (C₁-C₆)-haloalkyl, (C₁-C₆)-perhaloalkyl, (C₁-C₆)-perhaloalkoxy, SR$_e$, (C₁-C₆)-alkylthio, (C₁-C₆)-alkylthioalkyl, (C₁-C₆)-alkylsulfonyl, (C₁-C₆)-alkylsulfonyl-(C₁-C₆)-alkyl, (C₂-C₆)-alkenylsulfonyl, (C₂-C₆)-alkynylsulfonyl, (C₁-C₆)-hydroxyalkylsulfonyl, —SO₂—(CR₇R₈)₀₋₄—COOR$_b$, (C₃-C₈)-cycloalkylsulfonyl, (C₃-C₈)-cycloalkyl-(C₁-C₄)-alkylsulfonyl, (C₃-C₈)-cycloalkyl-(C₂-C₄)-alkenylsulfonyl, (C₃-C₈)-cycloalkyl-(C₂-C₄)-alkynylsulfonyl, (C₅-C₈)-cycloalkenylsulfonyl, (C₅-C₈)-cycloalkenyl-(C₂-C₄)-alkylsulfonyl, (C₅-C₈)-cycloalkenyl-(C₂-C₄)-alkenylsulfonyl, (C₅-C₈)-cycloalkenyl-(C₂-C₄)-alkynylsulfonyl, (C₂-C₆)-alkenylsulfonyl-(C₁-C₆)-alkyl, (C₂-C₆)-alkynylsulfonyl-(C₁-C₆)-alkyl, (C₁-C₆)-hydroxyalkylsulfonyl-(C₁-C₆)-alkyl, (C₃-C₈)-cycloalkylsulfonyl-(C₁-C₆)-alkyl, (C₃-C₈)-cycloalkyl-(C₁-C₄)-alkylsulfonyl-(C₁-C₆)-alkyl, (C₃-C₈)-cycloalkyl-(C₂-C₄)-alkenylsulfonyl-(C₁-C₆)-alkyl, (C₃-C₈)-cycloalkyl-(C₂-C₄)-alkynylsulfonyl-(C₁-C₆)-alkyl, (C₅-C₈)-cycloalkenylsulfonyl-(C₁-C₆)-alkyl, (C₅-C₈)-cycloalkenyl-(C₁-C₄)-alkylsulfonyl-(C₁-C₆)-alkyl, (C₅-C₈)-cycloalkenyl-(C₂-C₄)-alkenylsulfonyl-(C₁-C₆)-alkyl, (C₅-C₈)-cycloalkenyl-(C₂-C₄)-alkynylsulfonyl-(C₁-C₆)-alkyl, arylsulfonyl, arylalkylsulfonyl, arylalkenylsulfonyl, heteroarylsulfonyl, heteroarylalkylsulfonyl, heteroarylalkenylsulfonyl, (C₁-C₆)-alkylsulfonamido, N,N'—(C₁-C₆)-dialkylsulfonamido, (C₁-C₆)-sulfonamidoalkyl, sulfonamidoaryl, sulfonamidoarylalkyl, sulfonamidoarylalkenyl, sulfonamidoarylalkynyl, aryl (such as phenyl), arylalkyl, aryloxy, arylalkoxy, arylthio, arylalkylthio, arylamino, arylalkylamino, arylalkenyl, arylalkynyl, heteroaryl, heteroarylalkyl, heteroarylalkenyl, heteroarylalkynyl, heteroarylalkoxy, heteroarylalkamino, heteroarylalkylthio, heteroaryloxy, heteroarylalkoxy, heterorylthio, heteroarylalkylthio, heteroarylamino, heteroarylalkylamino, lower cycloalkyl, lower cycloalkylalkyl (see above expanded scope), heterocyclo-(C₁-C₄)-alkyl, heterocyclo-(C₂-C₄)-alkenyl, (C₄-C₈)-heterocyclo-(C₂-C₄)-alkynyl, (C₄-C₈)-heterocyclo-(C₁-C₄)-alkoxy, (C₄-C₈)-heterocyclo-C₂-C₄)-alkenyloxy, (C₄-C₈)-heterocyclo-(C₂-C₄)-alkynyloxy, —(CR₇R₈)₀₋₄—OR$_a$, —(CR₇R₈)₀₋₄—COOR$_b$, (CR₇R₈)₀₋₄—CONR$_a$R$_b$, —NH—(CR₇R₈)₀₋₄—CO—R$_c$, —(CR₇R₈)₀₋₄O—CO—R$_d$, and —(CR₇R₈)₀₋₄-L₂-SO₂-L₁-R$_x$, any of which may be optionally substituted;

provided at least one of R₁-R₆ or R₉ must be an —(CR₇R₈)₀₋₄-L₂-SO₂-L₁-R$_x$;

wherein R₇ and R₈ are independently selected from the group consisting of hydrogen, (C₁-C₆)-alkyl, (C₂-C₆)-alkenyl, (C₂-C₆)-alkynyl, (C₁-C₆)-alkoxy, (C₁-C₆)-alkoxy-(C₁-C₆)-alkyl, (C₁-C₆)-hydroxyalkyl, aryl, arylalkyl, arylalkenyl, arylalkynyl, heteroaryl, heteroarylalkyl, heteroarylalkenyl, lower cycloalkyl, lower cycloalkylalkyl, and heterocloalkyl, any of which may be optionally substituted;

or R₇ and R₈, together with the atoms to which they are attached, may be joined to form an optionally substituted 4- to 8-membered heterocycloalkyl or an optionally substituted 3- to 8-membered cycloalkyl ring, any of which may be optionally substituted;

wherein R$_a$ through R$_e$, each independently of one another, is chosen from H, (C₁-C₆)-alkyl, (C₂-C₆)-alkenyl, (C₂-C₆)-alkynyl, (C₃-C₈)-cycloalkyl, (C₃-C₈)-cycloalkyl-(C₁-C₄)-alkyl, (C₄-C₈)-hetero cyclo alkyl, (C₄-C₈)-heterocycloalkyl-(C₁-C₄)-alkyl, aryl, arylalkyl, (CH₂)₀₋₂-phenyl, heteroaryl, heteroarylalkyl, (C₁-C₆)-alkoxy, (C₂-C₆)-alkenyloxy, (C₂-C₆)-alkynyloxy, (C₃-C₈)-cycloalkoxy, (C₃-C₈)-cycloalkyl-(C₁-C₄)-alkoxy, (C₄-C₈)-heterocycloalkoxy, (C₄-C₈)-heterocycloalkyl-(C₁-C₄)-alkoxy, aryloxy, arylalkoxy, heteroaryloxy, heteroarylalkoxy, (C₁-C₆)-alkylamino, (C₂-C₆)-dialkylamino, (C₂-C₆)-alkylaminoalkyl, (C₃-C₈)-cycloalkylamino, (C₃-C₈)-cycloalkyl-(C₁-C₄)-alkylamino, (C₄-C₈)-heterocycloalkylamino, (C₄-C₈)-heterocycloalkyl-(C₁-C₄)-alkylamino, arylamino, arylalkylamino, heteroarylamino, heteroarylalkylamino, and (C₂-C₆)-alkenylamino, any of which may be optionally substituted;

wherein L₁ and L₂ are independently selected from the consisting of a bond, O, —N(R$_y$)—, (C₁-C₆)-alkyl, (C₂-C₆)-alkenyl, (C₂-C₆)-alkynyl, aryl, heteroaryl, arylalkyl, arylalkenyl, arylalkynyl, heteroarylalkyl, heteroarylalkenyl, heteroarylalkynyl, each of which may be optionally substituted with 1 to 3 substituents, provided that L₁ and L₂ are not simultaneously O;

wherein R$_x$ and R$_y$ are independently selected from the group consisting of H, (C₁-C₆)-alkyl, (C₂-C₆)-alkenyl, (C₂-C₆)-alkynyl, (C₃-C₈)-cycloalkyl, (C₃-C₈)-cycloalkyl-(C₁-C₄)-alkyl, (C₄-C₈)-heterocycloalkyl, and (C₄-C₈)-heterocycloalkyl-(C₁-C₄)-alkyl, aryl, heteroaryl, arylalkyl, arylalkenyl, arylalkynyl, heteroarylalkyl, heteroarylalkenyl, heteroarylalkynyl, each of which may be optionally substituted with 1 to 3 substituents;

wherein any of the preceding carbon-containing Rx and Ry may have from zero to nine H atoms replaced by F, Cl, Br, and/or I.

In some embodiments, R₁, R₂, R₃, R₄, or R₅ is one or more —OS(O₂)Rx, wherein Rx is defined as above. In some embodiments, R₁, R₂, R₃, R₄, or R₅ is one or more —OSO₂—CH₃.

In some embodiments, R₆ and R₉ are H or —SO₂-alkyl, preferably —SO₂CH₃.

In one embodiment, the compound has the following formula:

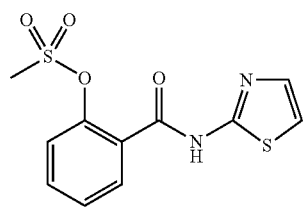 [SMILES: CS(=O)(=O)Oc1ccccc1C(=O)Nc1nccs1]

Also disclosed are pharmaceutical compositions comprising the compounds and a carrier (e.g., a diluent or excipient). The pharmaceutical composition may comprise an effective amount of the compound for treating HCV infection.

Also disclosed are methods for treating HCV infection comprising administering the disclosed pharmaceutical compositions to a patient in need thereof. For example, the patient may have a chronic HCV infection.

BRIEF DESCRIPTION OF THE DRAWINGS

FIG. 3 illustrates the effect of NTZ on HBV nucleic acid and protein levels in 2.2.15 cells. Cultures of 2.2.15 cells were treated under standard procedures (Korba and Gerin, 1992, Antiviral Res. 19:55). HBV nucleic acids levels were determined by quantitative blot hybridization analysis (Korba and Gerin, 1992, Antiviral Res. 19:55; 1995, 28:225). HBV proteins levels were determined by semi-quantitative EIA (Korba and Gerin, 1992, Antiviral Res. 19:55; 1995, 28:225). Samples were diluted (2 to 10-fold) to bring levels into the dynamic response ranges of the EIA's. HBV virion DNA, HBsAg, and HBeAg were analyzed from culture medium samples. HBV RNA, HBV RI (HBV DNA replication intermediates), and HBcAg were analyzed from intracellular lysates.

DETAILED DESCRIPTION OF THE PREFERRED EMBODIMENTS

Figure 1:
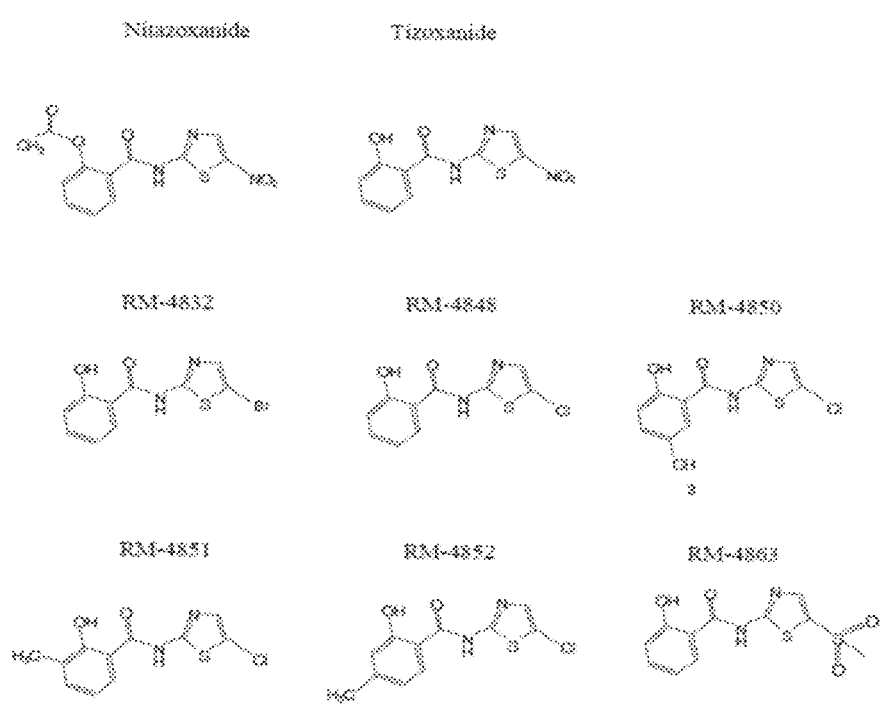
FIG. 1 provides the structures of exemplary thiazolides as disclosed herein.

Unless otherwise specified, "a" or "an" means "one or more."

Disclosed are thiazolide compounds having a formula (I)

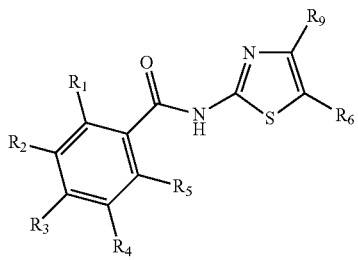

wherein $R_1$-$R_6$ have the meanings set forth above. In some embodiments, $R_1$, $R_2$, $R_3$, $R_4$, or $R_5$ is a —OS($O_2$)Rx, wherein Rx is alkyl, aryl, heteroaryl, arylalkyl, heteroarylalkyl, each of which may be optionally substituted. In some embodiments, $R_1$, $R_2$, $R_3$, $R_4$, or $R_5$ is —OSO$_2$—CH$_3$.

In some embodiments, one of $R_6$ or $R_9$ is H and the other is —SO$_2$-alkyl, preferably a —SO$_2$CH$_3$, —SO$_2$Et, —SO$_2$iPr, —CH$_2$SO$_2$Me, —NHSO$_2$Me or —SO$_2$-cyclopropyl.

The disclosed compounds include 2-benzamido-5-methylsulfonyl-thiazolides, 2-benzamido-4-methylsulfonyl-thiazolides and 2-(thiazol-2-ylcarbamoyl)phenyl methanesulfonates.

In some embodiments of the compounds of formula (I), $R_1$ is chosen from H, ($C_1$-$C_6$)-alkyl, ($C_2$-$C_6$)-alkenyl, ($C_2$-$C_6$)-alkynyl, phenyl, F, Cl, Br, I, (CH$_2$)$_{0-2}$—OR$_a$, a NO$_2$, (CH$_2$)$_{0-2}$—COOR$_b$, NH—(CH$_2$)$_{0-2}$—CO—R$_c$, (CH$_2$)$_{0-2}$O—CO—R$_d$, SR$_e$, PO(OH)(OH)$_{0-1}$, and a SO$_2$CH$_3$; $R_2$ through $R_5$ are, each independently of one another, chosen from H, ($C_1$-$C_6$)-alkyl, ($C_2$-$C_6$)-alkenyl, ($C_2$-$C_6$)-alkynyl, phenyl, F, Cl, Br, I, (CH$_2$)$_{0-2}$—OR$_a$, a NO$_2$, (CH$_2$)$_{0-2}$—COOR$_b$, NH—(CH$_2$)$_{0-2}$—CO—R$_c$, (CH$_2$)$_{0-2}$O—CO—R$_d$; SR$_e$ and PO(OH)(OH)$_{0-1}$; wherein R$_a$ through R$_e$, each independently of one another, is chosen from H, ($C_1$-$C_6$)-alkyl, ($C_2$-$C_6$)-alkenyl, ($C_2$-$C_6$)-alkynyl, and (CH$_2$)$_{0-2}$-phenyl; wherein $R_6$ is H or a SO$_2$CH$_3$; wherein the alkyl, the alkenyl, and the alkynyl in each case have from zero to nine H atoms replaced by F, Cl, Br, and/or I; and wherein if $R_1$ is a SO$_2$CH$_3$, then $R_6$ is H; and if $R_6$ is a SO$_2$CH$_3$, then $R_1$ is not SO$_2$CH$_3$.

In further embodiments of the compounds of formula (I), the compounds have formula (I), in which: $R_1$ through $R_5$ are, each independently of one another, chosen from H, ($C_1$-$C_4$)-alkyl, ($C_2$-$C_4$)-alkenyl, ($C_2$-$C_4$)-alkynyl, phenyl, F, Cl, Br, I, (CH$_2$)$_{0-2}$—OR$_a$, NO$_2$, (CH$_2$)$_{0-2}$—COOR$_b$, NH—(CH$_2$)$_{0-2}$—CO—R$_c$, (CH$_2$)$_{0-2}$O—CO—R$_d$; SR$_e$ and PO(OH)(OH)$_{0-1}$; wherein R$_a$ through R$_e$, each independently of one another, is chosen from H, ($C_1$-$C_4$)-alkyl, ($C_2$-$C_4$)-alkenyl, ($C_2$-$C_4$)-alkynyl, and (CH$_2$)$_{0-2}$-phenyl; wherein the alkyl, the alkenyl, and the alkynyl in each case have from zero to nine H atoms replaced by F, Cl, Br, and/or I; and $R_6$ is a SO$_2$CH$_3$.

In further embodiments of the compounds of formula (I), the compounds have formula (I), in which: $R_1$ through $R_5$ are, each independently of one another, chosen from H, ($C_1$-$C_4$)-alkyl, ($C_2$-$C_4$)-alkenyl, ($C_2$-$C_4$)-alkynyl, phenyl, F, Cl, Br, I, (CH$_2$)$_{0-2}$—OR$_a$, a NO$_2$, COOR$_b$, NH—CO—R$_c$, O—CO—R$_d$; SR$_e$ and PO(OH)(OH)$_{0-1}$; wherein R$_a$ through R$_e$, each independently of one another, is chosen from H, ($C_1$-$C_4$)-alkyl, ($C_2$-$C_4$)-alkenyl, ($C_2$-$C_4$)-alkynyl, and (CH$_2$)$_{0-2}$-phenyl; wherein the alkyl, the alkenyl, and the alkynyl in each case have from zero to nine H atoms replaced by F, Cl, Br, and/or I; and $R_6$ is SO$_2$CH$_3$.

In further embodiments of the compounds of formula (I), the compounds have formula (I), in which: $R_1$ through $R_5$ are, each independently of one another, chosen from H, ($C_1$-$C_4$)-alkyl, ($C_2$-$C_4$)-alkenyl, ($C_2$-$C_4$)-alkynyl, phenyl, F, Cl, Br, I, OR$_a$, a NO$_2$, COOR$_b$, NH—CO—R$_c$, O—CO—R$_d$; SR$_e$ and PO(OH)(OH)$_{0-1}$; wherein R$_a$ through R$_e$, each independently of one another, is chosen from ($C_1$-$C_4$)-alkyl, ($C_2$-$C_4$)-alkenyl, ($C_2$-$C_4$)-alkynyl, and (CH$_2$)$_{0-2}$-phenyl; wherein the alkyl, the alkenyl, and the alkynyl in each case have from zero to nine H atoms replaced by F, Cl, Br, and/or I; and $R_6$ is SO$_2$CH$_3$.

In further embodiments of the compounds of formula (I), the compounds have formula (I), in which: $R_1$ through $R_5$ are, each independently of one another, chosen from H, ($C_1$-$C_4$)-alkyl, F, Cl, Br, I, a NO$_2$, and PO(OH)(OH)$_{0-1}$; wherein R$_a$ through R$_e$, each independently of one another, is chosen from H and ($C_1$-$C_4$)-alkyl; and wherein the alkyl, the alkenyl, and the alkynyl in each case have from zero to nine H atoms replaced by F, Cl, Br, and/or I. In further embodiments, the compounds have formula (I), in which: $R_1$ through $R_5$ are, each independently of one another, chosen from H, ($C_1$-$C_4$)-alkyl, F, Cl, Br, I, a NO$_2$, and PO(OH)(OH)$_{0-1}$; wherein R$_a$ through R$_e$, each independently of one another, is chosen from H and ($C_1$-$C_4$)-alkyl; and $R_6$ is a SO$_2$CH$_3$.

In further embodiments of the compounds of formula (I), the compounds have formula (I), in which: $R_1$ through $R_5$ are, each independently of one another, chosen from H, F, Cl, Br, I, a $NO_2$, and $PO(OH)(OH)_{0-1}$; and $R_6$ is a $SO_2CH_3$.

In further embodiments of the compounds of formula (I), the compounds have formula (I), in which $R_1$ through $R_5$ are, each independently of one another, chosen from H, $(C_1-C_6)$-alkyl, F, Cl, Br, I, $(CH_2)_{0-2}$—$OR_a$, $NO_2$, $COOR_b$, NH—CO—$R_c$, O—CO—$R_d$; $SR_e$ and $PO(OH)(OH)_{0-1}$; wherein $R_a$ through $R_e$, each independently of one another, are chosen from H and $(C_1-C_6)$-alkyl; and $R_6$ is $SO_2CH_3$.

In further embodiments of the compounds of formula (I), the compounds have formula (I), in which: $R_1$ is a —$OS(O_2)$Rx, wherein Rx is alkyl, aryl, heteroaryl, arylalkyl, heteroarylalkyl, each of which may be optionally substituted; $R_2$ through $R_6$ are, each independently of one another, chosen from H, $(C_1-C_4)$-alkyl, $(C_2-C_4)$-alkenyl, $(C_2-C_4)$-alkynyl, phenyl, F, Cl, Br, I, $(CH_2)_{0-2}$—$OR_a$, $NO_2$, $(CH_2)_{0-2}$—$COOR_b$, NH—$(CH_2)_{0-2}$—CO—$R_c$, $(CH_2)_{0-2}$O—CO—$R_d$; $SR_e$ and $PO(OH)(OH)_{0-1}$; wherein $R_a$ through $R_e$, each independently of one another, is chosen from H, $(C_1-C_4)$-alkyl, $(C_2-C_4)$-alkenyl, $(C_2-C_4)$-alkynyl, and $(CH_2)_{0-2}$-phenyl; wherein the alkyl, the alkenyl, and the alkynyl in each case have from zero to nine H atoms replaced by F, Cl, Br, and/or I.

In further embodiments of the compounds of formula (I), the compounds have formula (I) in which: $R_1$ is a —$OS(O_2)$Rx, wherein Rx is alkyl, aryl, heteroaryl, arylalkyl, heteroarylalkyl, each of which may be optionally substituted; $R_2$ through $R_6$ are, each independently of one another, chosen from H, $(C_1-C_4)$-alkyl, $(C_2-C_4)$-alkenyl, $(C_2-C_4)$-alkynyl, phenyl, F, Cl, Br, I, $(CH_2)_{0-2}$—$OR_a$, a $NO_2$, $COOR_b$, NH—CO—$R_c$, O—CO—$R_d$; $SR_e$ and $PO(OH)(OH)_{0-1}$; wherein $R_a$ through $R_e$, each independently of one another, is chosen from H, $(C_1-C_4)$-alkyl, $(C_2-C_4)$-alkenyl, $(C_2-C_4)$-alkynyl, and $(CH_2)_{0-2}$-phenyl; wherein the alkyl, the alkenyl, and the alkynyl in each case have from zero to nine H atoms replaced by F, Cl, Br, and/or I.

In further embodiments of the compounds of formula (I), the compounds have formula (I) in which: $R_1$ is —$OS(O_2)$$CH_3$; $R_2$ through $R_5$ are, each independently of one another, chosen from H, $(C_1-C_4)$-alkyl, $(C_2-C_4)$-alkenyl, $(C_2-C_4)$-alkynyl, phenyl, F, Cl, Br, I, $OR_a$, $NO_2$, $COOR_b$, NH—CO—$R_c$, O—CO—$R_d$; $SR_e$ and $PO(OH)(OH)_{0-1}$; wherein $R_a$ through $R_e$, each independently of one another, is chosen from H, $(C_1-C_4)$-alkyl, $(C_2-C_4)$-alkenyl, $(C_2-C_4)$-alkynyl, and $(CH_2)_{0-2}$-phenyl; wherein the alkyl, the alkenyl, and the alkynyl in each case have from zero to nine H atoms replaced by F, Cl, Br, and/or I; and $R_6$ is H.

In further embodiments of the compounds of formula (I), the compounds have formula (I) in which: $R_1$ is a —$OS(O_2)$$CH_3$; $R_2$ through $R_5$ are, each independently of one another, chosen from H, $(C_1-C_4)$-alkyl, F, Cl, Br, I, $NO_2$, and $PO(OH)(OH)_{0-1}$; wherein $R_a$ through $R_e$, each independently of one another, is chosen from H and $(C_1-C_4)$-alkyl; and wherein the alkyl, the alkenyl, and the alkynyl in each case have from zero to nine H atoms replaced by F, Cl, Br, and/or I; and $R_6$ is H.

In further embodiments of the compounds of formula (I), the compounds have formula (I) in which: $R_1$ is a —$OS(O_2)$$CH_3$; $R_1$ through $R_5$ are, each independently of one another, chosen from H, $(C_1-C_4)$-alkyl, F, Cl, Br, I, $NO_2$, and $PO(OH)(OH)_{0-1}$; wherein $R_a$ through $R_e$, each independently of one another, is chosen from H and $(C_1-C_4)$-alkyl; and $R_6$ is H.

In further embodiments of the compounds of formula (I), the compounds have formula (I) in which: $R_1$ is a —$OS(O_2)$$CH_3$; $R_2$ through $R_5$ are, each independently of one another, chosen from H, F, Cl, Br, I, $NO_2$, and $PO(OH)(OH)_{0-1}$; and $R_6$ is H.

In further embodiments of the compounds of formula (I), the compounds have formula (I) in which: $R_1$ is —$OS(O_2)$$CH_3$; $R_2$ through $R_5$ are, each independently of one another, chosen from H, $(C_1-C_6)$-alkyl, F, Cl, Br, I, $(CH_2)_{0-2}$—$OR_a$, $NO_2$, $COOR_b$, NH—CO—$R_c$, O—CO—$R_d$; $SR_e$ and $PO(OH)(OH)_{0-1}$; and wherein $R_a$ through $R_e$, each independently of one another, are chosen from H and $(C_1-C_6)$-alkyl; and $R_6$ is H.

In the formulas for the disclosed compounds, $(CH_2)_{0-2}$ represents a bond when the subscript is zero, $(CH_2)$ when the subscript is 1, and $CH_2CH_2$ when the subscript is 2. Similarly, the term $(CH_2)_{0-2}$ in, for example, $(CH_2)_{0-2}$—CO—X represents CO—X, $CH_2$—CO—X, and $(CH_2)_2$—CO—X. Other recite $(CH_2)_{0-2}$ and similar terms, such as $(CH_2)_{0-1}$, $(CH_2)_{1-2}$, etc. The meaning of each term could be readily determined by one of ordinary skill.

The disclosed compounds include compounds of formula (I), salts, and solvates thereof. For example, in some embodiments, the compound of the present invention may be a salt of a solvate.

The term "salts" is used in its broadest sense. For example, the term salts includes hydrogen salts and hydroxide salts with ions of the present compound. In some embodiments, the term salt may be a subclass referred to as pharmaceutically acceptable salts, which are salts of the present compounds having a pharmacological activity and which are neither biologically nor otherwise undesirable. In all embodiments, the salts can be formed with acids, such as, without limitation, hydrogen, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycero-phosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. In all embodiments, the salts can be formed with bases, such as, without limitation, hydroxide, ammonium salts, alkali metal salts such as lithium, sodium and potassium salts, alkaline earth metal salts such as calcium, magnesium salts, aluminum salts, salts with organic bases such as ammonia, methylamine, diethylamine, ethanolamine, dicyclohexylamine, N-methylmorpholine, N-methyl-D-glucamine, and salts with amino acids such as arginine and lysine. Basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The term "therapeutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reacting a carboxy, phenol or similar group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "solvates" is used in its broadest sense. For example, the term solvates includes hydrates formed when a compound of the present invention contains one or more bound water molecules.

As used in the present specification the following terms have the meanings indicated:

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. Examples of acyl groups include formyl, alkanoyl and aroyl radicals.

The term "acylamino" embraces an amino radical substituted with an acyl group. An example of an "acylamino" radical is acetylamino (CH$_3$C(O)NH—).

The term "alkenyl," as used herein, alone or in combination, refers to a straight-chain, branched-chain, and cyclic unsaturated hydrocarbon radical having one or more double bonds and containing from 2 to 20, preferably 2 to 6, carbon atoms. The term "alkenyl groups" is used in its broadest sense. Alkenylene refers to a carbon-carbon double bond system attached at two or more positions such as ethenylene [(—CH=CH—),(—C::C—)]. For example, (C$_2$-C$_8$) alkenyl groups embraces straight, branched, and cyclic hydrocarbon chains containing 2 to 8 carbon atoms having at least one double bond, Examples of suitable alkenyl radicals include ethenyl, propenyl, iso-propenyl, butenyl, iso-butenyl, sec-butenyl, tert-butenyl, n-pentenyl, n-hexenyl, and the like, unless otherwise indicated.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkoxyalkoxy," as used herein, alone or in combination, refers to one or more alkoxy groups attached to the parent molecular moiety through another alkoxy group. Examples include ethoxyethoxy, methoxypropoxyethoxy, ethoxypentoxyethoxyethoxy and the like.

The term "alkoxyalkyl," as used herein, alone or in combination, refers to an alkoxy group attached to the parent molecular moiety through an alkyl group. The term "alkoxyalkyl" also embraces alkoxyalkyl groups having one or more alkoxy groups attached to the alkyl group, that is, to form monoalkoxyalkyl and dialkoxyalkyl groups.

The term "alkoxycarbonyl," as used herein, alone or in combination, refers to an alkoxy group attached to the parent molecular moiety through a carbonyl group. Examples of such "alkoxycarbonyl" groups include methoxycarbonyl, ethoxycarbonyl, propoxycarbonyl, butoxycarbonyl and hexyloxycarbonyl.

The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl.

The term "alkyl," as used herein, alone or in combination, refers to a straight-chain or branched-chain alkyl radical containing from 1 to and including 20, preferably 1 to 10, and more preferably 1 to 6, carbon atoms. The term "alkyl groups" is used in its broadest sense. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. For example, the O(C$_1$-C$_8$)-alkyl groups comprises the straight O(C$_1$-C$_8$)-alkyl groups as well as the branched O(C$_1$-C$_8$)-alkyl groups. For another example, the term comprises cycloalkyl groups, as for example, the (C$_1$-C$_8$)-alkyl groups comprises the (C$_3$-C$_8$)-cycloalkyl groups.

The term "alkylene," as used herein, alone or in combination, refers to a saturated aliphatic group derived from a straight or branched chain saturated hydrocarbon attached at two or more positions, such as methylene (—CH$_2$—).

The term "alkylamino," as used herein, alone or in combination, refers to an amino group attached to the parent molecular moiety through an alkyl group.

The term "alkylaminocarbonyl" as used herein, alone or in combination, refers to an alkylamino group attached to the parent molecular moiety through a carbonyl group. Examples of such radicals include N-methylaminocarbonyl and N,N-dimethylcarbonyl.

The term "alkylcarbonyl" and "alkanoyl," as used herein, alone or in combination, refers to an alkyl group attached to the parent molecular moiety through a carbonyl group. Examples of such groups include methylcarbonyl and ethylcarbonyl.

The term "alkylidene," as used herein, alone or in combination, refers to an alkenyl group in which one carbon atom of the carbon-carbon double bond belongs to the moiety to which the alkenyl group is attached.

The term "alkylsulfinyl," as used herein, alone or in combination, refers to an alkyl group attached to the parent molecular moiety through a sulfinyl group. Examples of alkylsulfinyl groups include methylsulfinyl, ethylsulfinyl, butylsulfinyl and hexylsulfinyl.

The term "alkylsulfonyl," as used herein, alone or in combination, refers to an alkyl group attached to the parent molecular moiety through a sulfonyl group. Examples of alkylsulfinyl groups include methanesulfonyl, ethanesulfonyl, tert-butanesulfonyl, and the like.

The term "alkylthio," as used herein, alone or in combination, refers to an alkyl thioether (R—S—) radical wherein the term alkyl is as defined above. Examples of suitable alkyl thioether radicals include methylthio, ethylthio, n-propylthio, isopropylthio, n-butylthio, iso-butylthio, sec-butylthio, tert-butylthio, ethoxyethylthio, methoxypropoxyethylthio, ethoxypentoxyethoxyethylthio and the like.

The term "alkylthioalkyl" embraces alkylthio radicals attached to an alkyl radical. Alkylthioalkyl radicals include "lower alkylthioalkyl" radicals having alkyl radicals of one to six carbon atoms and an alkylthio radical as described above. Examples of such radicals include methylthiomethyl.

The term "alkynyl," as used herein in its broadest sense, alone or in combination, refers to a straight-chain, branched chain hydrocarbon and cyclic unsaturated hydrocarbon radicals having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). For example, $(C_2-C_8)$alkynyl groups embraces straight, branched, and cyclic hydrocarbon chains containing 2 to 8 carbon atoms having at least one triple bond, and the term includes but is not limited to substituents such as ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl, and the like, unless otherwise indicated.

The term "amido," as used herein, alone or in combination, refers to an amino group as described below attached to the parent molecular moiety through a carbonyl group. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein.

The term "amino," as used herein, alone or in combination, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl, heteroarylalkenyl, heteroarylalkyl, heterocycle, heterocycloalkenyl, and heterocycloalkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the heterocycloalkenyl and the heterocycloalkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxy-alkyl, nitro, and oxo.

The term "aminoalkyl," as used herein, alone or in combination, refers to an amino group attached to the parent molecular moiety through an alkyl group. Examples include aminomethyl, aminoethyl and aminobutyl. The term "alkylamino" denotes amino groups which have been substituted with one or two alkyl radicals. Suitable "alkylamino" groups may be mono- or dialkylated, forming groups such as, for example, N-methylamino, N-ethylamino, N,N-dimethylamino, N,N-diethylamino and the like.

The terms "aminocarbonyl" and "carbamoyl," as used herein, alone or in combination, refer to an amino-substituted carbonyl group, wherein the amino group can be a primary or secondary amino group containing substituents selected from alkyl, aryl, aralkyl, cycloalkyl, cycloalkylalkyl radicals and the like.

The term "aminocarbonylalkyl," as used herein, alone or in combination, refers to an aminocarbonyl radical attached to an alkyl radical, as described above. An example of such radicals is aminocarbonylmethyl. The term "amidino" denotes an —C(NH)NH$_2$ radical. The term "cyanoamidino" denotes an —C(N—CN)NH$_2$ radical.

The term "aralkenyl" or "arylalkenyl," as used herein, alone or in combination, refers to an aryl group attached to the parent molecular moiety through an alkenyl group.

The term "aralkoxy" or "arylalkoxy," as used herein, alone or in combination, refers to an aryl group attached to the parent molecular moiety through an alkoxy group.

The term "aralkyl" or "arylalkyl," as used herein, alone or in combination, refers to an aryl group attached to the parent molecular moiety through an alkyl group.

The term "aralkylamino" or "arylalkylamino," as used herein, alone or in combination, refers to an arylalkyl group attached to the parent molecular moiety through a nitrogen atom, wherein the nitrogen atom is substituted with hydrogen.

The term "aralkylidene" or "arylalkylidene," as used herein, alone or in combination, refers to an aryl group attached to the parent molecular moiety through an alkylidene group The term "aralkylthio" or "arylalkylthio," as used herein, alone or in combination, refers to an arylalkyl group attached to the parent molecular moiety through a sulfur atom.

The term "aralkynyl" or "arylalkynyl," as used herein, alone or in combination, refers to an aryl group attached to the parent molecular moiety through an alkynyl group.

The term "aralkoxycarbonyl," as used herein, alone or in combination, refers to a radical of the formula aralkyl-O—C(O)— in which the term "aralkyl," has the significance given above. Examples of an aralkoxycarbonyl radical are benzyloxycarbonyl (Z or Cbz) and 4-methoxyphenylmethoxycarbonyl (MOS).

The term "aralkanoyl," as used herein, alone or in combination, refers to an acyl radical derived from an aryl-substituted alkanecarboxylic acid such as benzoyl, phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" refers to an acyl radical derived from an arylcarboxylic acid, "aryl" having the meaning given below. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aryl," as used herein, alone or in combination, means a carbocyclic aromatic system containing one, two or three rings wherein such rings may be attached together in a pendent manner or may be fused. The term "aryl" embraces aromatic radicals such as phenyl, naphthyl, anthracenyl, phenanthryl, and biphenyl. The aryl groups of the present invention can be optionally substituted with one, two, three, four, or five substituents independently selected from the groups as defined herein.

The term "arylamino" as used herein, alone or in combination, refers to an aryl group attached to the parent moiety through an amino group, such as N-phenylamino, and the like.

The terms "arylcarbonyl" and "aroyl," as used herein, alone or in combination, refer to an aryl group attached to the parent molecular moiety through a carbonyl group.

The term "aryloxy," as used herein, alone or in combination, refers to an aryl group attached to the parent molecular moiety through an oxygen atom.

The term "arylsulfonyl," as used herein, alone or in combination, refers to an aryl group attached to the parent molecular moiety through a sulfonyl group.

The term "arylthio," as used herein, alone or in combination, refers to an aryl group attached to the parent molecular moiety through a sulfur atom.

The terms "carboxy" or "carboxyl", whether used alone or with other terms, such as "carboxyalkyl", denotes —$CO_2H$.

The terms "benzo" and "benz," as used herein, alone or in combination, refer to the divalent radical $C_6H_4$=derived from benzene. Examples include benzothiophene and benzimidazole.

The term "O-carbamyl" as used herein, alone or in combination, refers to a —OC(O)NR, group-with R as defined herein.

The term "C-linked" as used herein, alone or in combination, refers to any substituent that is attached to the parent molecular moiety through a carbon-carbon bond.

The term "N-carbamyl" as used herein, alone or in combination, refers to a ROC(O)NH— group, with R as defined herein.

The term "carbonate" as used herein, alone or in combination, refers to a —O—C(=O)OR group, with R as defined herein.

The term "carbonyl," as used herein, when alone includes formyl [—C(O)H] and in combination is a —C(O)— group.

The term "carboxy," as used herein, refers to —C(O)OH or the corresponding "carboxylate" such as a carboxylic acid salt derivative or ester derivative. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably three to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multi-centered) saturated or partially unsaturated type. The latter type of isomer is exemplified in general by bicyclo[2,2,2] octane, bicyclo[2,2,2]octane, bicyclo[1,1,1]pentane, camphor and bicyclo[3,2,1]octane.

The term "cycloalkenyl," as used herein, alone or in combination, refers to a partially unsaturated monocyclic, bicyclic or tricyclic radical wherein each cyclic moiety contains from 3 to 12, preferably five to eight, carbon atom ring members and which may optionally be a benzo fused ring system which is optionally substituted as defined herein. Examples of such cycloalkenyl radicals include cyclopentenyl, cyclohexenyl, cyclohexadienyl, cycloheptenyl, cyclooctadienyl, -1H-indenyl and the like.

The term "cycloalkylalkyl," as used herein, alone or in combination, refers to an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "cycloalkenylalkyl," as used herein, alone or in combination, refers to an alkyl radical as defined above which is substituted by a cycloalkenyl radical as defined above. Examples of such cycloalkenylalkyl radicals include 1-methylcyclohex-1-enyl-, 4-ethylcyclohex-1-enyl-, 1-butylcyclopent-1-enyl-, 3-methylcyclopent-1-enyl- and the like.

The term "ester," as used herein, alone or in combination, refers to a carbonyloxy —(C=O)O— group bridging two moieties linked at carbon atoms. Examples include ethyl benzoate, n-butyl cinnamate, phenyl acetate and the like.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a halohydrocarbyl group attached at two or more positions. Examples include fluoromethylene (—CFH—), difluoromethylene (—$CF_2$—), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3.

The term "heteroaryl," as used herein, alone or in combination, refers to an aromatic five- or six-membered ring, where at least one atom is selected from the group consisting of N, O, and S, and the remaining ring atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes systems where a heteroaryl ring is fused to an aryl group, as defined herein, a heterocycle group, as defined herein, or an additional heteroaryl group. Heteroaryls are exemplified by benzothienyl, benzoxazolyl, benzofuranyl, benzimidazolyl, benzthiazolyl benzotriazolyl, cinnolinyl, furyl, imidazolyl, triazolyl [e.g., 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], indazolyl, indolyl, isoxazolyl, isoquinolinyl, isothiazolyl, naphthyridinyl, oxadiazolyl [e.g., 1,2,4-oxadiazolyl, 1,3,4-oxadiazolyl, 1,2,5-oxadiazolyl, etc.], oxazolyl, isoxazolyl, purinyl, thiazolyl, isothiazolyl, thienopyridinyl, thienyl, thiadiazolyl [e.g., 1,2,4-thiadiazolyl, 1,3,4-thiadiazolyl, 1,2,5-thiadiazolyl, etc.], pyridinyl, pyridazinyl, pyrimidinyl, pyrazinyl, pyrazolyl, pyrrolyl, pyrido[2,3-d]pyrimidinyl, pyrrolo[2,3-b]pyridinyl, quinazolinyl, quinolinyl, thieno[2,3-c]pyridinyl, tetrazolyl, triazinyl, and the like. The heteroaryl groups of the present invention can be optionally substituted with one, two, three, four, or five substituents independently selected from the groups as defined herein.

Examples of preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl The term "heteroaralkyl" or "heteroarylalkyl," as used herein, alone or in combination, refers to a heteroaryl group attached to the parent molecular moiety through an alkyl group.

The term "heteroaralkenyl" or "heteroarylalkenyl," as used herein, alone or in combination, refers to a heteroaryl group attached to the parent molecular moiety through an alkenyl group.

The term "heteroaralkoxy" or "heteroarylalkoxy," as used herein, alone or in combination, refers to a heteroaryl group attached to the parent molecular moiety through an alkoxy group.

The term "heteroaralkylidene" or "heteroarylalkylidene," as used herein, alone or in combination, refers to a heteroaryl group attached to the parent molecular moiety through an alkylidene group.

The term "heteroaryloxy," as used herein, alone or in combination, refers to a heteroaryl group attached to the parent molecular moiety through an oxygen atom.

The term "heteroarylsulfonyl," as used herein, alone or in combination, refers to a heteroaryl group attached to the parent molecular moiety through a sulfonyl group.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "heterocycloalkenyl," as used herein, alone or in combination, refers to a heterocycle group attached to the parent molecular moiety through an alkenyl group.

The term "heterocycloalkoxy," as used herein, alone or in combination, refers to a heterocycle group attached to the parent molecular group through an oxygen atom.

The term "heterocycloalkyl," as used herein, alone or in combination, refers to an alkyl radical as defined above in which at least one hydrogen atom is replaced by a heterocyclo radical as defined above, such as pyrrolidinylmethyl, tetrahydrothienylmethyl, pyridylmethyl and the like.

The term "heterocycloalkylidene," as used herein, alone or in combination, refers to a heterocycle group attached to the parent molecular moiety through an alkylidene group.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl" as used herein, alone or in combination, refers to a linear or branched alkyl group having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptoalkyl" as used herein, alone or in combination, refers to an R'SR— group, where R and R' are as defined herein.

The term "mercaptomercaptyl" as used herein, alone or in combination, refers to a RSR'S— group, where R is as defined herein.

The term "mercaptyl" as used herein, alone or in combination, refers to an RS— group, where R is as defined herein.

The term "null" refers to a lone electron pair.

The term "nitro," as used herein, alone or in combination, refers to —$NO_2$.

The term "optionally substituted" means the anteceding group may be substituted or unsubstituted. When substituted, the substituents of an "optionally substituted" group may include, without limitation, one or more substituents independently selected from the following groups or designated subsets thereof, alone or in combination: hydrogen, carbonyl (oxo), carboxyl, lower alkyl carboxylate, lower alkyl carbonate, lower alkyl carbamate, halogen, hydroxy, amino, amido, cyano, hydrazinyl, hydrazinylcarbonyl, alkylhydrazinyl, dialkylhydrazinyl, arylhydrazinyl, heteroarylhydrazinyl, nitro, thiol, sulfonic acid, trisubstituted silyl, urea, acyl, acyloxy, acylamino, arylthio, lower alkyl, lower alkylamino, lower dialkylamino, lower alkyloxy, lower alkoxyalkyl, lower alkylthio, lower alkylsulfonyl, lower alkenyl, lower alkenylamino, lower dialkenylamino, lower alkenyloxy, lower alkenylthio, lower alkenyl sulfonyl, lower alkynyl, lower alkynylamino, lower dialkynylamino, lower alkynyloxy, lower alkynylthio, lower alkynylsulfonyl, lower cycloalkyl, lower cycloalkyloxy, lower cycloalkylamino, lower cycloalkylthio, lower cycloalkylsulfonyl, lower cycloalkylalkyl, lower cycloalkylalkyloxy, lower cycloalkylalkylamino, lower cycloalkylalkylthio, lower cycloalkylalkylsulfonyl, aryl, aryloxy, arylamino, arylthio, arylsulfonyl, arylalkyl, arylalkyloxy, arylalkylamino, arylalkylthio, arylalkylsulfonyl, heteroaryl, heteroaryloxy, heteroarylamino, heteroarylthio, heteroarylsulfonyl, heteroarylalkyl, heteroarylalkyloxy, heteroarylalkylamino, heteroarylalkylthio, heteroarylalkylsulfonyl, heterocycloalkyl, heterocycloalkyloxy, heterocycloalkylamino, heterocycloalkylthio, heterocycloalkylsulfonyl, lower haloalkyl, lower haloalkenyl, lower haloalkynyl, lower perhaloalkyl, lower perhaloalkoxy, lower haloalkoxy, and lower acyloxy. Two substituents may be joined together to form a fused four-, five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. All pendant aryl, heteroaryl, and heterocyclo moieties can be further optionally substituted with one, two, three, four, or five substituents independently selected from the groups listed above.

The terms "oxy" or "oxa," as used herein, alone or in combination, refer to —O—.

The term "oxo" as used herein, alone or in combination, refers to a doubly bonded oxygen =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate" as used herein, alone or in combination, refers to the —P(=O)(OR)(OR1) group.

The term "phosphinate" as ues herein, alone or in combination, refers to the —P(=O)(R)(OR1) group.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S and —S—.

The term "sulfinyl," as used herein, alone or in combination, refers to —S(O)—.

The term "sulfonyl," as used herein, alone or in combination, refers to —SO$_2$—.

The term "N-sulfonamido" refers to a RS(=O)$_2$NH— group with R as defined herein.

The term "S-sulfonamido" refers to a —S(=O)$_2$NR$_2$, group, with R as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thioether," as used herein, alone or in combination, refers to a thio group bridging two moieties linked at carbon atoms.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NH— group, with R as defined herein.

The term "O-thiocarbamyl" refers to a —OC(S)NR, group with R as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

The term "urea," as used herein, alone or in combination, refers to —N(R)C(=O)N(R)(R), with R as defined herein.

The term "alkyl" is used in its broadest sense. For example, the term refers to a branched, unbranched, and cyclic saturated hydrocarbon chains comprising a designated number of carbon atoms. For example, the O(C$_1$-C$_8$)-alkyl comprises the straight O(C$_1$-C$_8$)-alkyl as well as the branched O(C$_1$-C$_8$)-alkyl. For another example, the term comprises cycloalkyl, as for example, the (C$_1$-C$_8$)-alkyl comprises the (C$_3$-C$_8$)-cycloalkyl. In all embodiments, the term includes but is not limited to substituents such as methyl, ethyl, propyl, iso-propyl, butyl, iso-butyl, sec-buty, tert-butyl, n-pentyl, n-hexyl, and the like, unless otherwise indicated.

The term "alkenyl" is used in its broadest sense. For example, the term alkenyl refers to branched, unbranched, and cyclic unsaturated hydrocarbon chains comprising a designated number of carbon atoms. For example, (C$_2$-C$_8$)alkenyl embraces straight, branched, and cyclic hydrocarbon chains containing 2 to 8 carbon atoms having at least one double bond, and the term includes but is not limited to substituents such as ethenyl, propenyl, iso-propenyl, butenyl, iso-butenyl, sec-butenyl, tert-butenyl, n-pentenyl, n-hexenyl, and the like, unless otherwise indicated.

The term "alkynyl" is used in its broadest sense. For example, the term alkynyl refers to branched, unbranched, and cyclic unsaturated hydrocarbon chains comprising a designated number of carbon atoms. For example, (C$_2$-C$_8$)alkynyl embraces straight, branched, and cyclic hydrocarbon chains containing 2 to 8 carbon atoms having at least one triple bond, and the term includes but is not limited to substituents such as ethynyl, propynyl, butynyl, n-pentynyl and branched counterparts, n-hexynyl and branched counterparts, and the like, unless otherwise indicated.

The term "heteroaryl," as used herein, alone or in combination, refers to 3 to 14 membered, preferably 5 to 7 membered, unsaturated heterocyclic rings wherein at least one atom is selected from the group consisting of O, S, and N. Heteroaryl are exemplified by: unsaturated 5 to 14 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.]tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic groups containing an oxygen atom, for example, pyranyl, furyl, etc.; unsaturated 3 to 6-membered heteromonocyclic groups containing a sulfur atom, for example, thienyl, etc.; unsaturated 3- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.]etc.; unsaturated condensed heterocyclic groups containing 1 to 2 oxygen atoms and 1 to 3 nitrogen atoms [e.g. benzoxazolyl, benzoxadiazolyl, etc.]; unsaturated 3 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] and isothiazolyl; unsaturated condensed heterocyclic groups containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like.

For example, heteroaryl may be pyrimidinyl, pyridinyl, benzimidazolyl, thienyl, benzothiazolyl, benzofuranyl and indolinyl. Preferred heteroaryls include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl In any embodiment of the compounds of formula (I), $R_2$ through $R_5$ may be the same, may be different, or some members of $R_2$ through $R_5$ may be the same while the others are different. Any combination is possible.

In any embodiment of the compounds of formula (I), either $R_1$ or $R_6$ may be $SO_2CH_3$. However, if $R_1$ is $SO_2CH_3$, then $R_6$ is H. In another embodiment, if $R_6$ is $SO_2CH_3$, then $R_1$ is chosen from H, $(C_1-C_6)$-alkyl, $(C_2-C_6)$-alkenyl, $(C_2-C_6)$-alkynyl, phenyl, F, Cl, Br, I, $(CH_2)_{0-2}$—$OR_a$, a $NO_2$, $(CH_2)_{0-2}$—$COOR_b$, NH—$(CH_2)_{0-2}$—CO—$R_c$, $(CH_2)_{0-2}$O—CO—$R_d$; $SR_e$ and $PO(OH)(OH)_{0-1}$.

In any embodiment of the compounds of formula (I) where $R_6$ is $SO_2CH_3$, $R_1$ and/or $R_5$ may independently be a group or atom other than a hydrogen atom. For example, $R_1$ and/or $R_5$ may independently be chosen from $(C_1-C_8)$-alkyl, F, Cl, Br, I, $(CH_2)_{0-2}$—$OR_a$, $(CH_2)_{0-2}$—CO—$R_f$, $(CH_2)_{0-2}$—$COOR_g$, $(CH_2)_{0-2}$—CO—$NR_hR_i$, O—$(CH_2)_{0-2}$—CO—$OR_k$, $(CH_2)_{0-2}$O—CO—$R_u$, and $(CH_2)_{0-2}PO(OR_v)(OR_w)$. In any embodiment, $R_1$ and/or $R_5$ may independently be chosen from $OR_a$, CO—$R_f$, $COOR_g$, CO—$NR_hR_i$, O—CO—$OR_k$, O—CO—$R_u$, and $PO(OR_v)(OR_w)_{0-1}$. In some embodiments, $R_1$ and/or $R_5$ may independently be chosen from OH, O—CO—$CH_3$, O—CO—$CH_2CH_3$, $CH_3$, $CH_2CH_3$, and $PO(OH)_2$. $R_a$ through $R_k$ and $R_m$ through $R_u$, each independently of one another, may be chosen from H, $(C_1-C_8)$-alkyl, and $(CH_2)_{1-2}$-phenyl. In any embodiment, $R_a$ through $R_k$ and $R_m$ through $R_u$, each independently of one another, may be chosen from H, $(C_1-C_4)$-alkyl, and phenyl. In any embodiment, $R_a$ through $R_k$ and $R_m$ through $R_u$, each independently of one another, may be chosen from H and $(C_1-C_3)$-alkyl. $R_v$ and $R_w$, each independently of one another, may be chosen from H, $(C_1-C_8)$-alkyl, $(C_2-C_8)$-alkenyl, $(C_2-C_8)$-alkynyl, $(CH_2)_{1-2}$-phenyl. In any embodiment, $R_v$ and $R_w$, each independently of one another, may be chosen from H, $(C_1-C_4)$-alkyl, and $(CH_2)_{1-2}$-phenyl. In any embodiment, $R_v$ and $R_w$, each independently of one another, may be chosen from H and $(C_1-C_3)$-alkyl.

In any embodiment of the compounds of formula (I), alkyl, alkenyl, and alkynyl in each case may, or may not, have from zero to nine H atoms replaced by F, Cl, Br, and/or I. In any embodiment, the phenyl in each case may, or may not, have from zero to five H atoms replaced by F, Cl, Br, and/or I. In any embodiment, alkyl in each case can have from zero to four H atoms replaced by OH and/or $NH_2$. In any embodiment, phenyl in each case has from zero to two H atoms replaced by $NO_2$ and/or $(CH_2)_{0-2}CO$—$(C_1-C_6)$-alkyl and/or $(CH_2)_{0-2}CO$—$(C_2-C_6)$-alkenyl and/or $(CH_2)_{0-2}CO$—$(C_2-C_6)$-alkynyl and/or $(CH_2)_{0-2}CO$—$(CH_2)_{0-2}$-phenyl. In any embodiment, the phenyl in each case can have from zero to two H atoms replaced by a $NO_2$ and/or CO—$(C_1-C_3)$-alkyl and/or CO—$(CH_2)_{1-2}$-phenyl.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, $NHCH_3$, $N(CH_3)_2$, SH, $SCH_3$, $CO_2CH_3$, $C(O)NH_2$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." The term "lower" denotes the presence of no more than six carbon atoms.

Examples of compounds of the present invention may include, but are not limited to the following compounds listed in Table 7 below:

TABLE 7
| No. | Structure |
|---|---|
| 1 | 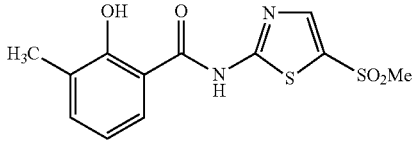 [SMILES: Cc1cccc(C(=O)Nc2ncc(S(C)(=O)=O)s2)c1O] |
| 2 | 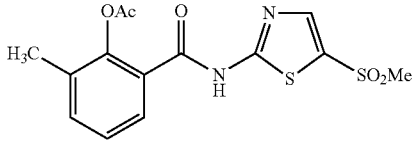 |
| 3 | 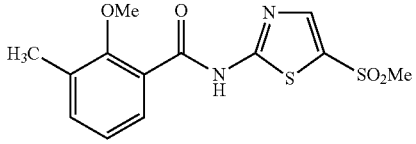 [SMILES: CC(=O)Oc1c(C)cccc1C(=O)Nc1ncc(S(C)(=O)=O)s1] |
| 4 | 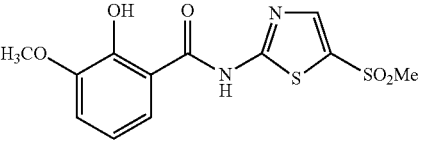 [SMILES: COc1cccc(C(=O)Nc2ncc(S(C)(=O)=O)s2)c1O] |
| 5 | 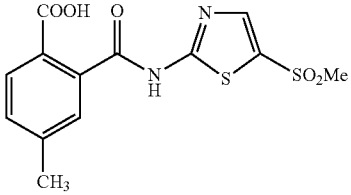 [SMILES: Cc1ccc(C(=O)O)c(C(=O)Nc2ncc(S(C)(=O)=O)s2)c1] |
| 6 | 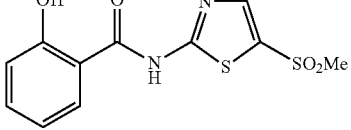 |
| 7 | 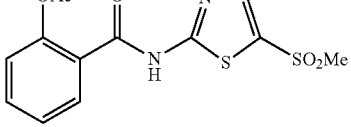 |
| 8 | 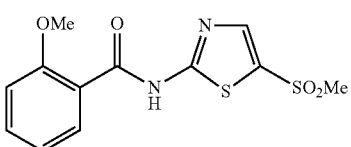 |
| 9 | 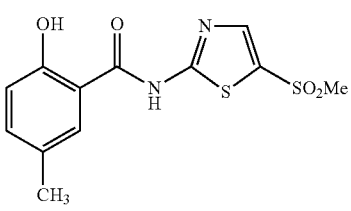 |

TABLE 7-continued
| No. | Structure |
|---|---|
| 10 | 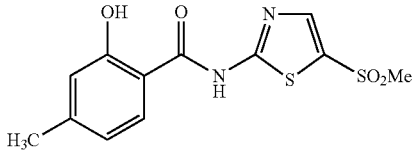 [SMILES: Cc1ccc(C(=O)Nc2ncc(S(C)(=O)=O)s2)c(O)c1] |
| 11 | 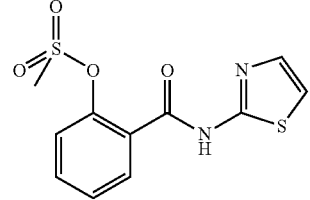 [SMILES: CS(=O)(=O)Oc1ccccc1C(=O)Nc1nccs1] |
| 12 | 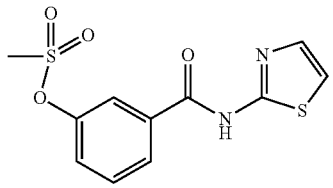 [SMILES: CS(=O)(=O)Oc1cccc(C(=O)Nc2nccs2)c1] |
| 13 | 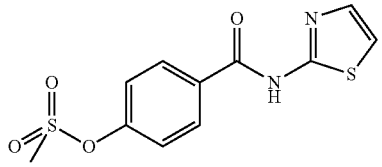 [SMILES: CS(=O)(=O)Oc1ccc(C(=O)Nc2nccs2)cc1] |
| 14 | 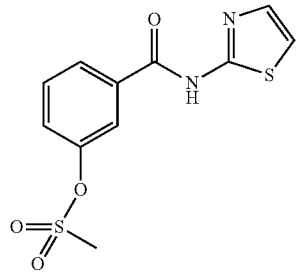 [SMILES: CS(=O)(=O)Oc1cccc(C(=O)Nc2nccs2)c1] |
| 15 | 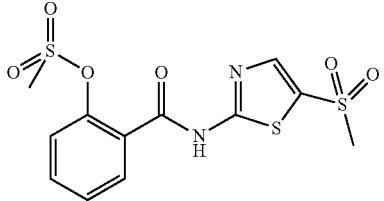 [SMILES: CS(=O)(=O)Oc1ccccc1C(=O)Nc1ncc(S(C)(=O)=O)s1] |
| 16 | 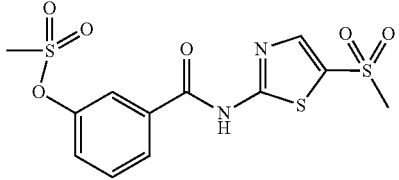 |

TABLE 7-continued

| No. | Structure |
|-----|-----------|
| 17 | (4-methylsulfonyloxyphenyl)-C(=O)-NH-(5-methylsulfonyl-thiazol-2-yl) |
| 18 | (3-methylsulfonyloxyphenyl)-C(=O)-NH-(5-methylsulfonyl-thiazol-2-yl) |
| 19 | (2-methylsulfonyloxyphenyl)-C(=O)-NH-(5-fluoro-thiazol-2-yl) |
| 20 | (3-ethylsulfonyloxyphenyl)-C(=O)-NH-(5-chloro-thiazol-2-yl) |
| 21 | (4-isopropylsulfonyloxyphenyl)-C(=O)-NH-(5-bromo-thiazol-2-yl) |
| 22 | (3-(neopentylsulfonyloxy)phenyl)-C(=O)-NH-(5-ethyl-thiazol-2-yl) |
| 23 | (2-(2-fluorophenylsulfonyloxy)phenyl)-C(=O)-NH-(thiazol-2-yl) |

TABLE 7-continued

| No. | Structure |
|---|---|
| 24 | 4-cyano-2-(trifluoromethyl)benzyl methanesulfonate-linked 3-(thiazol-2-ylcarbamoyl)phenyl ester |
| 25 | 5-methoxypyridine-2-sulfonic acid 4-(thiazol-2-ylcarbamoyl)phenyl ester |
| 26 | (4,4-dimethylcyclohexyl)methanesulfonic acid 3-(thiazol-2-ylcarbamoyl)phenyl ester |
| 27 | methanesulfonic acid 2-((5-nitrothiazol-2-yl)carbamoyl)phenyl ester |
| 28 | methanesulfonic acid 3-((5-cyanothiazol-2-yl)carbamoyl)phenyl ester |

TABLE 7-continued
| No. | Structure |
|-----|-----------|
| 29 | 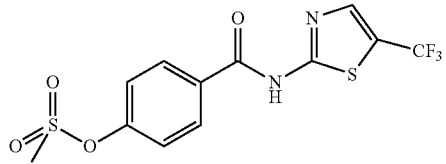 [SMILES: CS(=O)(=O)Oc1ccc(C(=O)Nc2ncc(C(F)(F)F)s2)cc1] |
| 30 | 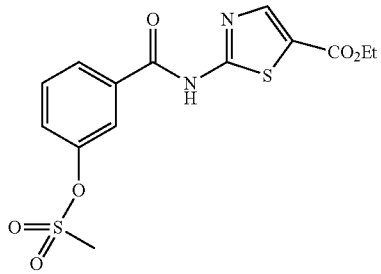 [SMILES: CCOC(=O)c1cnc(NC(=O)c2cccc(OS(C)(=O)=O)c2)s1] |
| 31 | 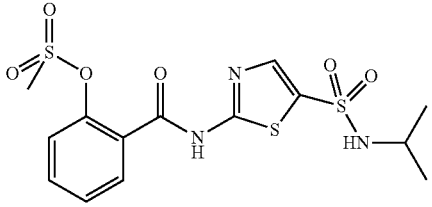 [SMILES: CC(C)NS(=O)(=O)c1cnc(NC(=O)c2ccccc2OS(C)(=O)=O)s1] |
| 32 | 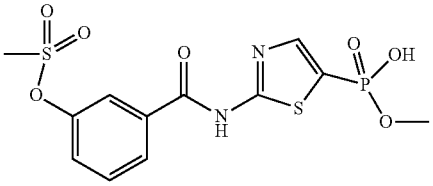 |
| 33 | 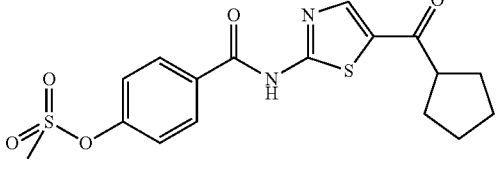 |
| 34 | 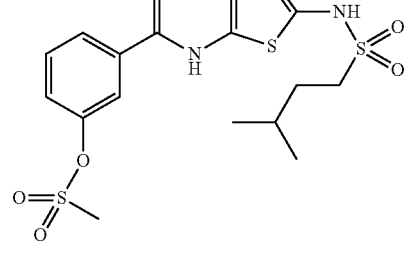 |
| 35 | 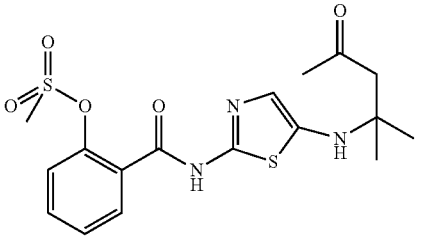 [SMILES: CC(=O)CC(C)(C)Nc1cnc(NC(=O)c2ccccc2OS(C)(=O)=O)s1] |

TABLE 7-continued

| No. | Structure |
|---|---|
| 36 | 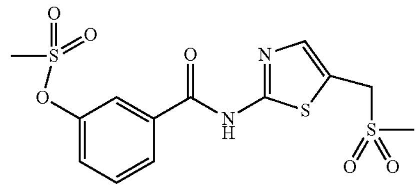 |
| 37 | 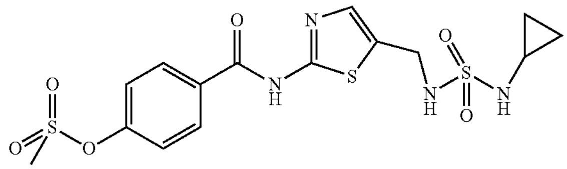 [SMILES: CS(=O)(=O)Oc1ccc(C(=O)Nc2ncc(CNS(=O)(=O)NC3CC3)s2)cc1] |
| 38 | 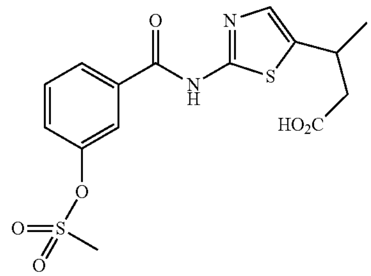 [SMILES: CC(CC(=O)O)c1cnc(NC(=O)c2cccc(OS(C)(=O)=O)c2)s1] |
| 39 | 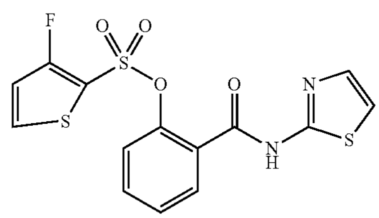 [SMILES: O=C(Nc1nccs1)c1ccccc1OS(=O)(=O)c1sccc1F] |
| 40 | 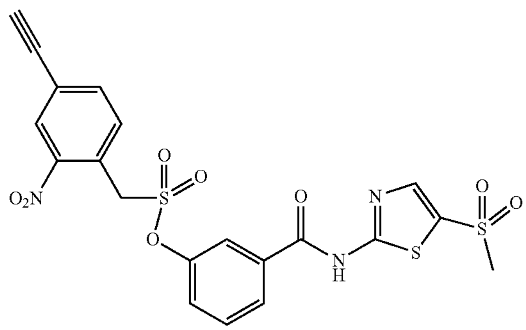 [SMILES: C#Cc1ccc(CS(=O)(=O)Oc2cccc(C(=O)Nc3ncc(S(C)(=O)=O)s3)c2)c([N+](=O)[O-])c1] |
| 41 | 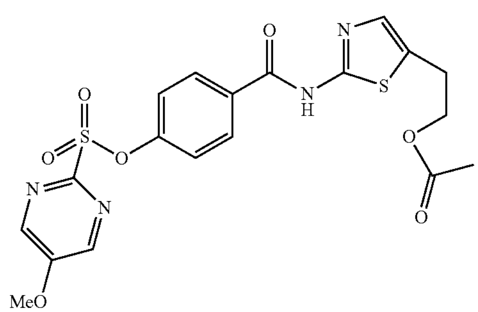 [SMILES: COc1cnc(S(=O)(=O)Oc2ccc(C(=O)Nc3ncc(CCOC(C)=O)s3)cc2)nc1] |

TABLE 7-continued

| No. | Structure |
|---|---|
| 42 | 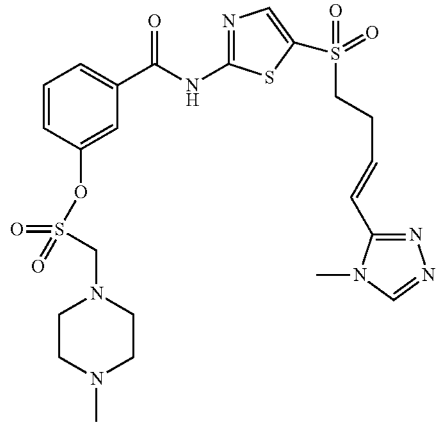 [SMILES: CN1CCN(CS(=O)(=O)Oc2cccc(C(=O)Nc3ncc(S(=O)(=O)CC/C=C/c4nncn4C)s3)c2)CC1] |
| 43 | 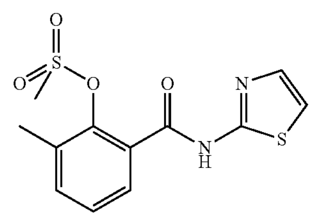 [SMILES: Cc1cccc(C(=O)Nc2nccs2)c1OS(C)(=O)=O] |
| 44 | 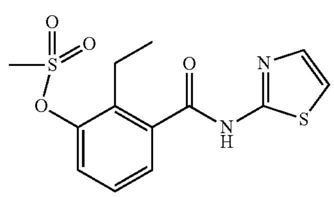 [SMILES: CCc1c(OS(C)(=O)=O)cccc1C(=O)Nc1nccs1] |
| 45 | 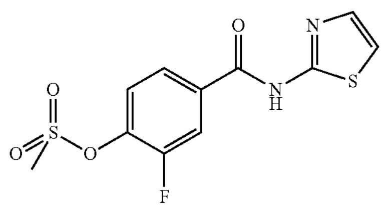 [SMILES: CS(=O)(=O)Oc1ccc(C(=O)Nc2nccs2)cc1F] |
| 46 | 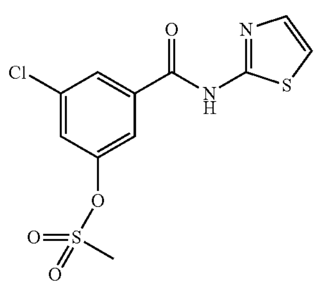 [SMILES: CS(=O)(=O)Oc1cc(Cl)cc(C(=O)Nc2nccs2)c1] |
| 47 | 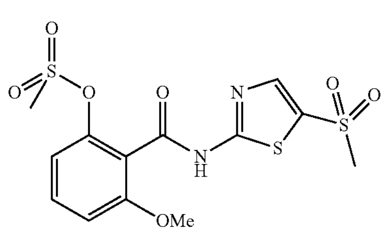 [SMILES: COc1cccc(OS(C)(=O)=O)c1C(=O)Nc1ncc(S(C)(=O)=O)s1] |

TABLE 7-continued
| No. | Structure |
|---|---|
| 48 | 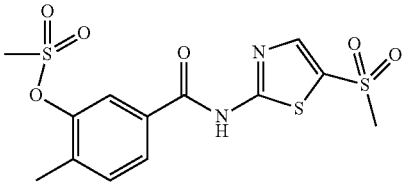 [SMILES: Cc1ccc(C(=O)Nc2ncc(S(C)(=O)=O)s2)cc1OS(C)(=O)=O] |
| 49 | 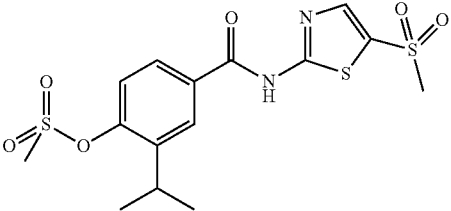 [SMILES: CC(C)c1cc(C(=O)Nc2ncc(S(C)(=O)=O)s2)ccc1OS(C)(=O)=O] |
| 50 | 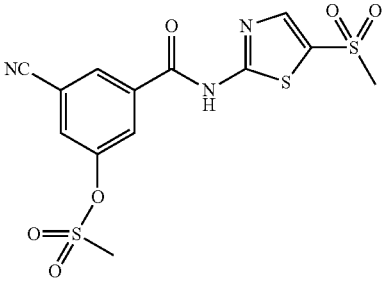 [SMILES: CS(=O)(=O)Oc1cc(C#N)cc(C(=O)Nc2ncc(S(C)(=O)=O)s2)c1] |
| 51 | 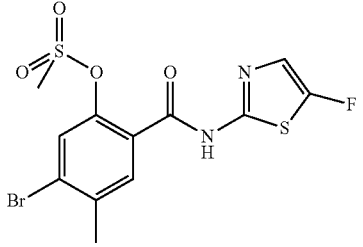 [SMILES: Cc1cc(C(=O)Nc2ncc(F)s2)c(OS(C)(=O)=O)cc1Br] |
| 52 | 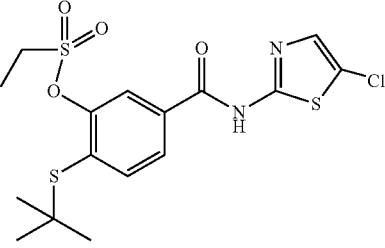 [SMILES: CCS(=O)(=O)Oc1cc(C(=O)Nc2ncc(Cl)s2)ccc1SC(C)(C)C] |
| 53 | 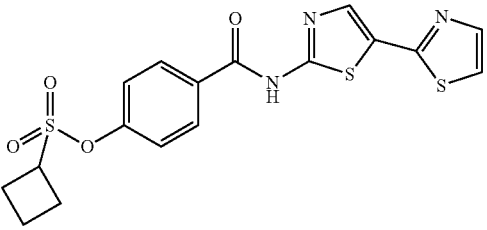 [SMILES: O=C(Nc1ncc(-c2nccs2)s1)c1ccc(OS(=O)(=O)C2CCC2)cc1] |

TABLE 7-continued
| No. | Structure |
|---|---|
| 54 | 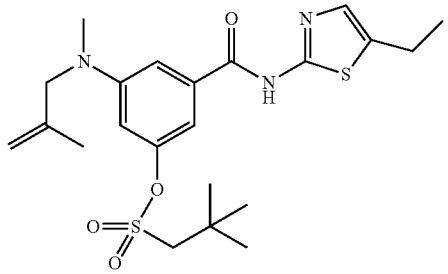 [SMILES: C=C(C)CN(C)c1cc(OS(=O)(=O)CC(C)(C)C)cc(C(=O)Nc2ncc(CC)s2)c1] |
| 55 | 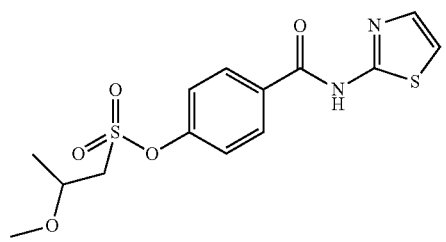 [SMILES: COC(C)CS(=O)(=O)Oc1ccc(C(=O)Nc2nccs2)cc1] |
| 56 | 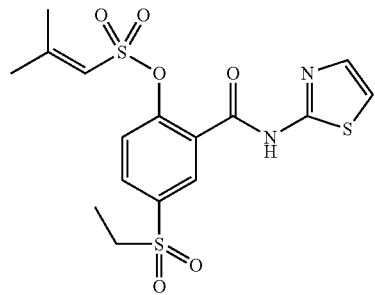 [SMILES: CCS(=O)(=O)c1ccc(OS(=O)(=O)C=C(C)C)c(C(=O)Nc2nccs2)c1] |
| 57 | 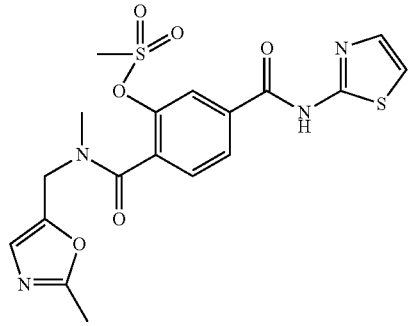 [SMILES: Cc1ncc(CN(C)C(=O)c2ccc(C(=O)Nc3nccs3)cc2OS(C)(=O)=O)o1] |
| 58 | 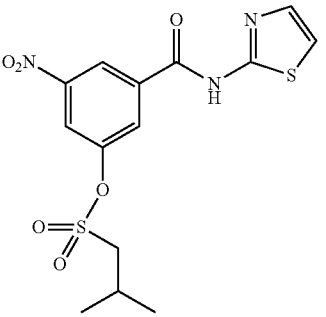 [SMILES: CC(C)CS(=O)(=O)Oc1cc(C(=O)Nc2nccs2)cc([N+](=O)[O-])c1] |

TABLE 7-continued

| No. | Structure |
|---|---|
| 59 | 2-hydroxy-3-methyl-N-(4-(methylsulfonyl)thiazol-2-yl)benzamide |
| 60 | 2-hydroxy-N-(4-(methylsulfonyl)thiazol-2-yl)benzamide |
| 61 | 2-acetoxy-3-methyl-N-(4-(methylsulfonyl)thiazol-2-yl)benzamide |
| 62 | 2-acetoxy-N-(4-(methylsulfonyl)thiazol-2-yl)benzamide |
| 63 | 2-methoxy-3-methyl-N-(4-(methylsulfonyl)thiazol-2-yl)benzamide |
| 64 | 2-methoxy-N-(4-(methylsulfonyl)thiazol-2-yl)benzamide |
| 65 | 2-hydroxy-3-methoxy-N-(4-(methylsulfonyl)thiazol-2-yl)benzamide |
| 66 | 2-hydroxy-5-methyl-N-(4-(methylsulfonyl)thiazol-2-yl)benzamide |

TABLE 7-continued

| No. | Structure |
|---|---|
| 67 | 2-carboxy-5-methyl-N-(4-(methylsulfonyl)thiazol-2-yl)benzamide |
| 68 | 2-hydroxy-4-methyl-N-(4-(methylsulfonyl)thiazol-2-yl)benzamide |
| 69 | 2-acetoxy-N-(5-(methylthio)thiazol-2-yl)benzamide |
| 70 | 2-hydroxy-N-(5-(methylthio)thiazol-2-yl)benzamide |
| 71 | 2-acetoxy-N-(5-(butylthio)thiazol-2-yl)benzamide |
| 72 | 2-hydroxy-N-(5-(butylthio)thiazol-2-yl)benzamide |
| 73 | 2-acetoxy-N-(5-(butylsulfonyl)thiazol-2-yl)benzamide |
| 74 | 2-hydroxy-N-(5-(butylsulfonyl)thiazol-2-yl)benzamide |
| 75 | sodium 2-((5-(methylsulfonyl)thiazol-2-yl)carbamoyl)phenolate |

TABLE 7-continued

| No. | Structure |
|-----|-----------|
| 76 | 4-acetoxy-N-(5-(methylthio)thiazol-2-yl)benzamide |
| 77 | 3-acetoxy-N-(5-(methylthio)thiazol-2-yl)benzamide |
| 78 | 4-acetoxy-N-(5-(methylsulfonyl)thiazol-2-yl)benzamide |
| 79 | 3-acetoxy-N-(5-(methylsulfonyl)thiazol-2-yl)benzamide |
| 80 | 4-hydroxy-N-(5-(methylsulfonyl)thiazol-2-yl)benzamide |
| 81 | 3-hydroxy-N-(5-(methylsulfonyl)thiazol-2-yl)benzamide |
| 82 | 4-acetoxy-N-(4-(methylthio)thiazol-2-yl)benzamide |
| 83 | 4-acetoxy-N-(4-(methylsulfonyl)thiazol-2-yl)benzamide |

TABLE 7-continued

| No. | Structure |
|---|---|
| 84 | 4-hydroxy-N-(4-(methylsulfonyl)thiazol-2-yl)benzamide |
| 85 | 3-(N-(4-(methylthio)thiazol-2-yl)carbamoyl)phenyl acetate |
| 86 | 3-(N-(4-(methylsulfonyl)thiazol-2-yl)carbamoyl)phenyl acetate |
| 87 | 3-hydroxy-N-(4-(methylsulfonyl)thiazol-2-yl)benzamide |
| 88 | 2-hydroxy-N-(4-methyl-5-(methylsulfonyl)thiazol-2-yl)benzamide |
| 89 | N-(4-chloro-5-(methylsulfonyl)thiazol-2-yl)-2-hydroxybenzamide |
| 90 | 3-ethyl-2-hydroxy-N-(5-(methylsulfonyl)thiazol-2-yl)benzamide |

TABLE 7-continued

| No. | Structure |
|-----|-----------|
| 91 | 2-hydroxy-4-(trifluoromethyl)-N-(5-(ethylsulfonyl)thiazol-2-yl)benzamide |
| 92 | 4-chloro-2-hydroxy-N-(5-((methylsulfonyl)methyl)thiazol-2-yl)benzamide |
| 93 | 5-chloro-2-hydroxy-N-(5-(isopropylsulfonyl)thiazol-2-yl)benzamide |
| 94 | 3-bromo-2-hydroxy-N-(5-(cyclopropylsulfonyl)-4-methylthiazol-2-yl)benzamide |
| 95 | 3,5-dibromo-2-hydroxy-N-(4-chloro-5-(methylsulfonyl)thiazol-2-yl)benzamide |
| 96 | 3-chloro-2-hydroxy-N-(5-((4-methyloxazol-2-yl)sulfonyl)thiazol-2-yl)benzamide |
| 97 | 3-fluoro-2-hydroxy-N-(5-(phenylsulfonyl)thiazol-2-yl)benzamide |
| 98 | N-(5-(benzylsulfonyl)thiazol-2-yl)-5-chloro-2-hydroxy-4-methylbenzamide |

TABLE 7-continued
| No. | Structure |
|---|---|
| 99 | 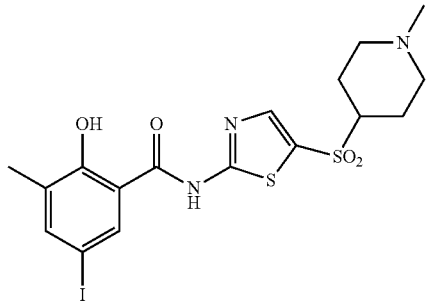 [SMILES: Cc1cc(I)cc(C(=O)Nc2ncc(S(=O)(=O)C3CCN(C)CC3)s2)c1O] |
| 100 | 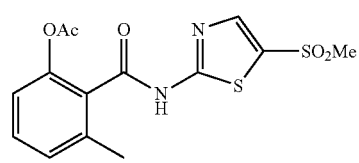 [SMILES: CC(=O)Oc1cccc(C)c1C(=O)Nc1ncc(S(C)(=O)=O)s1] |
| 101 | 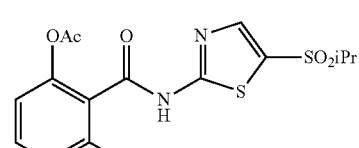 |
| 102 | 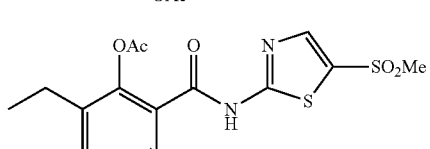 |
| 103 | 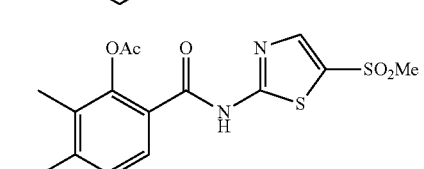 |
| 104 | 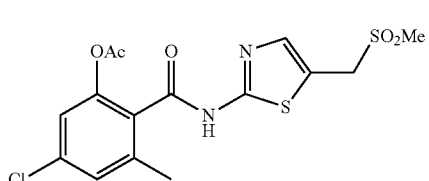 |
| 105 | 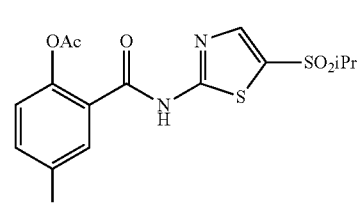 |
| 106 | 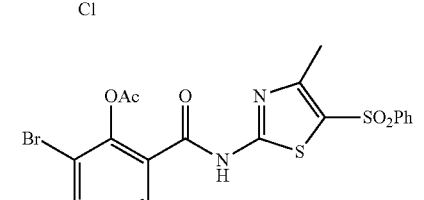 |

TABLE 7-continued
| No. | Structure |
|---|---|
| 107 | 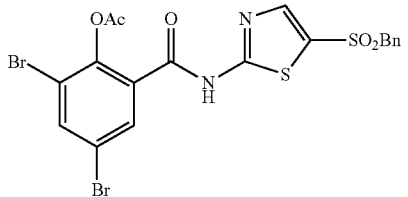 |
| 108 | 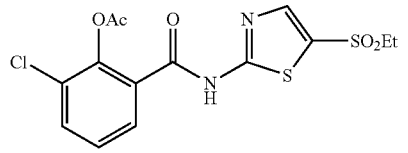 |
| 109 | 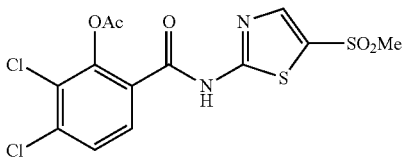 [SMILES: CC(=O)Oc1c(C(=O)Nc2ncc(S(C)(=O)=O)s2)ccc(Cl)c1Cl] |
| 110 | 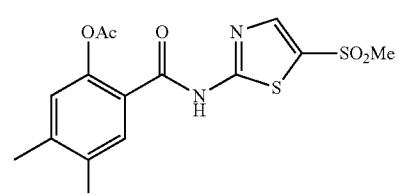 |
| 111 | 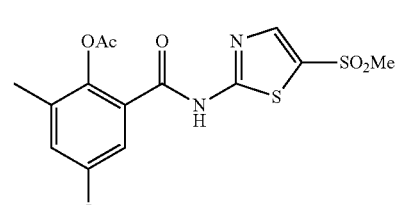 |
| 112 | 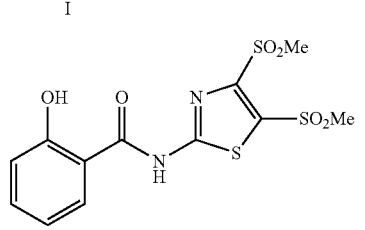 |
| 113 | 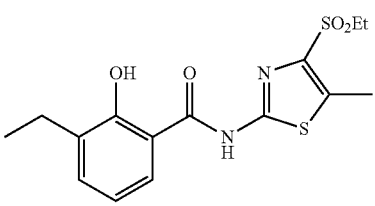 |
| 114 | 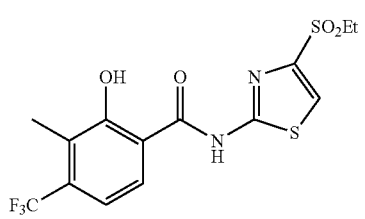 |

TABLE 7-continued

| No. | Structure |
|---|---|
| 115 | 4-chloro-2-hydroxy-N-(5-ethyl-4-(isopropylsulfonyl)thiazol-2-yl)benzamide |
| 116 | 5-chloro-N-(4-((cyclobutylmethylsulfonyl))thiazol-2-yl)-2-hydroxybenzamide |
| 117 | 3-bromo-2-hydroxy-N-(4-(methylsulfonyl)thiazol-2-yl)benzamide |
| 118 | 3,5-dibromo-2-hydroxy-N-(4-(methylsulfonyl)thiazol-2-yl)benzamide |
| 119 | N-(4-(tert-butylsulfonyl)-5-fluorothiazol-2-yl)-3-chloro-2-hydroxybenzamide |
| 120 | 4-chloro-N-(5-cyano-4-(propylsulfonyl)thiazol-2-yl)-3-fluoro-2-hydroxybenzamide |

TABLE 7-continued

| No. | Structure |
| --- | --- |
| 121 | 5-chloro-2-hydroxy-4-methyl-N-(4-((6-methylpyridin-2-yl)sulfonyl)thiazol-2-yl)benzamide |
| 122 | 2-hydroxy-5-iodo-3-methyl-N-(4-(methylsulfonyl)thiazol-2-yl)benzamide |
| 123 | 2-(methylsulfonyl)thiazol-2-ylcarbamoyl)-3,5-dimethylphenyl acetate |
| 124 | 2-((4,5-bis(methylsulfonyl)thiazol-2-yl)carbamoyl)-1,3-phenylene diacetate |
| 125 | 3-ethyl-2-((5-methyl-4-(methylsulfonyl)thiazol-2-yl)carbamoyl)phenyl acetate |
| 126 | 3-methyl-2-((4-(methylsulfonyl)thiazol-2-yl)carbamoyl)-4-(trifluoromethyl)phenyl acetate |
| 127 | 5-chloro-3-methyl-2-((4-(methylsulfonyl)thiazol-2-yl)carbamoyl)phenyl acetate |

TABLE 7-continued

| No. | Structure |
|-----|-----------|
| 128 | 2-acetoxy-5-chloro-N-(4-((5-nitrothiazol-2-yl)sulfonyl)thiazol-2-yl)benzamide |
| 129 | 2-acetoxy-3-bromo-N-(4-(styrylsulfonyl)thiazol-2-yl)benzamide |
| 130 | 2-acetoxy-3,5-dibromo-N-(4-(isopentylsulfonyl)thiazol-2-yl)benzamide |
| 131 | 2-acetoxy-3-chloro-N-(4-(ethylsulfonyl)thiazol-2-yl)benzamide |
| 132 | 2-acetoxy-3,4-dichloro-N-(4-(methylsulfonyl)thiazol-2-yl)benzamide |
| 133 | 2-acetoxy-4-chloro-5-methyl-N-(4-(ethylsulfonyl)thiazol-2-yl)benzamide |

TABLE 7-continued

| No. | Structure |
|---|---|
| 134 | 2-OAc-3-methyl-5-iodo-N-(4-(methylsulfonyl)thiazol-2-yl)benzamide |
| 135 | 3-hydroxy-N-(5-(methylsulfonyl)thiazol-2-yl)benzamide |
| 136 | 3-hydroxy-2-methyl-N-(5-(methylsulfonyl)thiazol-2-yl)benzamide |
| 137 | 2-ethyl-3-hydroxy-N-(5-(methylsulfonyl)thiazol-2-yl)benzamide |
| 138 | N-(5-(ethylsulfonyl)thiazol-2-yl)-3-hydroxy-2-methyl-4-(trifluoromethoxy)benzamide |
| 139 | 4-chloro-N-(5-((ethylsulfonyl)methyl)thiazol-2-yl)-3-hydroxy-2-methylbenzamide |
| 140 | 3-chloro-5-hydroxy-N-(5-(isopropylsulfonyl)thiazol-2-yl)benzamide |
| 141 | 2-bromo-3-hydroxy-N-(5-((tetrahydro-2H-pyran-4-yl)sulfonyl)thiazol-2-yl)benzamide |

TABLE 7-continued
| No. | Structure |
|---|---|
| 142 | 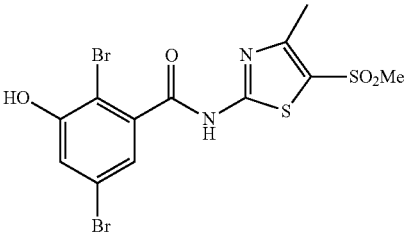 |
| 143 | 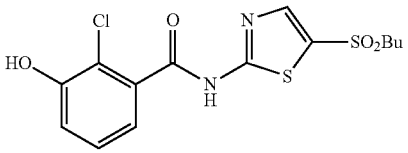 [SMILES: Cc1c(O)cccc1C(=O)Nc1ncc(S(C)(=O)=O)s1] |
| 144 | 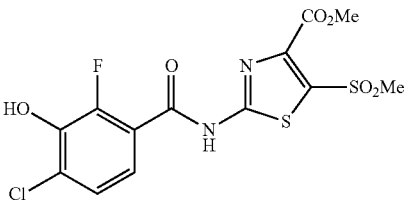 [SMILES: COC(=O)c1nc(NC(=O)c2ccc(Cl)c(O)c2F)sc1S(C)(=O)=O] |
| 145 | 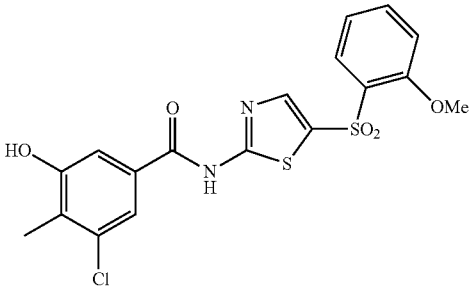 [SMILES: COc1ccccc1S(=O)(=O)c1cnc(NC(=O)c2cc(O)c(C)c(Cl)c2)s1] |
| 146 | 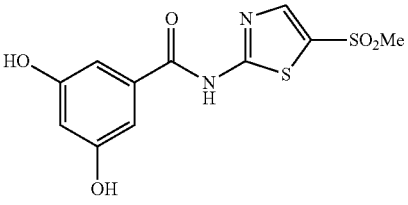 [SMILES: CS(=O)(=O)c1cnc(NC(=O)c2cc(O)cc(O)c2)s1] |
| 147 | 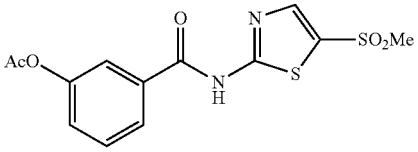 [SMILES: CC(=O)Oc1cccc(C(=O)Nc2ncc(S(C)(=O)=O)s2)c1] |
| 148 | 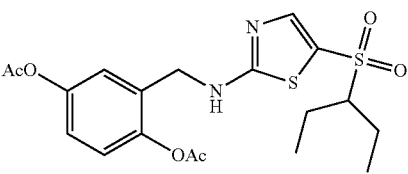 [SMILES: CCC(CC)S(=O)(=O)c1cnc(NCc2cc(OC(C)=O)ccc2OC(C)=O)s1] |

TABLE 7-continued
| No. | Structure |
|---|---|
| 149 | 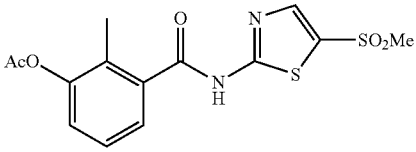 [SMILES: CC(=O)Oc1cccc(C(=O)Nc2ncc(S(C)(=O)=O)s2)c1C] |
| 150 | 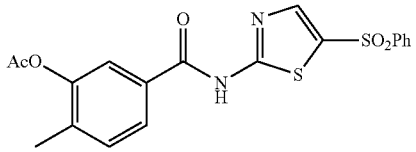 |
| 151 | 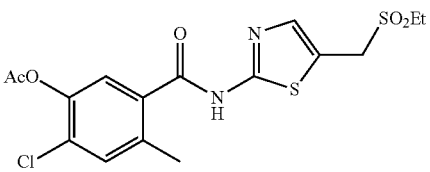 |
| 152 | 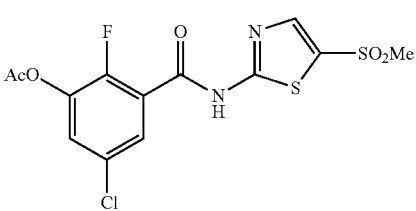 [SMILES: CC(=O)Oc1cc(Cl)cc(C(=O)Nc2ncc(S(C)(=O)=O)s2)c1F] |
| 153 | 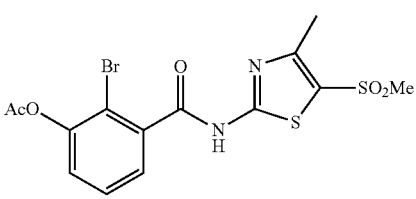 [SMILES: CC(=O)Oc1cccc(C(=O)Nc2nc(C)c(S(C)(=O)=O)s2)c1Br] |
| 154 | 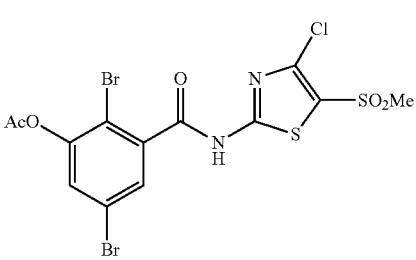 [SMILES: CC(=O)Oc1cc(Br)cc(C(=O)Nc2nc(Cl)c(S(C)(=O)=O)s2)c1Br] |
| 155 | 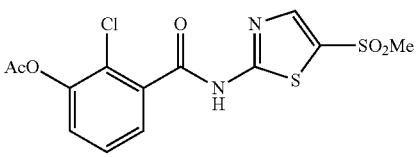 [SMILES: CC(=O)Oc1cccc(C(=O)Nc2ncc(S(C)(=O)=O)s2)c1Cl] |
| 156 | 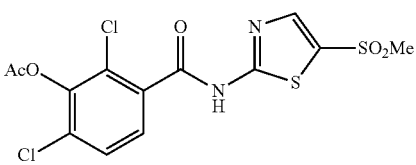 [SMILES: CC(=O)Oc1c(Cl)ccc(C(=O)Nc2ncc(S(C)(=O)=O)s2)c1Cl] |

TABLE 7-continued

| No. | Structure |
|---|---|
| 157 | 3-AcO-5-Cl-C6H3-C(O)NH-thiazole-5-CH2CH2-SO2Me |
| 158 | 3-AcO-5-I-C6H3-C(O)NH-thiazole-5-SO2Me |
| 159 | 3-HO-C6H4-C(O)NH-thiazole-4-SO2Me |
| 160 | 3-HO-2-Me-C6H3-C(O)NH-thiazole-4-SO2Me |
| 161 | 3-HO-2-Et-C6H3-C(O)NH-thiazole-4-SO2Me |
| 162 | 3-HO-2-Me-4-(OCF3)-C6H2-C(O)NH-thiazole-4-SO2Et |
| 163 | 3-HO-2-Me-4-Cl-C6H2-C(O)NH-thiazole-4-CH2-SO2Et |

TABLE 7-continued

| No. | Structure |
|---|---|
| 164 | 3-chloro-5-hydroxy-N-(4-(isopropylsulfonyl)thiazol-2-yl)benzamide |
| 165 | 2-bromo-3-hydroxy-N-(4-((tetrahydro-2H-pyran-4-yl)sulfonyl)thiazol-2-yl)benzamide |
| 166 | 2,5-dibromo-3-hydroxy-N-(4-(methylsulfonyl)thiazol-2-yl)benzamide |
| 167 | N-(4-(butylsulfonyl)thiazol-2-yl)-2-chloro-3-hydroxybenzamide |
| 168 | 4-chloro-2-fluoro-3-hydroxy-N-(4-(methylsulfonyl)thiazol-2-yl)benzamide |
| 169 | 3-chloro-5-hydroxy-N-(4-((2-methoxyphenyl)sulfonyl)thiazol-2-yl)-4-methylbenzamide |

TABLE 7-continued

| No. | Structure |
|-----|-----------|
| 170 | 3,5-dihydroxy-N-(4-(methylsulfonyl)thiazol-2-yl)benzamide |
| 171 | 3-acetoxy-N-(4-(methylsulfonyl)thiazol-2-yl)benzamide |
| 172 | 2,5-diacetoxy-N-(4-(pentan-3-ylsulfonyl)thiazol-2-yl)benzamide |
| 173 | 3-acetoxy-2-methyl-N-(4-(methylsulfonyl)thiazol-2-yl)benzamide |
| 174 | 3-acetoxy-4-methyl-N-(4-(phenylsulfonyl)thiazol-2-yl)benzamide |
| 175 | 5-acetoxy-4-chloro-N-(4-((ethylsulfonyl)methyl)thiazol-2-yl)-2-methylbenzamide |
| 176 | 3-acetoxy-5-chloro-2-fluoro-N-(4-(methylsulfonyl)thiazol-2-yl)benzamide |

TABLE 7-continued

| No. | Structure |
|---|---|
| 177 | 2-bromo-3-acetoxy-N-(4-(methylsulfonyl)thiazol-2-yl)benzamide |
| 178 | 2,5-dibromo-3-acetoxy-N-(4-(methylsulfonyl)thiazol-2-yl)benzamide |
| 179 | 2-chloro-3-acetoxy-N-(4-(methylsulfonyl)thiazol-2-yl)benzamide |
| 180 | 2,4-dichloro-3-acetoxy-N-(4-(methylsulfonyl)thiazol-2-yl)benzamide |
| 181 | 3-acetoxy-5-chloro-N-(4-(2-(methylsulfonyl)ethyl)thiazol-2-yl)benzamide |
| 182 | 3-acetoxy-5-iodo-N-(4-(methylsulfonyl)thiazol-2-yl)benzamide |
| 183 | 4-hydroxy-N-(5-(methylsulfonyl)thiazol-2-yl)benzamide |

TABLE 7-continued

| No. | Structure |
|---|---|
| 184 | 2-methyl-4-hydroxy-N-(5-(methylsulfonyl)thiazol-2-yl)benzamide |
| 185 | 3-methyl-4-hydroxy-N-(5-(methylsulfonyl)thiazol-2-yl)benzamide |
| 186 | 2-methyl-4-hydroxy-5-(trifluoromethoxy)-N-(5-(ethylsulfonyl)thiazol-2-yl)benzamide |
| 187 | 2-methyl-4-hydroxy-5-chloro-N-(5-((ethylsulfonyl)methyl)thiazol-2-yl)benzamide |
| 188 | 4-hydroxy-3-ethyl-N-(5-(isopropylsulfonyl)thiazol-2-yl)benzamide |
| 189 | 2-bromo-4-hydroxy-N-(5-((tetrahydro-2H-pyran-4-yl)sulfonyl)thiazol-2-yl)benzamide |
| 190 | 2,4-dihydroxy-5-bromo-N-(4-methyl-5-(methylsulfonyl)thiazol-2-yl)benzamide |

TABLE 7-continued

| No. | Structure |
|---|---|
| 191 | 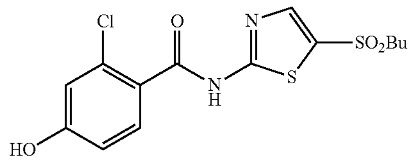 [SMILES: Cc1cc(O)ccc1C(=O)Nc1ncc(S(C)(=O)=O)s1] |
| 192 | 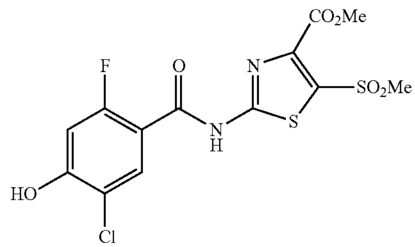 [SMILES: COC(=O)c1nc(NC(=O)c2cc(Cl)c(O)cc2F)sc1S(C)(=O)=O] |
| 193 | 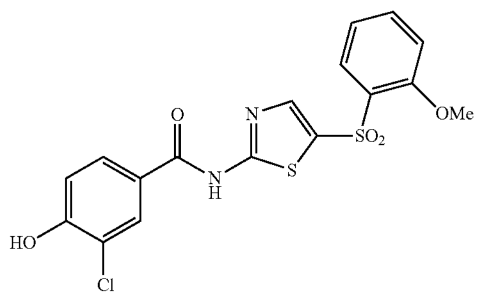 [SMILES: COc1ccccc1S(=O)(=O)c1cnc(NC(=O)c2ccc(O)c(Cl)c2)s1] |
| 194 | 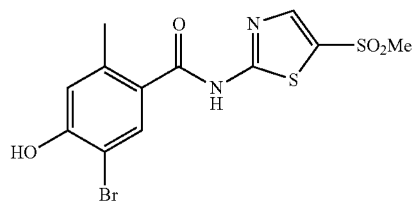 [SMILES: Cc1cc(O)c(Br)cc1C(=O)Nc1ncc(S(C)(=O)=O)s1] |
| 195 | 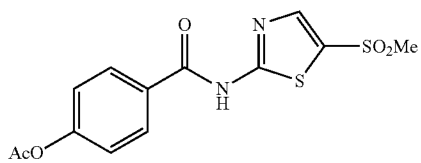 [SMILES: CC(=O)Oc1ccc(C(=O)Nc2ncc(S(C)(=O)=O)s2)cc1] |
| 196 | 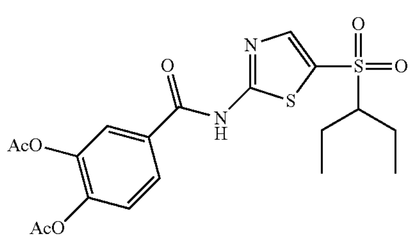 [SMILES: CCC(CC)S(=O)(=O)c1cnc(NC(=O)c2ccc(OC(C)=O)c(OC(C)=O)c2)s1] |
| 197 | 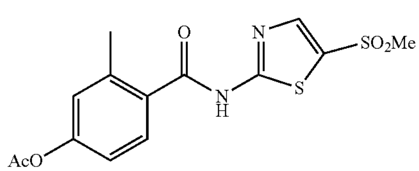 [SMILES: CC(=O)Oc1ccc(C(=O)Nc2ncc(S(C)(=O)=O)s2)c(C)c1] |

TABLE 7-continued

| No. | Structure |
|---|---|
| 198 | 4-AcO-C6H4-C(O)NH-(thiazol-2-yl)-5-SO2Ph |
| 199 | 4-AcO-3-Cl-2-Me-C6H2-C(O)NH-(thiazol-2-yl)-5-CH2SO2Et |
| 200 | 4-AcO-5-Cl-2-F-C6H2-C(O)NH-(thiazol-2-yl)-5-SO2Me |
| 201 | 4-AcO-2-Br-C6H3-C(O)NH-(4-methylthiazol-2-yl)-5-SO2Me |
| 202 | 4-AcO-2,5-diBr-C6H2-C(O)NH-(4-chlorothiazol-2-yl)-5-SO2Me |
| 203 | 4-AcO-2-Cl-C6H3-C(O)NH-(thiazol-2-yl)-5-SO2Me |
| 204 | 4-AcO-2,5-diCl-C6H2-C(O)NH-(thiazol-2-yl)-5-SO2Me |

TABLE 7-continued

| No. | Structure |
|---|---|
| 205 | 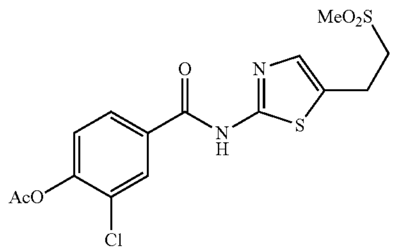 [SMILES: CC(=O)Oc1ccc(C(=O)Nc2ncc(CCS(C)(=O)=O)s2)cc1Cl] |
| 206 | 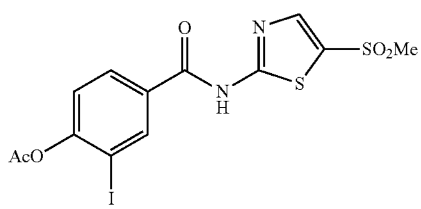 [SMILES: CC(=O)Oc1ccc(C(=O)Nc2ncc(S(C)(=O)=O)s2)cc1I] |
| 207 | 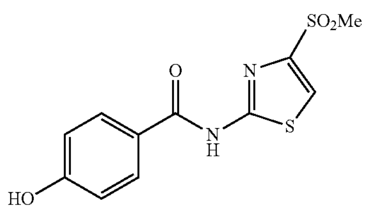 [SMILES: CS(=O)(=O)c1csc(NC(=O)c2ccc(O)cc2)n1] |
| 208 | 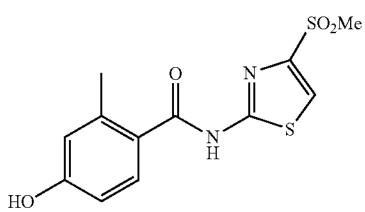 [SMILES: Cc1cc(O)ccc1C(=O)Nc1nc(S(C)(=O)=O)cs1] |
| 209 | 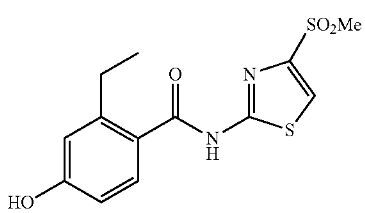 [SMILES: CCc1cc(O)ccc1C(=O)Nc1nc(S(C)(=O)=O)cs1] |
| 210 | 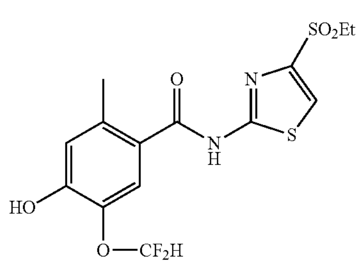 |

TABLE 7-continued
| No. | Structure |
|---|---|
| 211 | 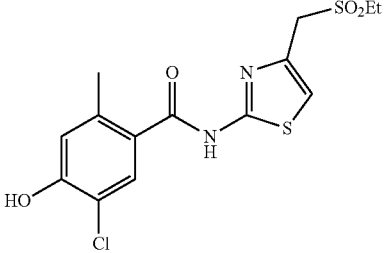 |
| 212 | 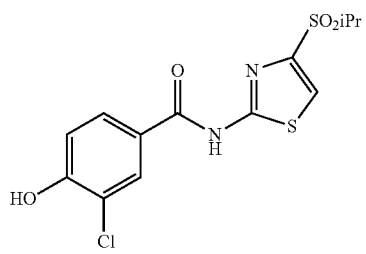 |
| 213 | 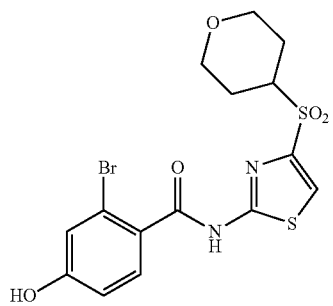 [SMILES: O=C(Nc1nc(S(=O)(=O)C2CCOCC2)cs1)c1ccc(O)cc1Br] |
| 214 | 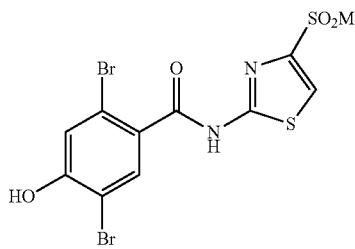 |
| 215 | 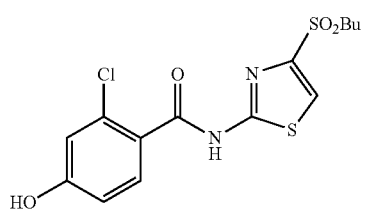 |
| 216 | 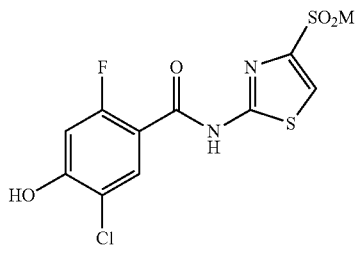 |

TABLE 7-continued

| No. | Structure |
|---|---|
| 217 | (structure) |
| 218 | (structure) |
| 219 | (structure) |
| 220 | (structure) |
| 221 | (structure) |
| 222 | (structure) |

TABLE 7-continued
| No. | Structure |
|---|---|
| 223 | 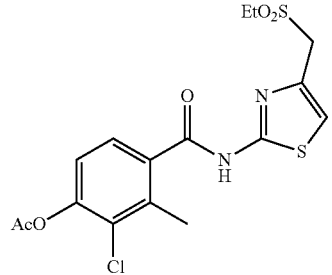 |
| 224 | 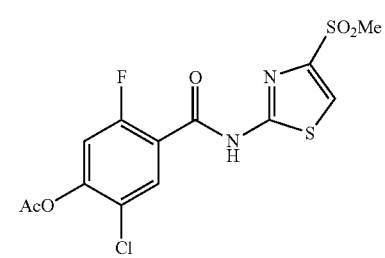 [SMILES: CC(=O)Oc1cc(F)c(C(=O)Nc2nc(S(C)(=O)=O)cs2)cc1Cl] |
| 225 | 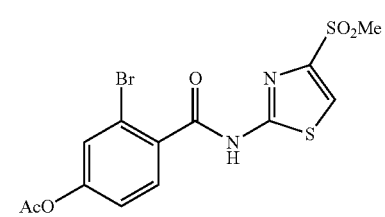 [SMILES: CC(=O)Oc1ccc(C(=O)Nc2nc(S(C)(=O)=O)cs2)c(Br)c1] |
| 226 | 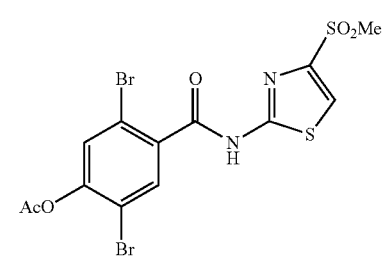 [SMILES: CC(=O)Oc1cc(Br)c(C(=O)Nc2nc(S(C)(=O)=O)cs2)cc1Br] |
| 227 | 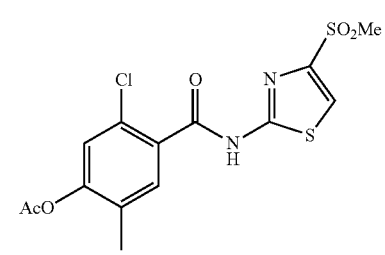 [SMILES: CC(=O)Oc1cc(Cl)c(C(=O)Nc2nc(S(C)(=O)=O)cs2)cc1C] |
| 228 | 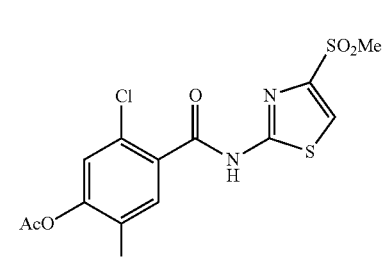 |

TABLE 7-continued

| No. | Structure |
|---|---|
| 229 | 4-AcO, 3-Cl-C6H3-C(O)NH-thiazole (2-yl), 4-(CH2CH2SO2Me) |
| 230 | 4-AcO, 3-I-C6H3-C(O)NH-thiazole (2-yl), 4-SO2Me |
| 231 | 2-OH-C6H4-C(O)NH-thiazole (2-yl), 5-NHSO2Me |
| 232 | 2-OH-C6H4-C(O)NH-thiazole (2-yl), 4-Cl, 5-NHSO2Me |
| 233 | 2-OH, 3-Et-C6H3-C(O)NH-thiazole (2-yl), 5-NHSO2Me |
| 234 | 2-OH, 4-CF3-C6H3-C(O)NH-thiazole (2-yl), 5-NHSO2Me |
| 235 | 2-OH, 4-Cl-C6H3-C(O)NH-thiazole (2-yl), 5-CH2NHSO2Me |

TABLE 7-continued

| No. | Structure |
|---|---|
| 236 | 5-chloro-2-hydroxy-N-(5-(methylsulfonamido)thiazol-2-yl)benzamide |
| 237 | 2-hydroxy-N-(4-(methylsulfonamido)thiazol-2-yl)benzamide |
| 238 | 5-bromo-2-hydroxy-N-(4-(methylsulfonamido)thiazol-2-yl)benzamide |
| 239 | 3-chloro-2-hydroxy-N-(5-methyl-4-(methylsulfonamido)thiazol-2-yl)benzamide |
| 240 | N-(5-chloro-4-(methylsulfonamido)thiazol-2-yl)-3-fluoro-2-hydroxybenzamide |
| 241 | 5-chloro-2-hydroxy-4-methyl-N-(5-methyl-4-(methylsulfonamido)thiazol-2-yl)benzamide |
| 242 | 2-hydroxy-5-iodo-3-methyl-N-(5-methyl-4-(methylsulfonamido)thiazol-2-yl)benzamide |

TABLE 7-continued

| No. | Structure |
|-----|-----------|
| 243 | 2-OAc, 6-methyl benzamide-N-(5-(NHSO₂Me)thiazol-2-yl) |
| 244 | 2,6-di-OAc benzamide-N-(5-(NHSO₂Me)thiazol-2-yl) |
| 244 | 2,6-di-OAc benzamide-N-(5-(NHSO₂Me)thiazol-2-yl) |
| 245 | 2-OAc, 3-ethyl benzamide-N-(5-(NHSO₂Me)thiazol-2-yl) |
| 246 | 2-OAc, 3-methyl, 4-CF₃ benzamide-N-(5-(NHSO₂Me)thiazol-2-yl) |
| 247 | 2-OAc, 4-Cl, 6-methyl benzamide-N-(5-(CH₂NHSO₂Me)thiazol-2-yl) |
| 248 | 2-OAc, 5-Cl benzamide-N-(5-(NHSO₂Me)thiazol-2-yl) |
| 249 | 2-OAc, 3-Br benzamide-N-(4-(NHSO₂Me)thiazol-2-yl) |

TABLE 7-continued

| No. | Structure |
|---|---|
| 250 | 3,5-dibromo-2-acetoxy-N-(4-(methylsulfonamido)thiazol-2-yl)benzamide |
| 251 | 3-chloro-2-acetoxy-N-(4-(methylsulfonamido)thiazol-2-yl)benzamide |
| 252 | 3,4-dichloro-2-acetoxy-N-(5-ethyl-4-(methylsulfonamido)thiazol-2-yl)benzamide |
| 253 | 2-acetoxy-5-chloro-4-methyl-N-(5-fluoro-4-(methylsulfonamido)thiazol-2-yl)benzamide |
| 254 | 2-acetoxy-5-iodo-3-methyl-N-(4-(methylsulfonamido)-5-(trifluoromethyl)thiazol-2-yl)benzamide |
| 255 | 2-(propanoyloxy)-N-(5-(methylsulfonyl)thiazol-2-yl)benzamide |
| 256 | 2-(pentanoyloxy)-N-(4-(methylsulfonyl)thiazol-2-yl)benzamide |

TABLE 7-continued

| No. | Structure |
|---|---|
| 257 | 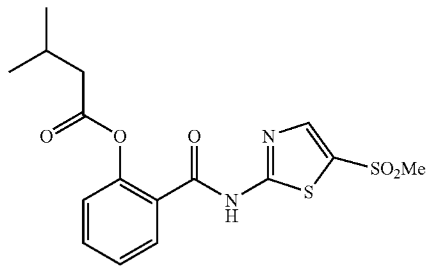 |
| 258 | 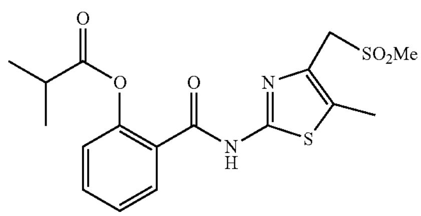 [SMILES: Cc1sc(NC(=O)c2ccccc2OC(=O)C(C)C)nc1CS(C)(=O)=O] |
| 259 | 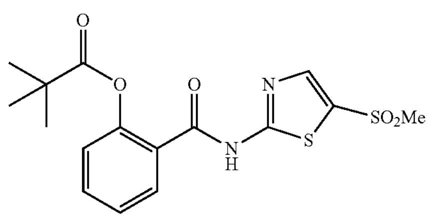 [SMILES: CC(C)(C)C(=O)Oc1ccccc1C(=O)Nc1ncc(S(C)(=O)=O)s1] |
| 260 | 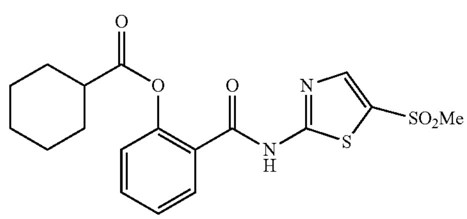 [SMILES: CS(=O)(=O)c1cnc(NC(=O)c2ccccc2OC(=O)C2CCCCC2)s1] |
| 261 | 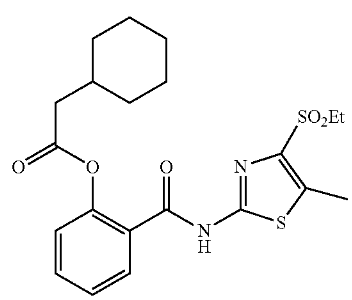 |
| 262 | 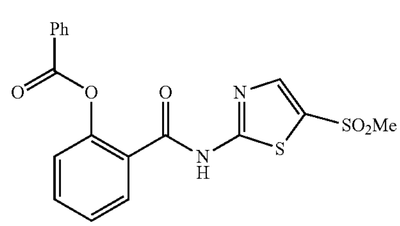 [SMILES: CS(=O)(=O)c1cnc(NC(=O)c2ccccc2OC(=O)c2ccccc2)s1] |

TABLE 7-continued

| No. | Structure |
|---|---|
| 263 | 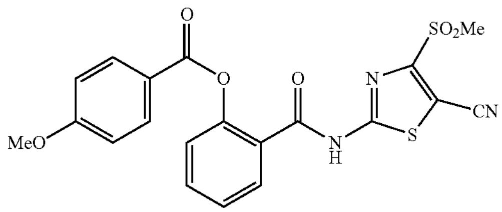 [SMILES: COc1ccc(C(=O)Oc2ccccc2C(=O)Nc2nc(S(C)(=O)=O)c(C#N)s2)cc1] |
| 264 | 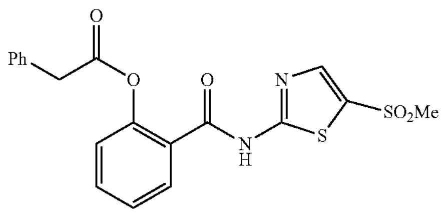 [SMILES: CS(=O)(=O)c1cnc(NC(=O)c2ccccc2OC(=O)Cc2ccccc2)s1] |
| 265 | 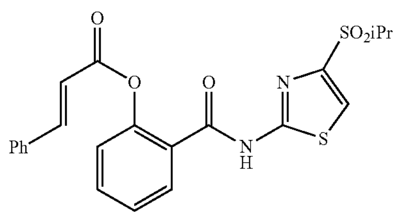 |
| 266 | 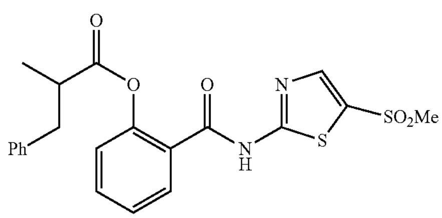 [SMILES: CC(Cc1ccccc1)C(=O)Oc1ccccc1C(=O)Nc1ncc(S(C)(=O)=O)s1] |
| 267 | 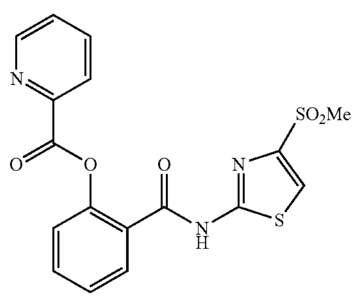 [SMILES: CS(=O)(=O)c1csc(NC(=O)c2ccccc2OC(=O)c2ccccn2)n1] |
| 268 | 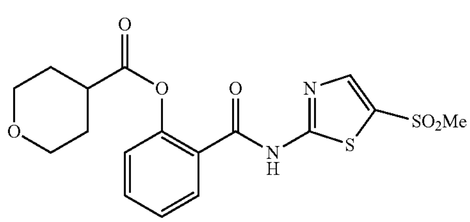 [SMILES: CS(=O)(=O)c1cnc(NC(=O)c2ccccc2OC(=O)C2CCOCC2)s1] |
| 269 | 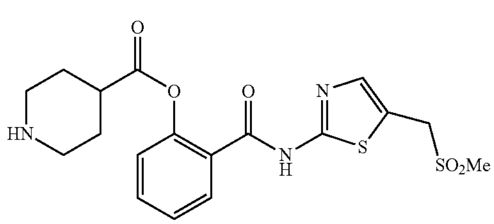 [SMILES: CS(=O)(=O)Cc1cnc(NC(=O)c2ccccc2OC(=O)C2CCNCC2)s1] |

TABLE 7-continued

| No. | Structure |
|---|---|
| 270 | 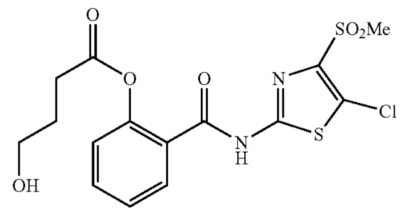 [SMILES: CS(=O)(=O)c1nc(NC(=O)c2ccccc2OC(=O)CCCO)sc1Cl] |
| 271 | 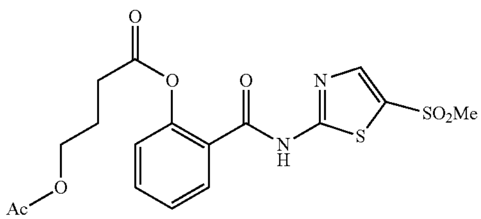 [SMILES: CC(=O)OCCCC(=O)Oc1ccccc1C(=O)Nc1ncc(S(C)(=O)=O)s1] |
| 272 | 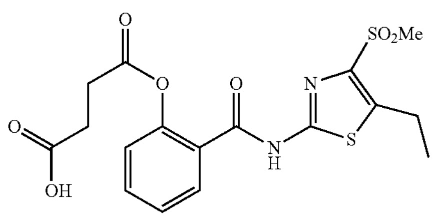 [SMILES: CCc1sc(NC(=O)c2ccccc2OC(=O)CCC(=O)O)nc1S(C)(=O)=O] |
| 273 | 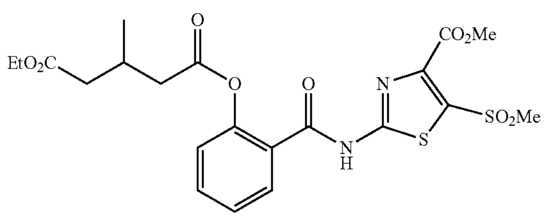 [SMILES: CCOC(=O)CC(C)CC(=O)Oc1ccccc1C(=O)Nc1nc(C(=O)OC)c(S(C)(=O)=O)s1] |
| 274 | 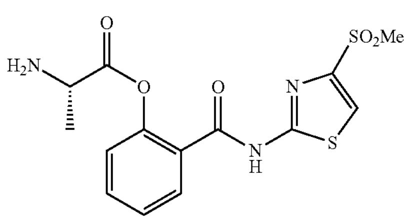 [SMILES: C[C@H](N)C(=O)Oc1ccccc1C(=O)Nc1nc(S(C)(=O)=O)cs1] |
| 275 | 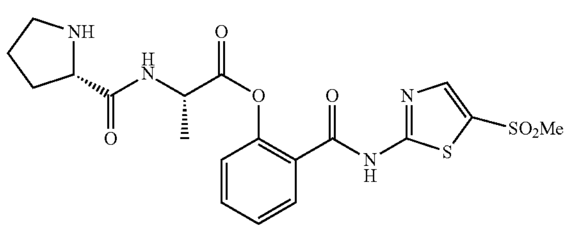 [SMILES: C[C@H](NC(=O)[C@@H]1CCCN1)C(=O)Oc1ccccc1C(=O)Nc1ncc(S(C)(=O)=O)s1] |
| 276 | 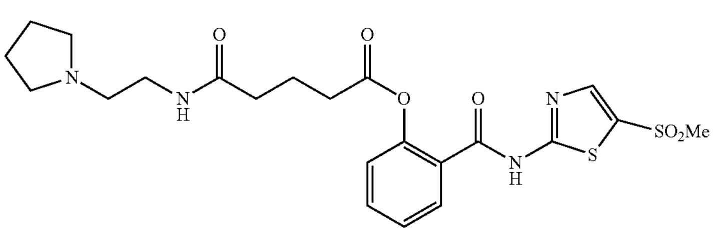 [SMILES: CS(=O)(=O)c1cnc(NC(=O)c2ccccc2OC(=O)CCCC(=O)NCCN2CCCC2)s1] |

TABLE 7-continued
| No. | Structure |
|---|---|
| 277 | 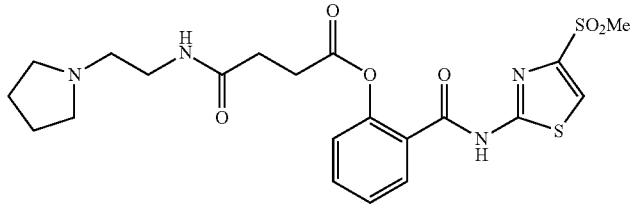 [SMILES: CS(=O)(=O)c1csc(NC(=O)c2ccccc2OC(=O)CCC(=O)NCCN2CCCC2)n1] |
| 278 | 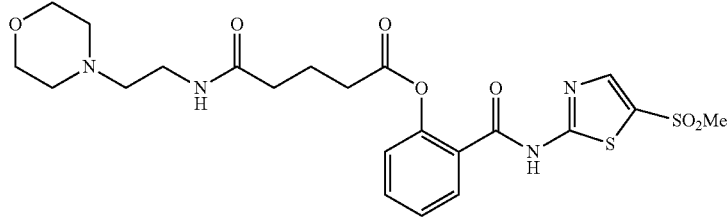 [SMILES: CS(=O)(=O)c1cnc(NC(=O)c2ccccc2OC(=O)CCCC(=O)NCCN2CCOCC2)s1] |
| 279 | 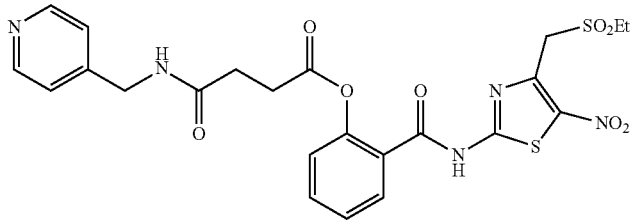 |
| 280 | 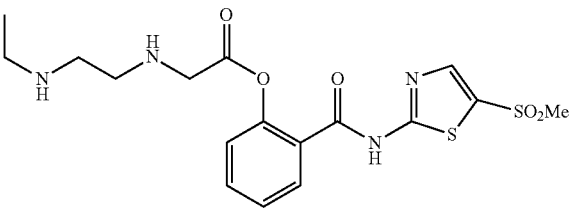 [SMILES: CCNCCNCC(=O)Oc1ccccc1C(=O)Nc1ncc(S(C)(=O)=O)s1] |
| 281 | 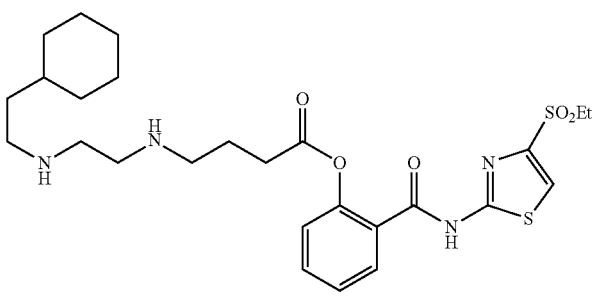 |
| 282 | 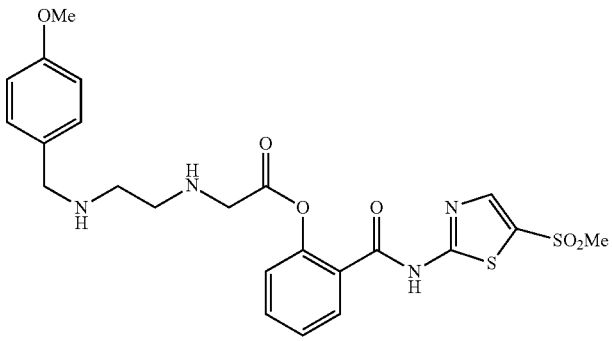 [SMILES: COc1ccc(CNCCNCC(=O)Oc2ccccc2C(=O)Nc2ncc(S(C)(=O)=O)s2)cc1] |

TABLE 7-continued
| No. | Structure |
|---|---|
| 283 | 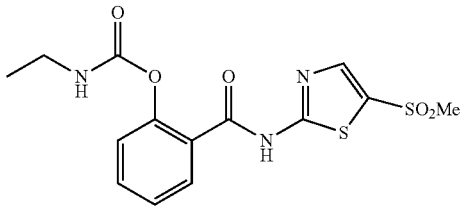 [SMILES: CCNC(=O)Oc1ccccc1C(=O)Nc1ncc(S(C)(=O)=O)s1] |
| 284 | 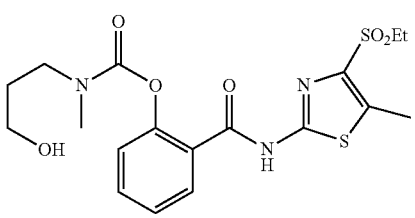 |
| 285 | 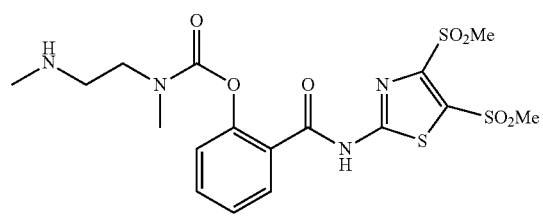 [SMILES: CNCCN(C)C(=O)Oc1ccccc1C(=O)Nc1nc(S(C)(=O)=O)c(S(C)(=O)=O)s1] |
| 286 | 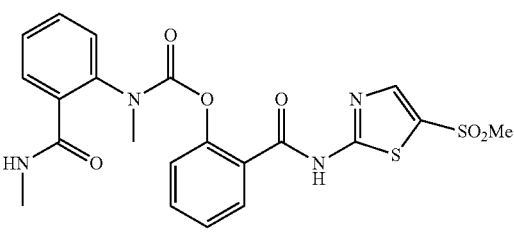 [SMILES: CNC(=O)c1ccccc1N(C)C(=O)Oc1ccccc1C(=O)Nc1ncc(S(C)(=O)=O)s1] |
| 287 | 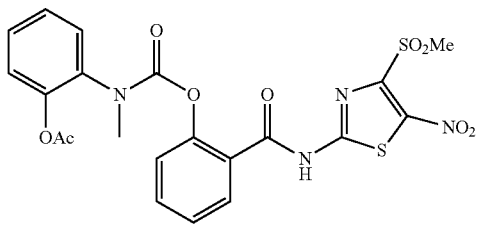 [SMILES: CC(=O)Oc1ccccc1N(C)C(=O)Oc1ccccc1C(=O)Nc1nc(S(C)(=O)=O)c([N+](=O)[O-])s1] |
| 288 | 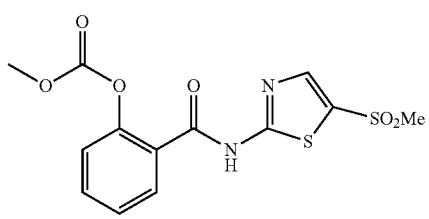 [SMILES: COC(=O)Oc1ccccc1C(=O)Nc1ncc(S(C)(=O)=O)s1] |
| 289 | 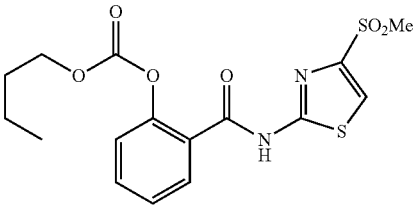 [SMILES: CCCCOC(=O)Oc1ccccc1C(=O)Nc1nc(S(C)(=O)=O)cs1] |

TABLE 7-continued

| No. | Structure |
|---|---|
| 290 | (isopropyl carbonate on phenyl)-C(O)-NH-(thiazole-5-SO₂Me) |
| 291 | (ethyl carbonate on phenyl)-C(O)-NH-(thiazole-4-SO₂Et) |
| 292 | (tert-butyl carbonate on phenyl)-C(O)-NH-(thiazole-5-SO₂Me) |
| 293 | (neopentyl carbonate on phenyl)-C(O)-NH-(thiazole-5-SO₂Me) |
| 294 | (cyclohexyl carbonate on phenyl)-C(O)-NH-(thiazole-4-SO₂Me, 5-CN) |
| 295 | (cyclohexylmethyl carbonate on phenyl)-C(O)-NH-(thiazole-5-SO₂Me) |

TABLE 7-continued

| No. | Structure |
|-----|-----------|
| 296 | 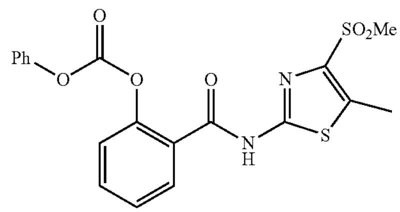 [SMILES: Cc1sc(NC(=O)c2ccccc2OC(=O)Oc2ccccc2)nc1S(C)(=O)=O] |
| 297 | 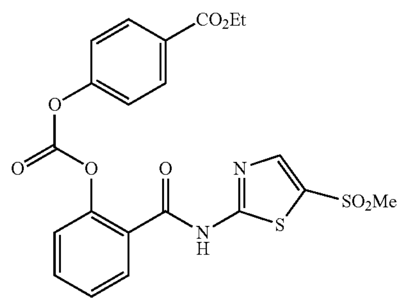 [SMILES: CCOC(=O)c1ccc(OC(=O)Oc2ccccc2C(=O)Nc2ncc(S(C)(=O)=O)s2)cc1] |
| 298 | 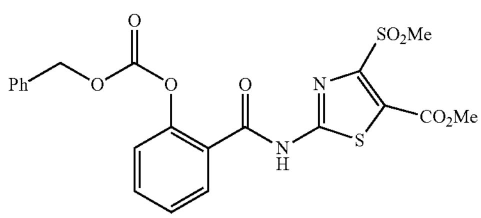 [SMILES: COC(=O)c1sc(NC(=O)c2ccccc2OC(=O)OCc2ccccc2)nc1S(C)(=O)=O] |
| 299 | 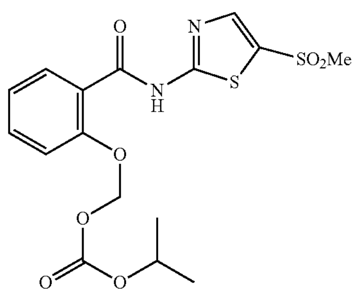 [SMILES: CC(C)OC(=O)OCOc1ccccc1C(=O)Nc1ncc(S(C)(=O)=O)s1] |
| 300 | 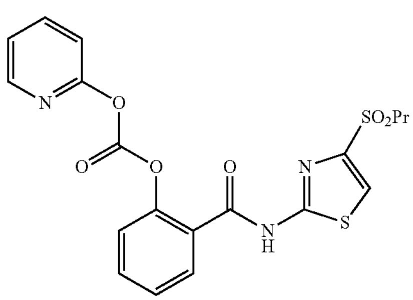 |

TABLE 7-continued

| No. | Structure |
|-----|-----------|
| 301 | 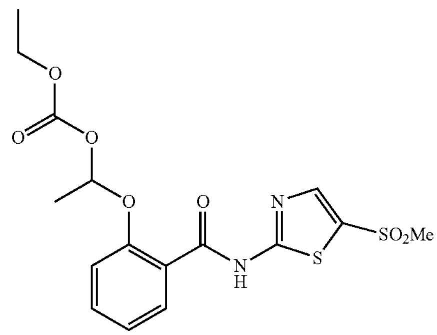 [SMILES: CCOC(=O)OC(C)Oc1ccccc1C(=O)Nc1ncc(S(C)(=O)=O)s1] |
| 302 | 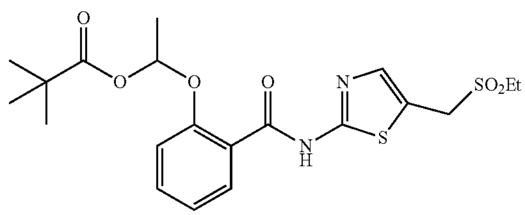 |
| 303 | 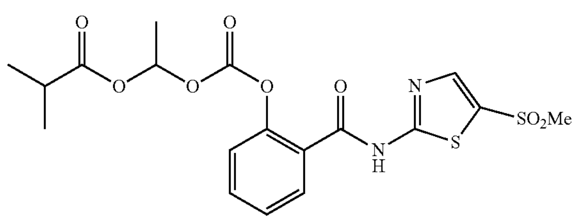 [SMILES: CC(OC(=O)Oc1ccccc1C(=O)Nc1ncc(S(C)(=O)=O)s1)OC(=O)C(C)C] |
| 304 | 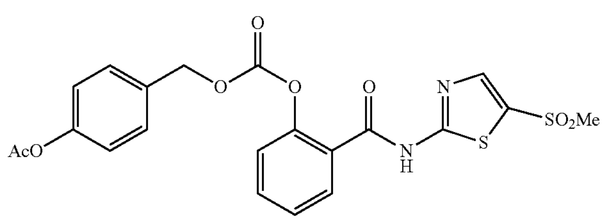 [SMILES: CC(=O)Oc1ccc(COC(=O)Oc2ccccc2C(=O)Nc2ncc(S(C)(=O)=O)s2)cc1] |
| 305 | 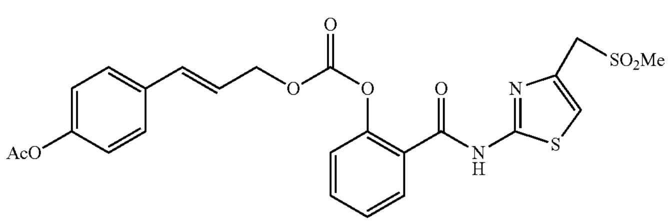 [SMILES: CC(=O)Oc1ccc(/C=C/COC(=O)Oc2ccccc2C(=O)Nc2nc(CS(C)(=O)=O)cs2)cc1] |
| 306 | 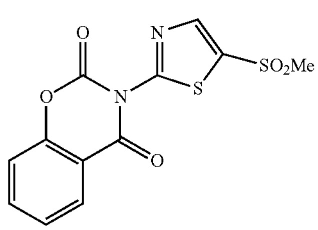 [SMILES: CS(=O)(=O)c1cnc(-n2c(=O)oc3ccccc3c2=O)s1] |

Table 8 designates the melting points of various compounds.

TABLE 8

| Compound # | Structure | Melting Point (° C.) |
|---|---|---|
| 11 | 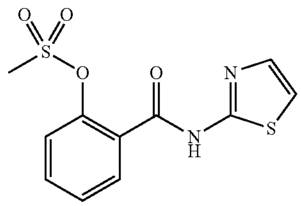 [SMILES: CS(=O)(=O)Oc1ccccc1C(=O)Nc1nccs1] | 185.5-187.8 |
| 6 | 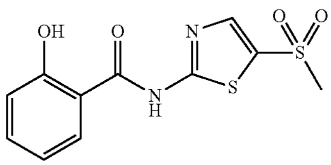 [SMILES: CS(=O)(=O)c1cnc(NC(=O)c2ccccc2O)s1] | 282-283 |
| 60 | 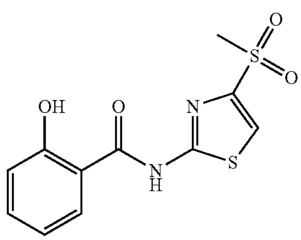 [SMILES: CS(=O)(=O)c1csc(NC(=O)c2ccccc2O)n1] | 223.5-225.6 |
| 7 | 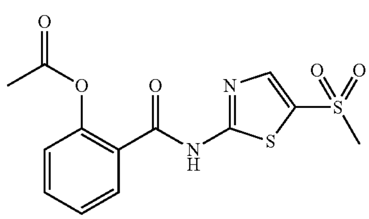 [SMILES: CC(=O)Oc1ccccc1C(=O)Nc1ncc(S(C)(=O)=O)s1] | 173-175 |
| 62 | 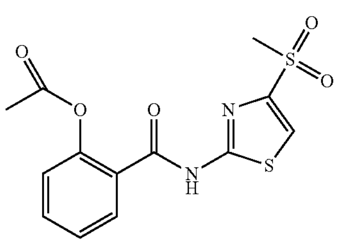 [SMILES: CC(=O)Oc1ccccc1C(=O)Nc1nc(S(C)(=O)=O)cs1] | 175.6-178.8 |
| 69 | 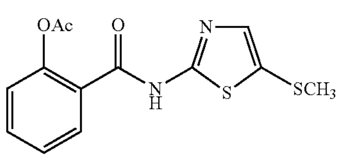 | 145-147 |
| 70 | 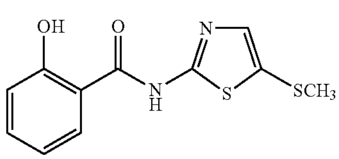 [SMILES: CSc1cnc(NC(=O)c2ccccc2O)s1] | 225-226 |

TABLE 8-continued

| Compound # | Structure | Melting Point (° C.) |
|---|---|---|
| 71 | 2-OAc-C6H4-C(O)NH-thiazole-5-S(CH2)3CH3 | 100-101 |
| 72 | 2-OH-C6H4-C(O)NH-thiazole-5-S(CH2)3CH3 | 180-181 |
| 73 | 2-OAc-C6H4-C(O)NH-thiazole-5-SO2(CH2)3CH3 | 138-140 |
| 74 | 2-OH-C6H4-C(O)NH-thiazole-5-SO2(CH2)3CH3 | 235-236 |
| 75 | 2-ONa-C6H4-C(O)NH-thiazole-5-S(O)2CH3 | >300 |
| 76 | 4-AcO-C6H4-C(O)NH-thiazole-5-SCH3 | 193.5-195.5 |
| 77 | 3-AcO-C6H4-C(O)NH-thiazole-5-SCH3 | 135.2-136.2 |
| 78 | 4-AcO-C6H4-C(O)NH-thiazole-5-S(O)2CH3 | 279.6-280.6 |
| 79 | 3-AcO-C6H4-C(O)NH-thiazole-5-S(O)2CH3 | 186.5 (dec) |

TABLE 8-continued

| Compound # | Structure | Melting Point (° C.) |
|---|---|---|
| 80 | 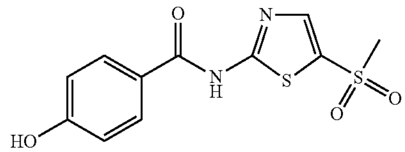 [SMILES: CS(=O)(=O)c1cnc(NC(=O)c2ccc(O)cc2)s1] | 252.5-255.5 (dec) |
| 81 | 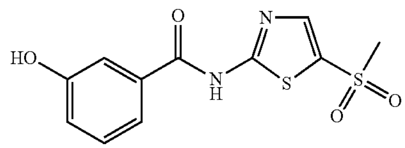 [SMILES: CS(=O)(=O)c1cnc(NC(=O)c2cccc(O)c2)s1] | 271.1-272.3 |
| 82 | 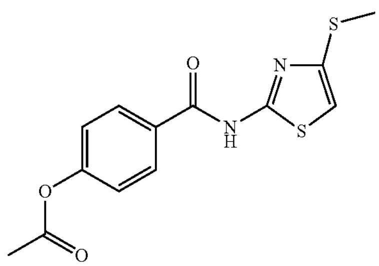 [SMILES: CSc1csc(NC(=O)c2ccc(OC(C)=O)cc2)n1] | 185.7-188.7 |
| 83 | 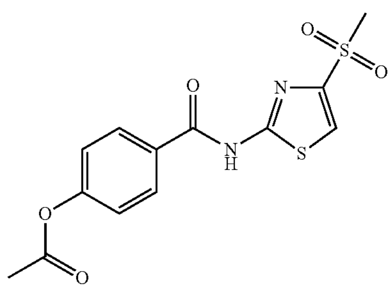 [SMILES: CC(=O)Oc1ccc(C(=O)Nc2nc(S(C)(=O)=O)cs2)cc1] | 242-246 (dec) |
| 84 | 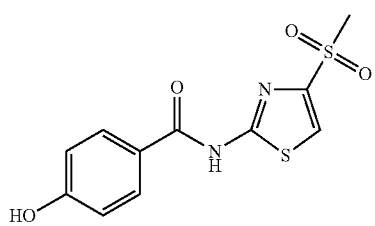 [SMILES: CS(=O)(=O)c1csc(NC(=O)c2ccc(O)cc2)n1] | 253-255 (dec) |
| 86 | 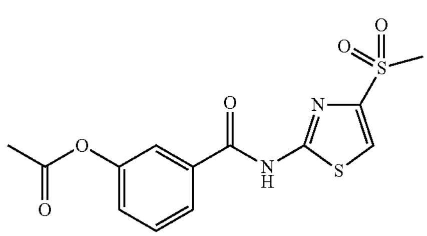 [SMILES: CC(=O)Oc1cccc(C(=O)Nc2nc(S(C)(=O)=O)cs2)c1] | 209-212 |
| 87 | 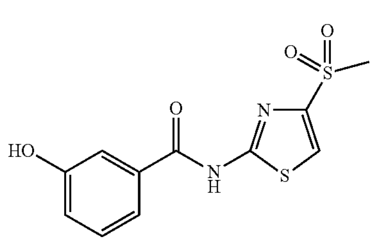 [SMILES: CS(=O)(=O)c1csc(NC(=O)c2cccc(O)c2)n1] | 258-259 (dec) |

For the above compounds that have a methylsulfonyl (—SO$_2$CH$_3$), it is also envisioned by the inventors that in place of the methylsulfonyl a moiety selected from —SO$_2$CH$_2$CH$_3$, —SO$_2$CH$_2$CH(CH$_3$)$_2$, —CH$_2$SO$_2$CH$_3$, —NHSO$_2$CH$_3$ and —SO$_2$-cyclopropyl may be used.

A compound of the present invention, where R$_6$ is SO$_2$CH$_3$, may be made by reacting an acyl halide with an amine under suitable reaction conditions. In some embodiments, the reaction may be generically represented as follows:

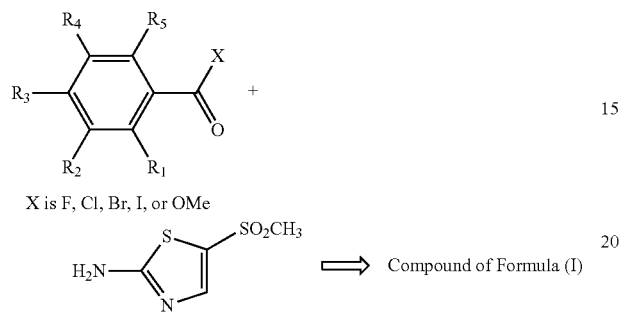

X is F, Cl, Br, I, or OMe

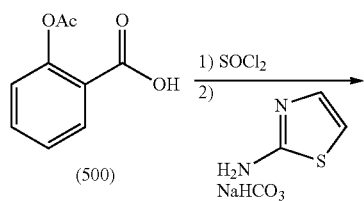

⇒ Compound of Formula (I)

Compounds of the present invention may also be made in accordance with the following reaction scheme:

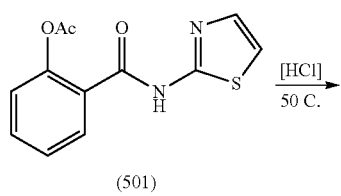

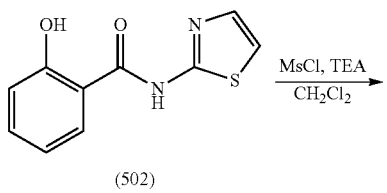

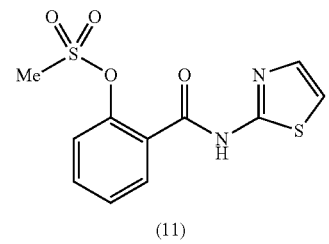

The compound, 2-(thiazol-2-ylcarbamoyl)phenyl methanesulfonate (11), may be synthesized by the method described in Example 3.0.

Other compounds of the present invention may also be made in accordance with the following reaction scheme:

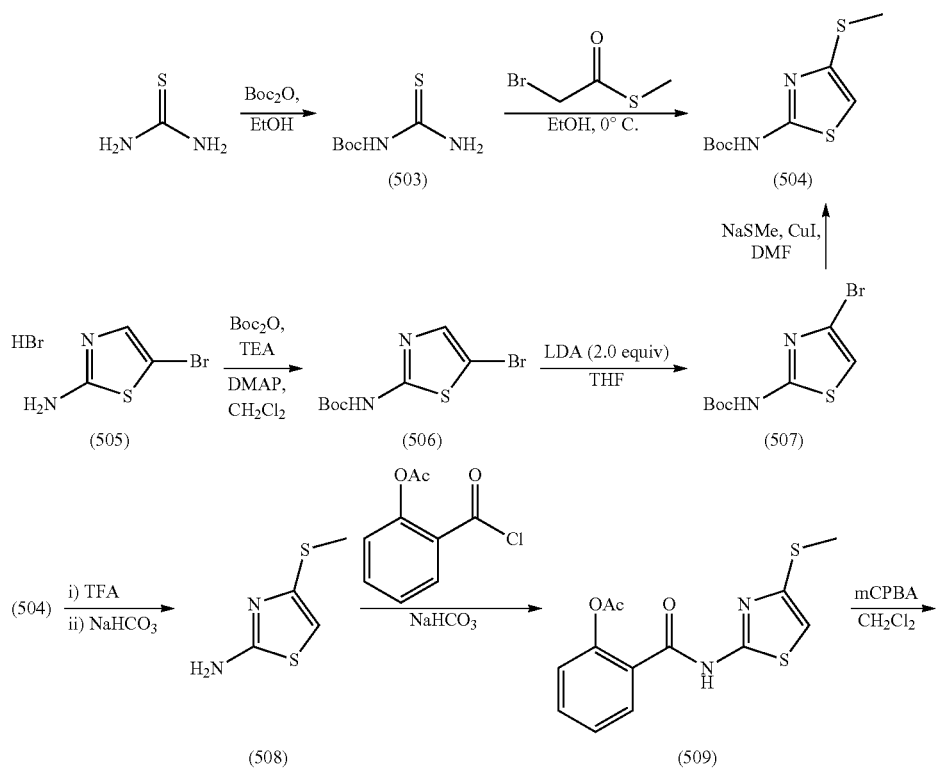

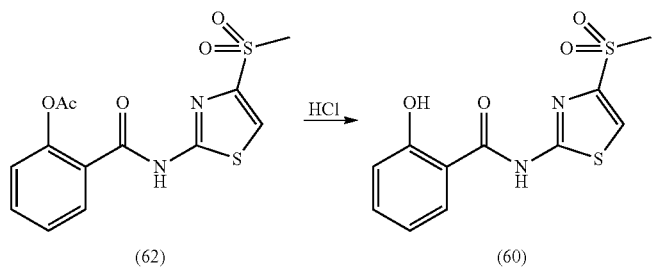

The compounds 2-hydroxy-N-[4-(methylsulfonyl)-1,3-thiazol-2-yl]benzamide (60) and 2-{[4-(methylsulfonyl)-1,3-thiazol-2-yl]carbamoyl}phenyl acetate (62) may be synthesized by the method described in Example 4.0.

Other compounds of the present invention may also be made in accordance with the following reaction scheme:

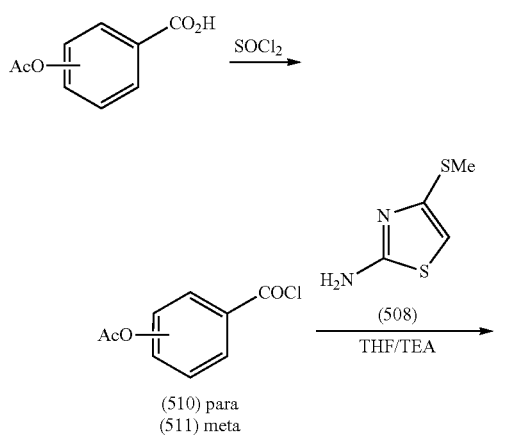

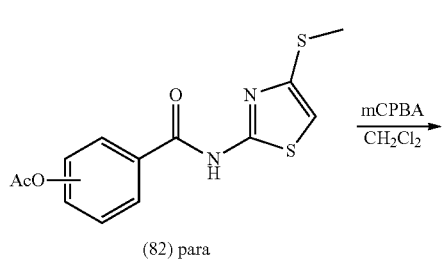

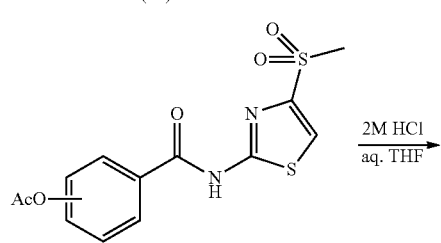

-continued

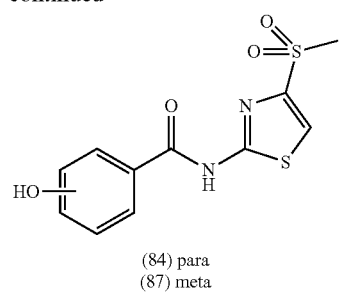

(84) para
(87) meta

The compounds 4-{[4-(methylsulfonyl)-1,3-thiazol-2-yl]carbamoyl}phenyl acetate (83), 4-hydroxy-N-[4-(methylsulfonyl)-1,3-thiazol-2-yl]benzamide (84), 3-{[4-(methylsulfonyl)-1,3-thiazol-2-yl]carbamoyl}phenyl acetate (86), and 3-hydroxy-N-[4-(methylsulfonyl)-1,3-thiazol-2-yl]benzamide (87), may be synthesized by the general methods described in Example 5.0.

Furthermore, compounds of the present invention may also be made in accordance with the following reaction scheme:

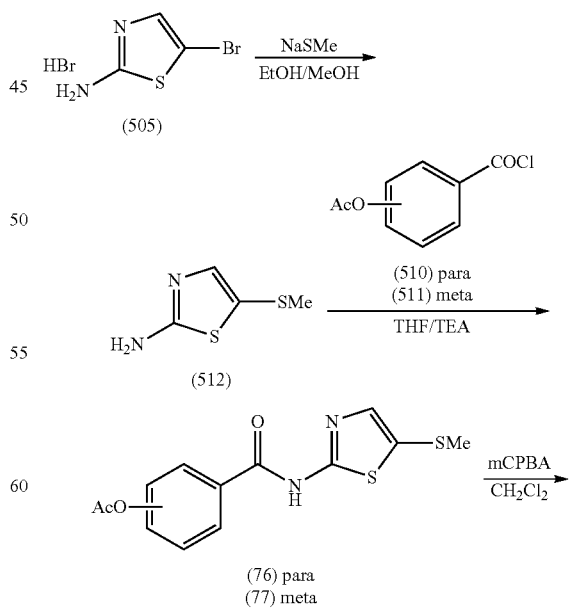

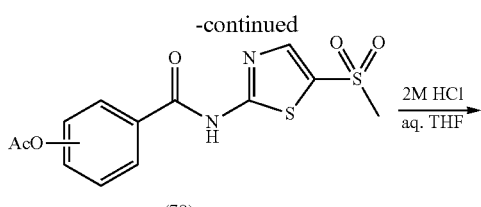

(78) para
(79) meta

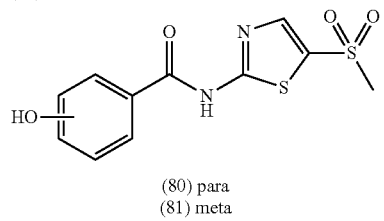

(80) para
(81) meta

The compounds 4-{[5-(methylsulfonyl)-1,3-thiazol-2-yl]carbamoyl}phenyl acetate (78), 3-{[5-(methylsulfonyl)-1,3-thiazol-2-yl]carbamoyl}phenyl acetate (79), 4-hydroxy-N[5-(methylsulfonyl)-1,3-thiazol-2-yl]benzamide (80) and 3-hydroxy-N-[5-(methylsulfonyl)-1,3-thiazol-2-yl]benzamide (81) may be synthesized by the general methods described in Example 6.0.

Other compounds of the present invention may also be made in accordance with the following reaction scheme:

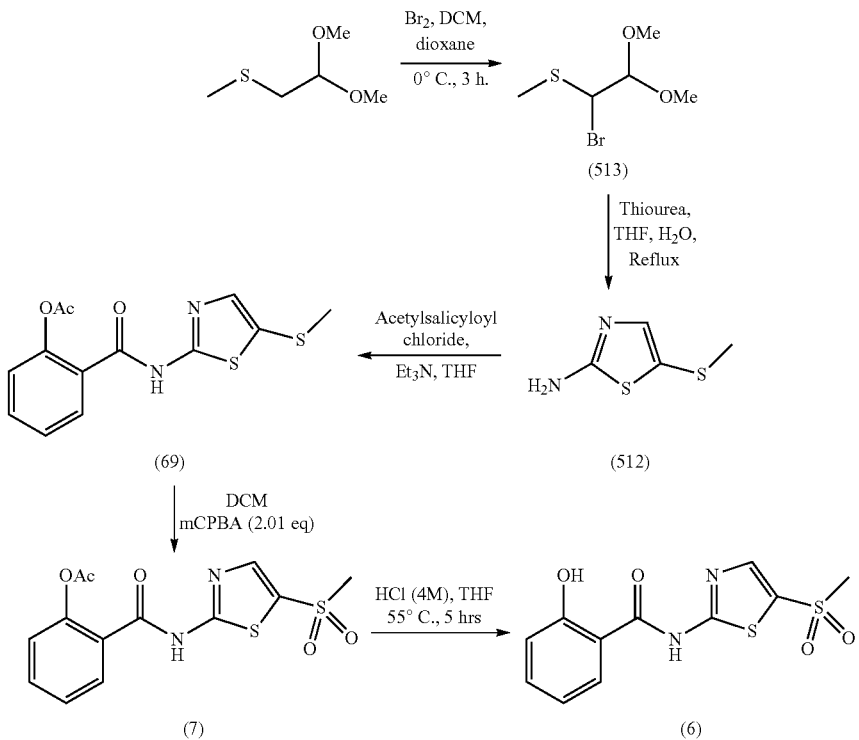

The compounds 2-(5-(methylsulfonyl)thiazol-2-ylcarbamoyl)phenyl acetate (7) and 2-hydroxy-N-(5-(methylsulfonyl)thiazol-2-yl)benzamide (6), may be synthesized by the method described in Example 7.0.

The present invention also includes a composition comprising, in a carrier, at least one compound of the present invention.

The term carrier is used in its broadest sense. For example, the term carrier refers to any carriers, diluents, excipients, wetting agents, buffering agents, suspending agents, lubricating agents, adjuvants, vehicles, delivery systems, emulsifiers, disintegrants, absorbents, preservatives, surfactants, colorants, flavorants, and sweeteners. In some embodiments, the carrier may be a pharmaceutically acceptable carrier, a term narrower than carrier, because the term pharmaceutically acceptable carrier" means a non-toxic that would be suitable for use in a pharmaceutical composition.

The present invention also relates to a pharmaceutical composition comprising, in a pharmaceutically acceptable carrier, an effective amount of at least one compound of the invention.

The term effective amount is used in its broadest sense. The term, for example, refers to the amount required to produce a desired effect.

In some embodiments, the compound of the invention is present in a pharmaceutical composition in an effective amount for treating HCV infection (e.g., chronic HCV infection). "Treating HCV infection" may refers to: (i) preventing HCV infection from occurring in an animal that may be predisposed to HCV infection but has not yet been diagnosed as having it; (ii) inhibiting or slowing HCV infection, e.g. arresting its development; (iii) relieving chronic infection, e.g. causing its regression; (iv) improving a symptom in a subject having chronic infection; and/or (v) prolonging the survival of a subject having chronic infection.

The compositions of the present invention may be formulated as solid or liquid dosage forms, or as pastes or ointments, and may optionally contain further active ingredients.

A pharmaceutical composition of the present invention comprises a pharmaceutically acceptable carrier, which is not particularly limited, and includes a wide range of carriers known to those of ordinary skill in the art, and including wetting or dispersing agents (U.S. Pat. No. 5,578,621, which is incorporated herein by reference), starch derivatives (U.S. Pat. No. 5,578,621, which is incorporated herein by reference), excipients, and the like. Tablet embodiments may optionally comprise a coating of a substance that constitutes an enteric coating, i.e., a coating that substantially insoluble in gastric secretion but substantially soluble in intestinal fluids.

Pharmaceutical compositions comprising the compounds of the present invention are in some embodiments formulated for oral administration and are optionally in the form of a liquid, for example an emulsion or a solution or a suspension in water or oil such as arachis oil, or other liquid. Formulations of non-aqueous micellar solutions may be prepared according to the method disclosed in U.S. Pat. No. 5,169,846, which is incorporated herein by reference. Alternatively, tablets can be manufactured, for example, by performing the following steps: wet granulation; drying; and compression. Film coating may generally be performed with organic solvents.

The present invention is a method, comprising administering to a subject at least one compound of the present invention in an amount in an effective amount for treating HCV infection (e.g., chronic HCV infection). In some embodiments, the method, comprising administering to a subject at least one pharmaceutical composition which comprises at least one compound of the present invention in an amount in an effective amount for treating HCV infection (e.g., chronic HCV infection).

In some embodiments, the subject is chosen from animals. In some embodiments, the subject is chosen from mammals. In some embodiments, the subject is chosen from pets, such as mice, dogs, cats, etc. In some embodiments, the subject is chosen from humans.

In some embodiments, the invention provides a method of treating a viral infection in a subject, comprising administering to the subject at least one dose of an effective amount of at least one compound of the present invention. In some embodiments, the invention provides a method of treating a viral infection in a subject, comprising administering to the subject at least one dose of an effective amount of at least one pharmaceutical composition comprising, in a pharmaceutically acceptable carrier, at least one compound of the present invention.

In some embodiments the antiviral treatment or prophylactic dosages of the compound of the present invention may depend upon the weight of the subject, and may be inferred by one of ordinary skill without undue experimentation by reference to the following examples, which are set forth for purposes of illustration and are not intended to be limiting.

The inventive compounds and compositions may be administered locally or systemically by any means known to an ordinarily skilled artisan. For example, the inventive compounds and compositions may be administered orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intraarterial, intramuscular, intraperitoneal, intrathecal, intraventricular, intrasternal, intracranial or intraosseous injection and infusion techniques. The exact administration protocol will vary depending upon various factors including the age, body weight, general health, sex and diet of the patient; the determination of specific administration procedures would be routine to an ordinarily skilled artisan.

Dose levels on the order of about 0.1 to about 100 mg/kg of the active ingredient compound are useful in the treatment of the above conditions (e.g., 0.1 mg/kg-day). In some embodiments, the amounts range from about 1 to about 10 mg/kg, and in other embodiments, the amounts range from about 2 to about 5 mg/kg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Any administration regimen for regulating the timing and sequence of drug delivery can be used and repeated as necessary to effect treatment. Such regimen may include multiple uses or preadministration and/or co-administration and/or postadministration with food, liquid, or water.

The present invention also relates to a kit, comprising, in a compartment, at least one pharmaceutical composition comprising, in a pharmaceutically acceptable carrier, an effective amount of at least one compound of the invention. In some embodiments, the kit further comprises written instructions for administering the pharmaceutical composition. In some embodiments, written instructions for administering concern indications noted elsewhere in this disclosure. In some embodiments, written instructions for administering concern an administration regimen noted elsewhere in this disclosure.

The kit could take any form. By way of example, a kit includes one or more containers for storing a pharmaceutical composition. In some embodiments, a container contains written instructions for administering the pharmaceutical composition. In some embodiments, a container contains is the substrate for the written instructions for administering the pharmaceutical composition. In some embodiments, the written instructions for administering the pharmaceutical composition are affixed to a container, for example, as in a container for filling a prescription sometimes has written instructions affixed on a surface.

In some embodiments, the compound of the present invention may exhibit selective antiviral activity. The term "selective antiviral" as used herein means that, at dosages effective for the prevention or treatment of a viral disease, the activity is more antiviral than antibacterial, antifungal, or antiparasite, and gut flora of the subject is not disrupted to levels expected with broad spectrum antibiotics. For example, the effective dosage for antiviral treatment (e.g., reducing viral load at least about 2 times) may not reduce bacterial, fungal, or parasite levels in the gut (e.g., more than about 2 times)

Other embodiments of the invention will be apparent to those skilled in the art from consideration of the specification and practice of the invention disclosed herein. It is intended that the specification and its examples be considered as exemplary only, with a true scope and spirit of the invention being indicated by what may eventually be claimed.

EXAMPLES

1. Materials and Methods 1.1 Materials

Lamivudine (LMV) and adefovir dipovoxil (ADV), and 2'-C-methyl cytidine were purchased from Moraveck Biochemicals, Inc. (La Brea, Calif. USA). Recombinant human interferon alpha 2b (IFN) was purchased from PBL Biomedical Laboratories (Piscataway, N.J. USA). All other test compounds (FIG. 1) were provided by Romark Laboratories, L.C. Human serum (heat-inactivated, mixed gender, lot BRH125374) was purchased from Bioreclamation, Inc. (Hicksville, N.Y.).

1.2. HBV Studies

1.2.1. Antiviral Assays

HBV antiviral assays were conducted as previous described (Korba and Gerin, 1992). Briefly, confluent cultures of 2.2.15 cells were maintained on 96-well flat-bottomed tissue culture plates (confluence in this culture system is required for active, high levels of HBV replication equivalent to that observed in chronically-infected individuals (Sells, et al., 1988; Korba and Gerin, 1992). Cultures were treated with nine consecutive daily doses of the test compounds. HBV DNA levels were assessed by quantitative blot hybridization 24 hr. after the last treatment. Cytotoxicity was assessed by uptake of neutral red dye 24 hr. following the last treatment.

1.2.2. Activity Against Drug-Resistant HBV Mutants

Activity against LMV-resistant (Allen et al., 1998) and ADV-resistant (Angus et al., 2003) HBV mutants was performed in a 5-day assay using a transient transfection method as previously described (Iyer et al., 2004). Antiviral activity was determined by quantitative Southern blot hybridization of intracellular HBV DNA replication intermediates (HBV RI).

1.2.3. Production of HBV Proteins

Cultures of 2.2.15 cells were treated under standard procedures and semi-quantitative EIA-based analysis of HBV proteins was performed as previously described (Korba and Gerin, 1995), except that HBeAg was analyzed ETI-EBK Plus® (DiaSorin, Inc., Stillwater, Minn. USA). Samples were diluted (2 to 10-fold) to bring levels into the dynamic response ranges of the EIA's. HBsAg, and HBeAg were analyzed from culture medium samples and HBcAg was analyzed from intracellular lysates. Intracellular HBV RNA was assessed by quantitative northern blot hybridization (Korba and Gerin, 1995).

1.3. HCV Studies

Antiviral activity of test compounds was assessed in a 3-day assay using the stably-expressing HCV replicon cell line, AVA5 (sub-genomic CON1, genotype 1b) (Blight et al., 2000) maintained as sub-confluent cultures on 96-well plates as previously described (Okuse et al., 2005). Antiviral activity was determined by blot hybridization analysis of intracellular HCV RNA (normalized to the level of cellular B-actin RNA in each culture sample) and cytotoxicity was assessed by neutral red dye uptake after 3 days of treatment. Additional studies were performed using Huh7 cells containing another HCV replicon, H/FL-Neo, a genotype 1a full length construct (Blight et al., 2003). For studies involving human serum, standard culture medium (which contains 10% fetal bovine serum) and assay conditions were maintained.

1.4. Presentation of Results $EC_{50}$, $EC_{90}$ and $CC_{50}$ values (±standard deviations [S.D.]) were calculated by linear regression analysis using data combined from all treated cultures (Korba and Gerin, 1992; Okuse et al., 2005). $EC_{50}$ and $EC_{90}$ are drug concentrations at which a 2-fold, or a 10-fold depression of intracellular HBV DNA or HCV RNA (relative to the average levels in untreated cultures), respectively, was observed. $CC_{50}$ is the drug concentration at which a 2-fold lower level of neutral red dye uptake (relative to the average levels in untreated cultures) was observed. Selectivity index (S.I.) was calculated as $CC_{50}/EC_{90}$ for HBV assays and $CC_{50}/EC_{50}$ for HCV assays. $EC_{90}$ values were used for calculation of the S.I. in HBV assays since at least a 3-fold depression of HBV DNA levels is typically required to achieve statistical significance in this assay system (Korba and Gerin, 1992). For combination treatments, $EC_{50}$, $EC_{90}$, $CC_{50}$ and S.I. are presented for the first compound listed. The molar ratio of the compounds in each combination is also indicated.

2. Results

2.1. Hepatitis B Virus (HBV)

2.1.1. Activities of Compounds and Combinations in 2.2.15 Cell Cultures

Figure 2:
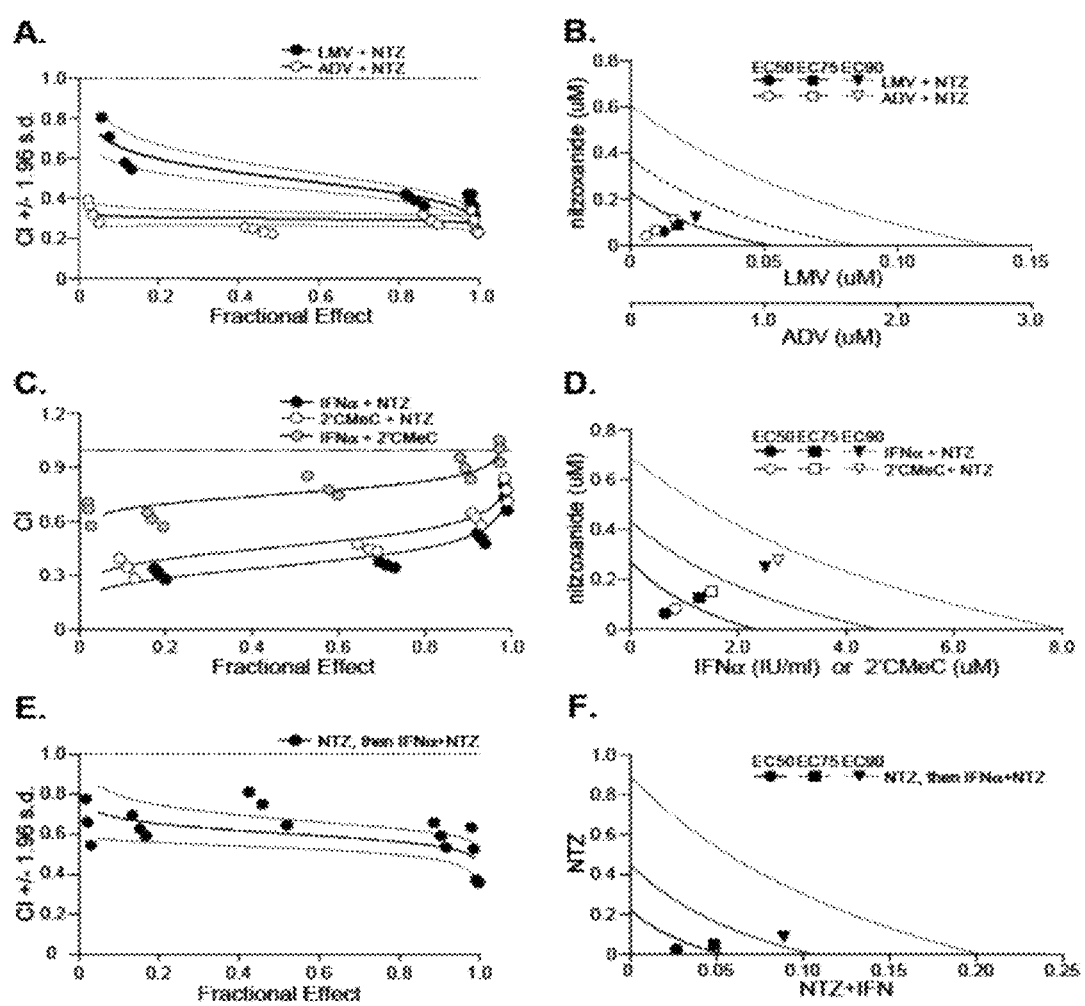
FIG. 2 provides examples of the analysis of interactions between interferons in combination treatments. Analysis of combination therapies was performed using Calcusyn™ software (Biosoft, Inc., Cambridge, UK). Panels A and B display anti-HBV treatments; panels C to F display anti-HCV treatments. Two types of evaluations are presented. Panels A, C, and E present CI-Fa (Combination Index-Fraction (of virus) affected) plots (Belen'kii and Schinazi, 1994). For these plots, a combination index [CI] greater than 1.0 indicates antagonism and a CI less than 1.0 indicates synergism. Evaluations of synergy, additivity (summation), or antagonism at different levels of virus inhibition (e.g. 5% (Fa=0.5) to 99% (Fa=0.99)) are provided by the plotted lines and points. Dotted lines in panel A indicate 1.96 standard deviations (not shown in panel C for clarity). Panels B, D, and F present conservative isobolograms. For these plots, $EC_{50}$, $EC_{75}$, and $EC_{90}$ (50%, 75%, and 90% effective antiviral concentrations) values for the combination treatments are displayed as single points. Three lines radiating out from the axes denote the expected (e.g. additive) $EC_{50}$, $EC_{75}$, and $EC_{90}$ values for drug combinations as calculated from the monotherapies. $EC_{50}$, $EC_{75}$, and $EC_{90}$ values for the combinations that plot to the left (e.g. less than) of the corresponding lines indicate synergy, and values plotting to the right (e.g. greater than) of the corresponding lines indicate antagonism.

NTZ and its active metabolite, TIZ, exhibited selective inhibition of intracellular HBV replication and extracellular virus production by 2.2.15 cells (Table 1). Several other thiazolides (see Table 1) were also effective inhibitors of HBV replication in this assay system. Combinations of NTZ with either of two drugs licensed for anti-HBV therapy, lamivudine (LMV) and adefovir dipovoxil (ADV), demonstrated synergistic interactions when used to treat 2.2.15 cells (Table 1, FIGS. 2A and 2B). The anti-HBV assays were conducted under confluence as this provides the conditions for optimal HBV replication (Sells, et al., 1988; Korba and Gerin, 1992). While under the conditions of the antiviral assay NTZ displayed minimal cytotoxicity (>100 µM, Table 1), cytotoxicity of NTZ in rapidly dividing cultures of 2.2.15 cells was higher (20±1.3 µM).

2.1.2. Activity of NTZ and RM4850 Against Drug-Resistant HBV Mutants

NTZ and RM4850 were effective inhibitors of several HBV LMV-resistant and one ADV-resistant constructs in transient transfection assays in Huh7 cells (Table 2). No significant differences in potency of these thiazolides relative to that observed for wild-type HBV were observed for any of the drug-resistant viruses tested.

2.1.3. Effect of NTZ on Production of HBV Proteins

Unlike most viruses (including HCV), HBV RNA transcription and protein production are effectively separated from viral genome replication due to the presence of a long-lived population of covalently-closed viral template genomes in the host cell nucleus (cccDNA) (see Locarnini, 2004 for a review). Intracellular HBV replication takes place in viral nucleocapsids located in the cytoplasm. As a result, most compounds that inhibit HBV DNA replication (e.g. nucleoside analogues), do not typically alter HBV protein production, especially in cell culture.

Suspecting a novel mechanism of action of NTZ against HBV, we conducted studies to determine if the drug inhibited the production of major HBV proteins. As assessed by semi-quantitative EIA, NTZ reduced the levels of extracellular HBV surface and e antigens (HBsAg, HBeAg), as well as the levels of intracellular HBV nucleocapsid core antigen (HBcAg) in a dose-dependent manner (Table 3, FIG. 3). The potency of NTZ against HBsAg and HBeAg was similar to that observed against HBV virion production in the same experiment. The relative potency of NTZ against intracellular HBcAg was similar to that observed for the inhibition of intracellular HBV DNA replication. No quantitative interference with the ability of the EIAs to detect HBV proteins was observed in samples from control cultures to which 10 µM NTZ was added (data not shown).

NTZ did not induce a reduction in intracellular HBV RNA as assessed by Northern blot hybridization (Table 3, FIG. 3). In the same experiment, LMV did not affect the levels of HBV proteins or HBV RNA despite inducing significant reductions in HBV virion production and intracellular HBV DNA replication (Table 3).

2.2. Hepatitis C Virus (HCV)

2.2.1. Activities of Compounds and Combinations in HCV Replicon Cell Cultures NTZ and TIZ selectively reduced intracellular HCV replication in AVA5 cells (Table 4). Both compounds were more cytotoxic in this cell line than in 2.2.15 cells, but the compounds were also much more potent against HCV replication. Combinations of NTZ or TIZ with either recombinant human interferon alpha 2b (IFNα), or an NS5B (HCV polymerase) inhibitor, 2'-C-methyl cytidine (2'CmeC, Pierra, et al. 2005), exhibited synergistic interactions against HCV replication (Table 4, FIGS. 2C and 2D).

Only two of the other thiazolides, RM4832 and RM4863, exhibited activity against HCV (Table 4). Antiviral activities of NTZ, TIZ and RM4832 against a full length genotype 1a replicon (Blight, et al. 2003) were equivalent to that observed for AVA5 cells (genotype 1b) (Table 4).

2.2.2. Effect of Pre-Treating with NTZ Before Combination Treatments

Based on observations in early clinical trials using NTZ with pegylated interferon, we evaluated the in vitro effect of a regimen consisting of 3 days treatment with NTZ followed by 3 days of a combination of NTZ plus IFNα. Pre-treatment with NTZ monotherapy improved the potency of combination treatment with NTZ plus IFNα by approximately 3-fold (Table 5, FIG. 2 panels E and F). Pre-treatment did not, however, affect the potency of combination treatment with 2'CmeC (Table 5).

2.2.3. Effect of Human Serum on Anti-HCV Potency and Cytotoxicity of TIZ in Cells NTZ and its circulating metabolite, TIZ, are highly bound (>99%) to plasma proteins in human serum. To evaluate the effect of human serum on the anti-HCV potency and cytotoxicity of TIZ, human serum was added to the culture medium at various concentrations (Table 6). The $CC_{50}$, $EC_{50}$, and $EC_{90}$ of TIZ increased with increasing concentrations of human serum up to 20%. The $EC_{50}$ and $EC_{90}$ in the presence of 30% human serum were similar to those at 20% human serum (a plateau effect) suggesting that maximum extent of protein binding had been reached. The levels of HCV and B-actin RNA in untreated cultures were similar at different concentrations of human serum up to 30% (data not shown). Higher concentrations of human serum significantly lowered cell viability (data not shown). In the below tables, RM4863 is the same as compound 6 of Table 7.

TABLE 1

Relative potency (µM) of test compounds against HBV replication in 2.2.15 cell cultures.

| Compound | $CC_{50}$ | Extracellular virion DNA $EC_{50}$ | $EC_{90}$ | Intracellular HBV RI* $EC_{50}$ | $EC_{90}$ | Selectivity Index Virion | RI |
|---|---|---|---|---|---|---|---|
| LMV | 2347 ± 88 | 0.05 ± 0.01 | 0.15 ± 0.02 | 0.16 ± 0.03 | 0.55 ± 0.06 | 15646 | 4267 |
| ADV | >300# | 1.0 ± 0.2 | 3.0 ± 0.3 | | | >100 | |
| NTZ | >100 | 0.12 ± 0.02 | 0.83 ± 0.09 | 0.59 ± 0.07 | 2.1 ± 0.2 | >121 | >48 |
| TIZ | >100 | 0.15 ± 0.02 | 0.58 ± 0.06 | 0.46 ± 0.05 | 1.2 ± 0.2 | >172 | >83 |
| RM4832 | >100 | 1.2 ± 0.1 | 4.0 ± 0.3 | 2.9 ± 0.3 | 8.7 ± 1.0 | >25 | >12 |
| RM4848 | >100 | 0.37 ± 0.07 | 1.7 ± 0.2 | | | >58 | |
| RM4850 | >100 | 0.33 ± 0.07 | 0.83 ± 0.10 | 0.90 ± 0.10 | 2.0 ± 0.2 | >120 | >51 |
| RM4851 | >100 | >10# | >10# | >10# | >10# | — | — |
| RM4852 | >100 | 1.0 ± 0.1 | 3.3 ± 0.3 | 2.7 ± 0.3 | 6.3 ± 0.7 | >30 | >16 |
| RM4863 | >100 | >10 | >10 | >10 | >10 | — | — |
| NTZ + LMV, 50:1 | >100 | 0.06 ± 0.005 | 0.16 ± 0.02 | | | >625 | |
| NTZ + ADV, 3:1 | >100 | 0.03 ± 0.004 | 0.11 ± 0.02 | | | >909 | |

*HBV RI, intracellular HBV RNA replication intermediates
no significant cytotoxic or antiviral activity observed up to indicated concentration.

TABLE 2

Relative potency (µM) of test compounds against drug-resistant HBV mutants in cell cultures.

| HBV Mutant | Nitazoxanide $EC_{50}$ | $EC_{90}$ | Lamivudine $EC_{50}$ | $EC_{90}$ | Adefovir dipovoxil $EC_{50}$ | $EC_{90}$ | RM4850 $EC_{50}$ | $EC_{90}$ |
|---|---|---|---|---|---|---|---|---|
| Wild-type | 0.21 ± 0.03 | 0.77 ± 0.09 | 0.2 ± 0.1 | 0.9 ± 0.2 | 2.0 ± 0.2 | 7.0 ± 0.8 | 0.73 ± 0.08 | 2.0 ± 0.3 |
| M204V | 0.15 ± 0.02 | 0.70 ± 0.08 | >100# | >100# | 1.5 ± 0.2 | 7.2 ± 0.8 | 0.80 ± 0.10 | 2.1 ± 0.3 |

TABLE 2-continued

Relative potency (μM) of test compounds against drug-resistant HBV mutants in cell cultures.

| HBV Mutant | Nitazoxanide | | Lamivudine | | Adefovir dipovoxil | | RM4850 | |
|---|---|---|---|---|---|---|---|---|
| | $EC_{50}$ | $EC_{90}$ | $EC_{50}$ | $EC_{90}$ | $EC_{50}$ | $EC_{90}$ | $EC_{50}$ | $EC_{90}$ |
| M204I | 0.31 ± 0.05 | 1.0 ± 0.2 | >100 | >100 | 2.5 ± 0.3 | 8.5 ± 1.0 | 1.0 ± 0.2 | 2.4 ± 0.3 |
| L180M | 0.23 ± 0.03 | 0.80 ± 0.09 | 16 ± 2.0 | 46 ± 5.6 | 2.6 ± 0.3 | 7.3 ± 0.8 | 0.83 ± 0.09 | 2.2 ± 0.2 |
| L180M/M204V | 0.18 ± 0.02 | 0.72 ± 0.09 | >100 | >100 | 2.5 ± 0.3 | 7.6 ± 0.8 | 0.87 ± 0.11 | 2.1 ± 0.3 |
| N236T | 0.28 ± 0.03 | 0.85 ± 0.10 | 0.3 ± 0.1 | 1.2 ± 0.2 | 11 ± 1.3 | 32 ± 3.6 | 0.67 ± 0.08 | 2.2 ± 0.2 |

[#]no significant antiviral activity observed up to indicated concentration.

TABLE 3

Relative potency (μM) of NTZ and lamivudine against HBV replication and protein levels in 2.2.15 cell cultures.

| | Nitazoxanide | | Lamivudine | |
|---|---|---|---|---|
| | $EC_{50}$ | $EC_{90}$ | $EC_{50}$ | $EC_{90}$ |
| Virion production | 0.19 ± 0.02 | 0.58 ± 0.04 | 0.05 ± 0.01 | 0.15 ± 0.02 |
| HBV R.I. | 0.73 ± 0.06 | 2.2 ± 0.3 | 0.16 ± 0.02 | 0.56 ± 0.07 |
| HBV RNA | — | — | — | — |
| HBsAg | 0.22 ± 0.03 | 1.0 ± 0.1 | — | — |
| HBeAg | 0.26 ± 0.02 | 1.3 ± 0.1 | — | — |
| HBcAg | 1.1 ± 0.1 | 3.0 ± 0.2 | — | — |

TABLE 4

Relative potency (μM) of test compounds against HCV replication in replicon cells.

| Compound | $CC_{50}$ | $EC_{50}$ | $EC_{90}$ | Selectivity Index |
|---|---|---|---|---|
| Genotype 1b replicon | | | | |
| IFNα | >10000[#]* | 1.9 ± 0.2* | 8.9 ± 0.9* | >5263 |
| 2'CmeC | >300 | 1.6 ± 0.2 | 8.3 ± 0.7 | >188 |
| NTZ | 38 ± 1.8 | 0.21 ± 0.03 | 0.93 ± 0.11 | 181 |
| TIZ | 15 ± 1.2 | 0.15 ± 0.02 | 0.81 ± 0.92 | 100 |
| RM4832 | 98 ± 3.2 | 4.9 ± 0.5 | 20 ± 1.9 | 20 |
| RM4848 | 15 ± 0.1 | >20[#] | >20[#] | — |
| RM4850 | 2.3 ± 0.2 | >20 | >20 | — |
| RM4851 | 5.6 ± 0.3 | >20 | >20 | — |
| RM4852 | 6.7 ± 0.4 | >20 | >20 | — |
| RM4863 | 2.8 ± 0.3 | 0.04 ± 0.005 | 0.59 ± 0.07 | 74 |
| 2'CmeC + IFNα, 1:1 | >300 | 0.67 ± 0.007 | 2.3 ± 0.3 | >448 |
| NTZ + IFNα, 1:10 | 33 ± 1.3 | 0.06 ± 0.008 | 0.25 ± 0.03 | 550 |
| NTZ + 2'CmeC, 1:10 | 35 ± 1.5 | 0.07 ± 0.005 | 0.28 ± 0.02 | 500 |
| TIZ + IFNα, 1:10 | 17 ± 1.3 | 0.07 ± 0.01 | 0.22 ± 0.03 | 245 |
| TIZ + 2'CmeC, 1:10 | 18 ± 1.1 | 0.06 ± 0.004 | 0.19 ± 0.02 | 300 |
| Genotype 1a replicon | | | | |
| IFNα | >10000 | 2.1 ± 0.2 | 9.4 ± 0.9 | >4762 |
| 2'CmeC | >300 | 1.8 ± 0.2 | 8.1 ± 0.8 | >167 |
| NTZ | 49 ± 1.5 | 0.33 ± 0.05 | 1.1 ± 0.1 | 149 |
| TIZ | 14 ± 0.2 | 0.25 ± 0.03 | 1.0 ± 0.1 | 56 |
| RM4832 | 88 ± 2.1 | 2.8 ± 0.3 | 9.4 ± 1.1 | 31 |

*concentrations for interferon are expressed in 'IU/ml.

[#]no significant cytotoxic or antiviral activity observed up to indicated concentration.

TABLE 5

Effect of NTZ montherapy pretreatment on combination therapy.

| Treatment (6 days total duration) | EC$_{50}$ | EC$_{90}$ |
|---|---|---|
| IFNα | 1.7 ± 0.2 | 7.8 ± 0.8 |
| 2'CmeC | 1.3 ± 0.2 | 5.8 ± 0.9 |
| NTZ | 0.20 ± 0.02 | 0.92 ± 0.10 |
| NTZ + IFNα, 1:10 | 0.09 ± 0.010 | 0.24 ± 0.04 |
| NTZ montherapy (3 days), then NTZ + IFNα (3 days) | 0.03 ± 0.004 | 0.09 ± 0.011 |
| NTZ + 2'CmeC, 1:10 | 0.05 ± 0.007 | 0.17 ± 0.03 |
| NTZ montherapy (3 days), then NTZ + 2'CmeC (3 days) | 0.06 ± 0.005 | 0.15 ± 0.02 |

* Values are expressed as μM concentrations of drug (first named drug in the case of combinations).

TABLE 6

Relative potency (μM) of TIZ against HCV replication in the presence of human serum.

| Concentration of human serum (%) | EC$_{50}$ | EC$_{90}$ | CC$_{50}$ |
|---|---|---|---|
| 0 | 0.25 ± 0.01 | 0.98 ± 0.04 | 28 ± 0.9 |
| 2.5 | 0.48 ± 0.02 | 1.1 ± 0.1 | 65 ± 1.4 |
| 5 | 0.64 ± 0.05 | 2.3 ± 0.1 | 97 ± 3.9 |
| 10 | 1.1 ± 0.1 | 3.0 ± 0.2 | >100 |
| 15 | 2.7 ± 0.3 | 15 ± 2.0 | >100 |
| 20 | 9.4 ± 0.8 | 27 ± 2.2 | >100 |
| 30 | 9.3 ± 0.9 | 32 ± 3.0 | >100 |

Table 9 presents data from the primary HCV replicon cell assay.

TABLE 9

| | PRIMARY ASSAY | | | |
|---|---|---|---|---|
| Compd # | CC50 (uM) | EC50 (uM) | EC90 (uM) | SI |
| 60 | 2.8 | 0.038 | 0.585 | 74.0 |
| 60 | 28.0 | 0.108 | 0.654 | 259.0 |
| 6 | 43.0 | 1.5 | 5.2 | 29.0 |
| 75 | 53.0 | 2.1 | 8.1 | 25.0 |
| 75 & 11 @10:1 | >100.0 | 1.3 | 5.0 | >77 |
| 7 | 20.0 | >10.0 | >10.0 | |
| 62 | >100.0 | >10.0 | >10.0 | |
| 11 | >100.0 | >10.0 | >10.0 | |

Table 10 presents data from the secondary HCV replicon cell assays using genotypes 1B and 1A.

TABLE 10

| | SECONDARY ASSAY, GENOTYPE 1B | | | | SECONDARY ASSAY, GENOTYPE 1A | | | |
|---|---|---|---|---|---|---|---|---|
| Compd # | CC50 (uM) | EC50 (uM) | EC90 (uM) | SI | CC50 (uM) | EC50 (uM) | EC90 (uM) | SI |
| 6 | >10.0 | 0.89 | 8.8 | >11.1 | >10.0 | 0.8 | 3.4 | >12.3 |
| 75 | 54.0 | 2.1 | 7.9 | 26.0 | 56.0 | 2.8 | 8.5 | 20.0 |

3.0 Synthesis of 2-(thiazol-2-ylcarbamoyl)phenyl methanesulfonate (11)

The compound, 2-(thiazol-2-ylcarbamoyl)phenyl methanesulfonate (11), was prepared according to the following synthetic scheme:

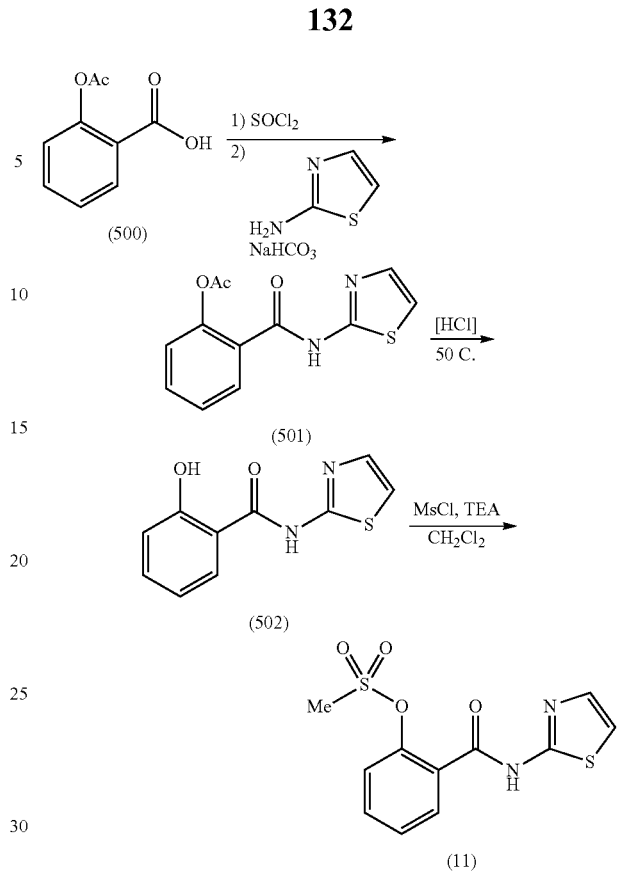

3.1 Synthesis of 2-(1,3-thiazol-2-ylcarbamoyl)phenyl acetate (501)

2-(Acetyloxy)-benzoic acid (500, 1.80 g, 10.0 mmol) was placed in a 250 mL round bottom flask equipped with a stirbar, vacuum adapter and septum. Ether (100 mL) and pyridine (1.00 mL, 12.4 mmol) were added to create a clear, colorless solution, which was cooled to zero in an ice bath before thionyl chloride (875 μL, 12.0 mmol) was added dropwise over ca. 30 sec. A thick white precipitate formed upon the addition of each drop. The reaction mixture was stirred for 90 minutes at 0° C. before being filtered through paper, and removing the solvents in vacuo. Sodium bicarbonate (3.42 g, 40.7 mmol) and 1,3-thiazol-2-amine (1.00 g, 10.0 mmol) were weighed into a 250 mL round bottom flask and water (30 mL) and ethyl acetate (30 mL) were added to form a colorless biphase, which was stirred rapidly. The crude acid chloride was suspended in ethyl acetate (10 mL) and added dropwise to the rapidly stirring biphase. The resulting biphase was capped lightly and stirred rapidly at room temperature for 2 hours. The biphase layers were separated, and the aqueous was extracted twice with ethyl acetate. The combined organics were washed with brine, dried with MgSO4, filtered, and concentrated to give 501 (1.36 g, 52%) as a colorless powder, which was used without purification.

Data for 501: $^1$H-NMR (400 MHz, DMSO-d6) d 12.58 (br s, 1H), 7.77 (dd, J=7.4, 1.8 Hz, 1H), 7.62 (ddd, J=7.7, 7.7, 1.8 Hz, 1H), 7.54 (d, J=3.6 Hz, 1H), 7.40 (ddd, J=7.7, 7.7, 1.4 Hz, 1H), 7.28 (d, J=3.6 Hz, 1H), 7.27 (dd, J=7.7. 1.4 Hz), and 2.22 (s, 3H) ppm; MS (ESI+) m/z (rel. intensity): 263.2 (5), 221.2 (40), 163.1 (10), 143.1 (10), 121.1 (40), 101.0 (100) m/z.

3.2 Synthesis of 2-hydroxy-N-1,3-thiazol-2-ylbenzamide (502)

2-(1,3-thiazol-2-ylcarbamoyl)phenyl acetate (501, 663.3 mg, 2.53 mmol) was added to a 25 mL round bottom flask equipped with a stirbar and a water-jacketed condenser. The headspace was replaced with dry nitrogen, and concentrated hydrochloric acid (15.0 mL) was added in a single portion. The suspension was heated to 50° C., and stirred well. The suspended solids dissolved to form a clear colorless solution before solids precipitate from the reaction mixture, which was then cooled in an ice bath, and the solids were filtered on a medium frit and washed with a large portion of water. The filter cake wash washed through the frit with methanol, collected, and the solvent was removed in vacuo to give 502 (481.5 mg, 86%) as a colorless solid.

Data for 502: $^1$H-NMR (400 MHz, DMSO-d6) d 12.07 (br s, 2H), 7.99 (dd, J=7.9, 1.5 Hz, 1H), 7.55 (d, J=3.8 Hz, 1H), 7.45 (br t, J=7.5 Hz), 7.27 (br d, J=2.7 Hz), and 6.9-7.05 Hz (m, 2H); MS (ESI+) m/z (rel. intensity): 221.2 (15), 121.1 (50), 101.0 (100).

3.3 Synthesis of 2-(1,3-thiazol-2-ylcarbamoyl)phenyl methanesulfonate (11)

2-hydroxy-N-1,3-thiazol-2-ylbenzamide (502, 267.1 mg, 1.21 mmol) was placed into a 10 mL round bottom flask equipped with a stirbar and a septum with a dry nitrogen inlet. Dichloromethane (5.0 mL) and triethylamine (500 μL, 3.59 mmol) were added to form a light pink solution. Methanesulfonyl chloride (100 μL, 1.3 mmol) in dichloromethane (ca. 1.0 mL) was added dropwise to the stirring solution over ca. 30 seconds, and the reaction was stirred at room temperature for ca. 20 minutes before being quenched into saturated NaHCO$_3$, and extracted with dichloromethane. The combined organics were washed with brine, dried over MgSO$_4$, filtered, and concentrated in vacuo. The crude product was recrystallized from hexanes/ethyl acetate to yield (284 mg, 78%) of 11 as a colorless crystalline solid. Example 11 (2-thiazol-2-ylcarbamoyl)phenyl methanesulfonate) has the empirical formula C$_{11}$H$_{10}$N$_2$O$_4$S and a molecular weight of 298.34.

Data for 11: mp=185.5-187.8° C.; $^1$H-NMR (400 MHz, DMSO-d6) d 12.63 (br s, 1H), 7.76 (dd, J=7.9, 1.7 Hz, 1H), 7.67 (ddd, J=7.8, 7.8, 1.7 Hz, 1H), 7.55 (d, J=3.5 Hz, 1H), 7.48-7.53 (m, 1H), 7.30 (d, J=3.5 Hz, 1H), and 3.35 (s, 3H) ppm; MS (ESI+) m/z (rel. intensity): 299.1 (90), 231.2 (20), 220.2 (100), 199.1 (20), 121.1 (10), 100.1 (20), 56.0 (40).

4.0 Synthesis of 2-hydroxy-N-(4-(methylsulfonyl)thiazol-2-yl)benzamide (60)

The compound, 2-hydroxy-N-[4-(methylsulfonyl)-1,3-thiazol-2-yl]benzamide (60), was prepared according to the following synthetic scheme:

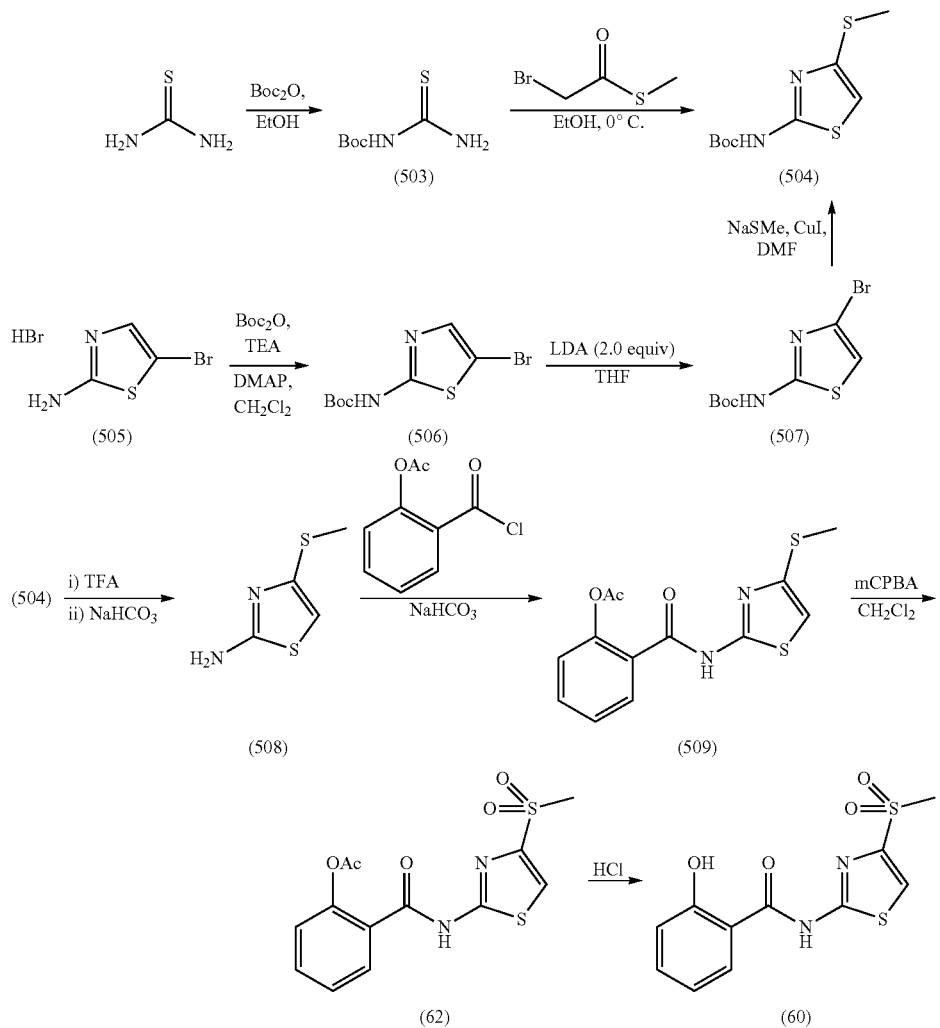

4.1 Synthesis of tert-butyl 4-(methylthio)thiazol-2-ylcarbamate (504)

N-tert-butoxycarbonylthiourea (503, 0.841 g, 4.77 mmol, prepared according to Schiavi, B.; Ahond, A.; Poupat, C.; Potier, P. *Synth. Commun.* 2002, 32, 1671) was suspended in ethanol (7.0 mL) and cooled in an ice bath. A solution of S-methyl bromoethanethioate (1.371 g, 5.0582 mmol, prepared according to Praveen Rao, P. N.; Amini, M.; Li, H.; Habeeb, A. G.; Knaus, E. E. *J. Med. Chem.* 2003, 46, 4872-82) in ethanol (7.0 mL) was added dropwise over 3 minutes. The suspension turned homogeneous at the end of the addition, the bath was removed, and the reaction was stirred at room temperature. The solvent was removed, and the crude material was partitioned between dichloromethane and water. The organics were washed with water and brine. The combined aqueous layers were back-extracted with dichloromethane, and the combined organics were dried with anhydrous $MgSO_4$, filtered, and concentrated in vacuo to an orange glass (stench). The crude material was adsorbed onto ca. 5 g silica gel with ethyl acetate, and flushed through a plug of silica gel with hexanes (discarded) followed by 9:1 hexanes:ethyl acetate. The eluent was evaporated in vacuo to yield 504 (589 mg, 50%) as a colorless solid.

Data for 504: $^1$H-NMR (400 MHz, $CDCl_3$) d 8.93 (br s, 1H), 6.40 (s, 1H), 2.45 (s, 3H), and 1.47 (s, 9H) ppm; $^{13}$C-NMR (100 MHz, $CDCl_3$) d 160.3, 151.3, 145.4, 105.7, 82.8 (br), 28.2, and 16.2 ppm; MS (ESI+) m/z (rel. intensity): 191.1 (100, $M-(CH_3)_2C=CH_2^+$), 173.1 (20), 147.1 (70), 120.0 (10), and 105.0 (10) m/z. MS (ESI–) m/z (rel. intensity): 245.2 (15, $M-H^-$), 171.1 (25), 145.1 (100), 103.0 (20), and 97.0 (20) m/z.

4.2 Synthesis of tert-butyl (5-bromo-1,3-thiazol-2-yl)carbamate (506)

5-bromo-1,3-thiazol-2-amine hydrobromide (505, 6.5150 g, 25.062 mmol) and 4-dimethylaminopyridine (69.9 mg, 0.572 mmol) were combined under an atmosphere of dry N2, and tetrahydrofuran (40 mL) and triethylamine (15 mL) were added to form a thick off-white suspension. A solution of di-tert-butyldicarbonate (6.0546 g, 27.742 mmol) in tetrahydrofuran (24 mL) was added to the above suspension, and the resulting slurry was stirred at room temperature for 4 h. The reaction mixture was then poured onto water (100 mL), and the aqueous was extracted with ethyl acetate. The combined organics were washed with saturated $NaHCO_3$ solution, brine, dried over MgSO4, filtered, and the solvent was removed in vacuo. The crude product was adsorbed onto silica gel, and eluted through a plug of silica gel with 9:1 hexanes:ethyl acetate. The eluent was collected, and evaporated to give 506 (5.42 g, 78%) as a colorless crystalline solid.

Data for 506: $^1$H NMR (400 MHz, DMSO-d6) d 12.75 (br s, 1H), 7.44 (s, 1H), and 1.48 (s, 9H) ppm. $^{13}$C NMR (100 MHz, DMSO-$d_6$) δ 160.1, 152.9 (br), 139.0, 100.5, 81.7, and 27.8 ppm. MS (ESI+) m/z (rel. intensity): 225.1 (100, $M^{81}Br—(CH_3)_2C=CH_2^+$), 223.1 (100, $M^{79}Br—(CH_3)_2C=CH_2^+$).

4.3 Synthesis of tert-butyl (4-bromo-1,3-thiazol-2-yl)carbamate (507)

Tetrahydrofuran (160 mL) and N,N-diisopropylamine (14 mL, 97 mmol) were combined in a 3-neck 500 mL RBF equipped with a stirbar, septum, and an internal temperature probe. The resulting solution was cooled to 0.8° C., and n-butyllithium in hexanes (2.50 M, 38 mL, 95 mmol) was added slowly over ca. 5 min to produce a light yellow solution ($T_{int}$ max=10° C.), which was stirred and allowed to re-cool to near 0° C. A solution of tert-butyl (5-bromo-1,3-thiazol-2-yl) carbamate, 506 (8.74 g, 31.3 mmol) in tetrahydrofuran (30.0 mL) was added dropwise to the above solution over 16 min ($T_{int}$ varied from 0.9° C. to a maximum of 7° C.). The now deep brown reaction mixture was stirred for 15 min before being quenched with water (13 mL), and stirred for an additional 5 minutes. Aqueous saturated $NH_4Cl$ (250 mL) and ethyl acetate (250 mL) were added, and the layers were separated. The aqueous was extracted with ethyl acetate, and the combined organics were washed with brine, dried with $MgSO_4$, filtered, and concentrated in vacuo. The crude material was adsorbed onto silica gel with ethyl acetate, and elute through a plug of silica gel with 2 liters of 9:1 hex:EtOAc The eluent was collected, and the solvents were removed to give 507 (8.41 g, 96%) as a colorless solid.

Data for 507: $^1$H NMR (400 MHz, DMSO-d6) d 12.75 (br s, 1H), 7.24 (s, 1H), and 1.48 (s, 9H) ppm. $^{13}$C NMR (400 MHz, $CDCl_3$) d 160.6, 152.7 (br), 119.8, 110.6, 81.7, and 27.9 ppm. MS (ESI+) m/z (rel. intensity): 225.1 (100, $M^{81}Br—(CH_3)_2C=CH_2^+$), 223.1 (100, $M^{79}Br—(CH_3)_2C=CH_2^+$).

4.4 Alternate synthesis of tert-butyl (4-methylthio-1,3-thiazol-2-yl)carbamate (504)

tert-Butyl (4-bromo-1,3-thiazol-2-yl)carbamate (507, 3.9575 g, 14.177 mmol), copper(I) iodide (2.7718 g, 14.554 mmol), and sodium methylthiolate (5.0242 g, 71.682 mmol) were combined in a 100 mL flask equipped with a stirbar and a water-jacketed condenser with a septum. The headspace was exchanged for dry nitrogen, and N,N-dimethylformamide (26 mL) was added. The reaction turned canary yellow, and then faded to a dull grey-pink suspension, and was stirred at room temperature for ca. 1 min before lowering into a 136° C. oilbath set to 140° C., and stirred. Over the first 5-10 min of heating, the color faded to a light yellow, and the reaction became homogenous. Out gassing/boiling was observed when stirring was stopped. The reaction was cooled to room temperature after 15 h at 140° C., and HPLC analysis showed complete consumption of starting material. The reaction mixture was diluted with ethyl acetate (ca. 200 mL) and filtered through a pad of celite, eluting with ethyl acetate. The combined organics were washed with 1:1 1 M HCl/saturated $NH_4Cl$ solution (250 mL), which resulted in a thick emulsion. The entire mixture was then filtered through amorphous cellulose, and the layers were separated. The organics were than washed with 0.5 M HCl, and saturated $NaHCO_3$ solution. Another very fine powder drops out of solution upon treatment with base. The suspension was again filtered through celite, and the resulting solution was washed with brine, dried with $MgSO_4$, filtered, and concentrated in vacuo to give a green oil (3.17 g). The crude product was adsorbed onto ca. 15 g silica with EtOAc, and dried in vacuo, and eluted through a pad of silica gel (ca. 80 g) with 500 mL hexanes (discarded) and 2 liters of 9:1 hexanes/ethyl acetate, which was concentrated in vacuo to give 504 (2.41 g, 69%) as an off-white solid.

Data for 504 is given above.

4.5 Synthesis of 4-(methylthio)-1,3-thiazol-2-amine (508)

tert-Butyl [4-(methylthio)-1,3-thiazol-2-yl]carbamate (504, 3.17 g, 12.9 mmol) was dissolved in methylene chloride (130 mL), and trifluoroacetic acid (54 mL) was added to produce a bright yellow solution. The solution was lightly capped and stirred at room temperature for 8 hours, at which point the reaction was complete. The solvents were removed in vacuo and the resultant thick oil was suspended in 0.1 M HCl (50 mL), and the solvent was removed. This was repeated once, and the resulting solids were suspended in ethyl acetate (20 mL) and evaporated to give a finely divided, free-flowing pink solid (2.0 g). The solids were re-suspended in ethyl acetate (20 mL), sonicated, and filtered on a medium frit, washing with ethyl acetate (ca. 30 mL). The lavender solids were partitioned solids between saturated NaHCO$_3$ solution (100 mL) and dichloromethane (100 mL). The layers were separated, and the aqueous layer was extracted once with dichloromethane. The combined organics were then washed with brine, dried with anhydrous MgSO$_4$, filtered, and concentrated in vacuo to give 508 (1.33 g, 71%) as a dark oil, which solidified to a crystalline solid upon point cooling with dry ice, and letting stand.

Data for 508: $^1$H-NMR (400 MHz, DMSO-d6) d 7.06 (br s, 2H), 6.11 (s, 1H), and 2.36 (s, 3H) ppm; $^{13}$C-NMR (100 MHz, DMSO-d$_6$) d 168.5, 144.7, 97.37, and 14.7 ppm; MS (ESI+) m/z (rel. intensity): 147.1 (100, M+H$^+$), 132.0 (20), and 105.0 (40).

4.6 Synthesis of 2-{[4-(methylthio)-1,3-thiazol-2-yl]carbamoyl}phenyl acetate (509)

4-(Methylthio)-1,3-thiazol-2-amine (508, 672 mg, 4.60 mmol) was dissolved in tetrahydrofuran (10.0 mL) to give a watermelon colored solution, and cooled to zero ° C. A solution of acetylsalicyloyl chloride (0.9915 g) in tetrahydrofuran (1.4 mL) was added dropwise over 1 minute, the bath was removed, and the reaction was stirred while allowing the reaction to warm to room temperature over ca. 40 minutes. Triethylamine (0.670 mL, 4.81 mmol) was added dropwise over 3 minutes to produce a dark suspension that was stirred for 15 hours. The solids were removed from the slurry by filtering on a medium frit, the solids were washed with THF (ca. 20 mL), and the resulting solution was concentrated, dissolved in ethyl acetate, filtered through a plug of magnesol to remove polar colored impurities, and concentrated to give an orange crystalline solid (1.35 g). This crude material was adsorbed onto silica gel with ethyl acetate, and purified by MPLC (eluting 1 liter each 6:1, 4:1, 3:1, and 2:1 Hex:EtOAc). Fractions were pooled and evaporated to give 509 (660.8 mg, 47%) as a near colorless solid.

Data for 509: $^1$H-NMR (400 MHz, DMSO-d6) d 12.69 (br s, 1H), 7.77 (dd, J=7.8, 1.4 Hz, 1H), 7.62 (ddd, J=7.8, 7.8, 1.4 Hz, 1H), 7.40 (ddd, J=7.8, 7.8, 1.4 Hz, 1H), 7.27 (dd, J=8.0, 1.4 Hz, 1H), 6.87 (s, 1H), 2.48 (s, 3H), and 2.22 (s, 3H) ppm; $^{13}$C-NMR (100 MHz, DMSO-d6) d 168.8, 163.9, 158.3, 148.5, 145.2, 132.7, 129.5, 126.5, 125.8, 123.3, 105.4, 20.7, and 15.0 ppm.; MS (ESI+) m/z (rel. intensity): 331.2 (20, M+Na$^+$), 309.3 (25, M+H$^+$), 267.3 (70), 189.2 (30), 147.2 (100), 121.1 (40), 100.1 (20), and 83.1 (65) m/z. MS (ESI−) m/z (rel. intensity): 265.3 (80, M−H$^-$).

4.7 Synthesis of 2-{[4-(methylsulfonyl)-1,3-thiazol-2-yl]carbamoyl}phenyl acetate (62)

2-{[4-(Methylthio)-1,3-thiazol-2-yl]carbamoyl}phenyl acetate (509, 201.1 mg, 0.6521 mmol) was dissolved in methylene chloride (21 mL), and m-chloroperbenzoic acid (317.1 mg, 1.378 mmol) was added in a single portion. The reaction was capped and stirred at room temperature for 100 minutes, when HPLC analysis of the mixture showed complete conversion to the desired sulfone. The reaction was quenched with 20% aq. Na$_2$S$_2$O$_3$ (20 mL), stirred 5 min, and the layers were separated. The organics were washed with saturate NaHCO$_3$ solution and brine, dried with anhydrous MgSO$_4$, filtered, and concentrated in vacuo to give a colorless white solid (211.0 mg). The crude product was recrystallized from refluxing ethyl acetate/hexanes (5.0:2.0 mL), filtered, washed with hexanes, and dried in vacuo to give 62 (133.4 mg, 61%) a colorless crystalline solid.

Data for 62: $^1$H-NMR (400 MHz, DMSO-d6) d 13.19 (br s, 1H), 8.11 (s, 1H), 7.82 (d, J=7.8 Hz, 1H), 7.65 (dd, J=7.8, 7.8 Hz, 1H), 7.42 (dd, J=7.8, 7.8 Hz, 1H), 7.29 (d, J=7.8 Hz, 1H), 3.23 (s, 3H), and 2.23 (s, 3H) ppm; $^{13}$C-NMR (100 MHz, DMSO-d6) d 168.8, 164.8, 160.1, 148.6, 148.3, 133.1, 129.6, 126.0, 125.9, 123.4, 120.2, 42.0, and 20.7 ppm; MS (ESI+) m/z (rel. intensity): 341.1 (10, M+H$^+$), 299.1 (20), 163.2 (15), 121.1 (100), 100.1 (15), and 83.0 (50) m/z. MS (ESI−) m/z (rel. intensity): 339.2 (10, M−H$^-$) m/z.

4.8 Synthesis of 2-hydroxy-N-[4-(methylsulfonyl)-1,3-thiazol-2-yl]benzamide (60)

2-{[4-(methylsulfonyl)-1,3-thiazol-2-yl]carbamoyl}phenyl acetate (62, 118.2 mg, 0.3473 mmol) was suspended in conc. hydrochloric acid (2.0 mL) and stirred rapidly. The slurry become homogenous momentarily, and then re-precipitates. The suspension was stirred rapidly at 50° C. for 16 hours before cooling, and filtering on a fine fritted funnel. The solids were washed with water (ca. 5 mL), and dried in vacuo to give 60 as a colorless powder.

Data for 60: m.p.=231-235° C. (sealed tube); $^1$H-NMR (400 MHz, DMSO-d6) d 12.30 (br s, 1H), 11.64 (br s, 1H), 8.12 (s, 1H), 7.96 (dd, J=7.6, 1.6 Hz, 1H), 7.65 (ddd, J=7.6, 7.6, 1.6 Hz, 1H), 7.07 (br d, J=7.6 Hz, 1H), 7.01 (br dd, J=7.6, 7.6 Hz, 1H), and 3.25 (s, 3H) ppm; $^{13}$C-NMR (100 MHz, DMSO-d6) d 165.0, 159.4, 157.3, 148.3, 134.8, 130.3, 120.5, 119.8, 117.2, 116.4, and 42.0 ppm. MS (ESI+) m/z (rel. intensity): 321.3 (30, M+Na$^+$), 299.1 (10, M+H$^+$), 242.1 (10), 201.1 (30), 179.1 (20), 121.1 (100), 100.1 (20), and 56.0 (20) m/z. MS (ESI−) m/z (rel. intensity): 297.2 (100, M−H$^-$) m/z.

5.0 General procedures for the synthesis of 4-hydroxy-N-[4-(methylsulfonyl)-1,3-thiazol-2-yl]benzamide (84) and 3-hydroxy-N-[4-(methylsulfonyl)-1,3-thiazol-2-yl]benzamide (87)

The compounds 4-hydroxy-N-[4-(methylsulfonyl)-1,3-thiazol-2-yl]benzamide (84) and 3-hydroxy-N-[4-(methylsulfonyl)-1,3-thiazol-2-yl]benzamide (87), were prepared according to the following general synthetic scheme:

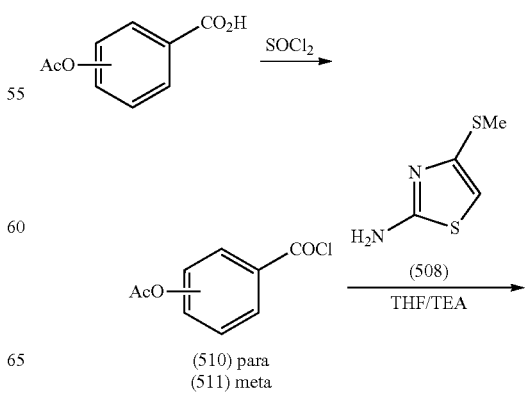

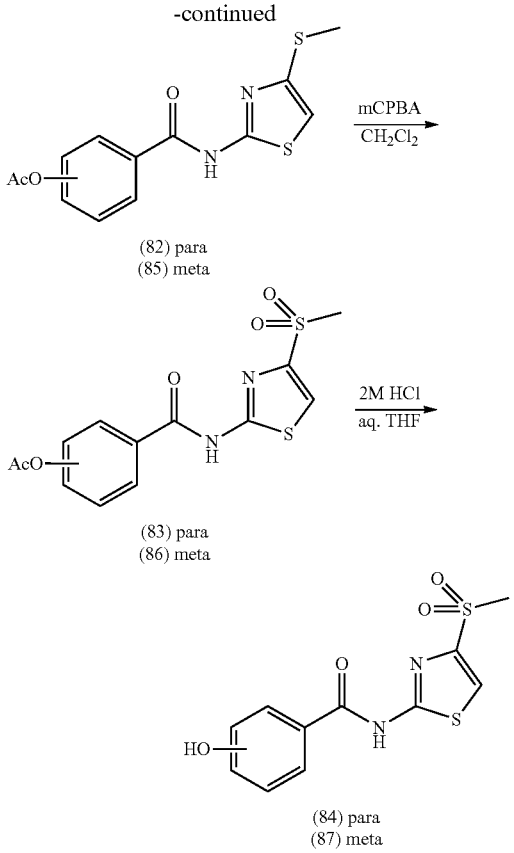

(82) para
(85) meta

(83) para
(86) meta

(84) para
(87) meta

5.1 Synthesis of 4-(chlorocarbonyl)phenyl acetate (510)

Thionyl chloride (11.1 mL, 15.3 mmol) was added to 4-acetoxybenzoic acid (2.50 g, 13.9 mmol), and the reaction was warmed to reflux. The reaction was cooled after heating for 3.5 hours, and concentrated in vacuo to give a colorless oil. Toluene was added to the residue and the mixture was concentrated in vacuo to remove any residual thionyl chloride. This process was repeated twice more to give 510 (2.54 g, 92%) as a colorless oil. This material was used in the next step without additional purification.

Data for 510: $^1$H-NMR (400 MHz, CDCl$_3$) d 8.18 (d, J=8.9 Hz, 2H), 7.29 (d, J=8.9 Hz, 2H), 2.36 (s, 3H) ppm.

5.2 Synthesis of 3-(chlorocarbonyl)phenyl acetate (511)

Using the above procedure, reaction of with thionyl chloride (11.1 mL, 15.3 mmol) and 3-acetoxybenzoic acid (2.50 g, 13.9 mmol) gave 511 (2.72 g, 99%) as a colorless oil. This material was used in the next step without additional purification.

Data for 511: $^1$H-NMR (400 MHz, CDCl$_3$) δ 8.03 (ddd, J=8, 2, 1 Hz, 1H), 7.87 (t, J=2 Hz, 1H), 7.52-7.60 (m, 1H), 7.46 (ddd, J=8, 2, 1 Hz, 1H), 2.37 (s, 3H) ppm.

5.3 Synthesis of 4-{[4-(methylthio)-1,3-thiazol-2-yl]carbamoyl}phenyl acetate (82)

Into a solution of 510 (0.815 g, 4.10 mmol) and dry THF (20.0 mL) was added a solution of triethylamine (0.572 mL, 4.10 mmol) and dry THF (5.00 mL), followed by a solution of 508 (0.500 g, 3.42 mmol) dissolved in dry THF (15.0 mL). The reaction was stirred at room temperature. After stirring overnight, the reaction was concentrated in vacuo. The residue was partitioned between a saturated aqueous sodium bicarbonate and dichloromethane. The dichloromethane layer was washed a second time with the saturated sodium bicarbonate solution and than twice with aq. 1 M HCl. The dichloromethane layer was dried over anhydrous magnesium sulfate and concentrated in vacuo to give crude 82 (1.15 g, >100%) as a brown solid. The crude product was suspended in diethyl ether, stirred and filtered. The filter pad was washed with ether several times, and dried in vacuo to give 82 (0.692 g, 63%) as a light brown solid.

Data for 82: mp=185.7-188.7° C.; $^1$H-NMR (400 MHz, DMSO-d$_6$) δ 12.8 (s, 1H), 8.14 (d, J=8.9 Hz, 2H), 7.32 (d, J=8.9 Hz, 2H), 6.89 (s, 1H), 2.50 (s, 3H), 2.31 (s, 3H) ppm; MS (ESI+) m/z (rel. intensity): 100.1 (37), 122.2 (98.3), 163.2 (49), 309.2 (100), 331.2 (29) m/z. MS (ESI−) m/z (rel. intensity): 111.0 (16), 203.2 (31), 307.2 (100).

5.4 Synthesis of 3-{[4-(methylthio)-1,3-thiazol-2-yl]carbamoyl}phenyl acetate (85)

Into a solution of 511 (0.815 g, 4.10 mmol) and dry THF (25.0 mL) was added triethylamine (0.572 mL, 4.10 mmol), followed by a solution of the 508 (0.500 g, 3.42 mmol) dissolved in dry THF (10.0 mL). The reaction was stirred at room temperature. After stirring overnight, the reaction was concentrated in vacuo. The residue was dissolved in ethyl acetate and washed once with water, three times with saturated aqueous. sodium bicarbonate solution, and once with brine. The ethyl acetate solution was dried over anhydrous sodium sulfate and concentrated in vacuo to give crude 85 (1.28 g, >100%) as a red foam. The crude product was dissolved in dichloromethane. Silica gel was added to the dichloromethane solution and the suspension was concentrated in vacuo. The residue was loaded on top of a 90 g silica gel cartridge and eluted down the column using a solution of 20% ethyl acetate in hexane. Appropriate fractions of the major product were combined and concentrated in vacuo to give 85 (0.614 g, 58%) as a tan solid. This material was used in the next step without further purification.

Data for 85: $^1$H-NMR (400 MHz, DMSO-d$_6$) δ 12.8 (s, 1H), 8.01 (d, J=8 Hz, 1H), 7.87 (t, J=2 Hz, 1H), 7.60 (t, J=8 Hz, 1H), 7.42 (ddd, J=8, 2, 1 Hz, 1H), 6.90 (s, 1H), 2.50 (s, 3H), 2.32 (s, 3H) ppm.

5.5 Synthesis of 4-{[4-(methylsulfonyl)-1,3-thiazol-2-yl]carbamoyl}phenyl acetate (83)

A solution of m-chloroperbenzoic acid (1.0 g, 6.0 mmol, maximum 77%) dissolved in dichloromethane (30 mL) was added to a suspension of 82 (0.63 g, 2.0 mmol) in dichloromethane (60 mL). The reaction became homogeneous and the dark brown solution became lighter with time. After 1.25 hours, saturated aqueous sodium thiosulfate was added to the reaction and the reaction mixture was stirred vigorously for 20 minutes. The yellow mixture was diluted with water and the resulting layers separated. The organic layer was washed twice with saturated aqueous sodium bicarbonate, once with brine, dried with anhydrous sodium sulfate and concentrated in vacuo to give a beige solid. The crude product was recrystallized from 50% ethyl acetate/hexane (220 mL). After 4 days the suspension was filtered, the filter pad was washed with hexanes and then diethyl ether, and dried in vacuo at 55° C. overnight to give 83 (0.20 g, 30%) as a light orange solid.

Concentration of the filtrate in vacuo followed by triturating the resulting residue with diethyl ether and filtering off the resulting solid yielded an additional 45 mg of 83 as a tan solid.

Data for 83: m.p.=242-246° C. (dec); $^1$H-NMR (400 MHz, DMSO-d6) δ 13.2 (s, 1H), 8.18 (d, J=8.7 Hz, 2H), 8.13 (s, 1H), 7.34 (d, J=8.7 Hz, 2H), 3.25 (s, 3H), and 2.32 (s, 3H), ppm; MS (ESI+) m/z (rel. intensity): 121.1 (40), 163.2 (50), 230.8 (10), 341.2 (100), 363.2 (70) m/z; MS (ESI−) m/z (rel. intensity): 339.3 (100).

5.6 Synthesis of 3-{[4-(methylsulfonyl)-1,3-thiazol-2-yl]carbamoyl}phenyl acetate (86)

Using the above procedure for example 83, m-chloroperbenzoic acid (1.0 g, 6.0 mmol, maximum 77%) dissolved in dichloromethane (30 mL) and 85 (0.61 g, 2.0 mmol) dissolved in dichloromethane (30 mL) gave crude 86 as a white solid. The crude product was stirred in diethyl ether (30 mL) for 30 minutes, filtered and air dried to give 86 (0.59 g, 87%) as a white solid.

Data for 86: m.p.=209-212° C.; $^1$H-NMR (400 MHz, DMSO-d6) δ 13.2 (s, 1H), 8.13 (s, 1H), 8.05 (d, J=8 Hz, 1H), 7.91 (t, J=2 Hz, 1H), 7.62 (t, J=8 Hz, 1H), 7.45 (d, J=8 Hz, 1H), 3.26 (s, 3H), and 2.32 (s, 3H), ppm; MS (ESI+) m/z (rel. intensity): 121.1 (20), 163.2 (20), 299.2 (25), 341.2 (100), 363.3 (40), 380.8 (10), 530.5 (10), 719.3 (5), 743.3 (5) m/z; MS (ESI−) m/z (rel. intensity): 339.3 (100).

5.7 Synthesis of 4-hydroxy-N-[4-(methylsulfonyl)-1,3-thiazol-2-yl]benzamide (84)

2 M hydrochloric acid (3.0 mL) was added to a suspension of 83 (0.12 g, 0.35 mmol) in tetrahydrofuran (3.0 mL), and the resulting suspension was warmed to reflux. The reaction became homogeneous upon heating. After refluxing for 1.5 h, the reaction was allowed to cool to room temperature, and then partitioned between diethyl ether and water. The ether layer was washed with water, saturated aqueous sodium bicarbonate, and brine. The ether layer was dried with anhydrous sodium sulfate and concentrated in vacuo. The residue triturated with ethyl acetate, the solvent was removed under a stream of nitrogen, and the resulting solid was dried in vacuo at 55° C. to give 84 (0.086 g, 82%) as a light yellow solid.

Data for 84: mp=253-255° C. (dec). $^1$H NMR (400 MHz, DMSO-d6) δ 12.9 (s, 1H), 10.4 (s, 1H), 8.07 (s, 1H), 8.03 (d, J=8.7 Hz, 2H), 6.89 (d, J=8.7 Hz, 2H), and 3.24 (s, 3H) ppm. MS (ESI+) m/z (rel. intensity): 121.1 (100), 299.3 (40), 321.2 (25), 355.3 (5) m/z. MS (ESI−) m/z (rel. intensity): 297.3 (100).

5.8 Synthesis of 3-hydroxy-N-[4-(methylsulfonyl)-1,3-thiazol-2-yl]benzamide (87)

Using the above procedure for example 84, compound 86 (0.36 g, 1.0 mmol) dissolved in tetrahydrofuran (10 mL) and 2 M hydrochloric acid (10 mL) gave 87 (0.29 g, 91%) as a white solid after the ether layer was concentrated in vacuo.

Data for 87: m.p.=258-259° C. (dec); $^1$H-NMR (400 MHz, DMSO-d6) δ 13.1 (s, 1H), 9.88 (s, 1H), 8.11 (s, 1H), 7.59 (d, J=8 Hz, 1H), 6.47 (s, 1H), 7.35 (t, J=8 Hz, 1H), 7.05 (dd, J=8, 2 Hz, 1H), and 3.25 (s, 3H) ppm; MS (ESI+) m/z (rel. intensity): 218.3 (10), 299.3 (100), 321.2 (40) m/z; MS (ESI−) m/z (rel. intensity): 297.3 (100).

6.0 General procedures for the synthesis of 4-hydroxy-N-[5-(methylsulfonyl)-1,3-thiazol-2-yl]benzamide (80) and 3-hydroxy-N-[5-(methylsulfonyl)-1,3-thiazol-2-yl]benzamide (81)

The compounds 4-hydroxy-N-[5-(methylsulfonyl)-1,3-thiazol-2-yl]benzamide (80) and 3-hydroxy-N[5-(methylsulfonyl)-1,3-thiazol-2-yl]benzamide (81) were prepared according to the following general synthetic scheme:

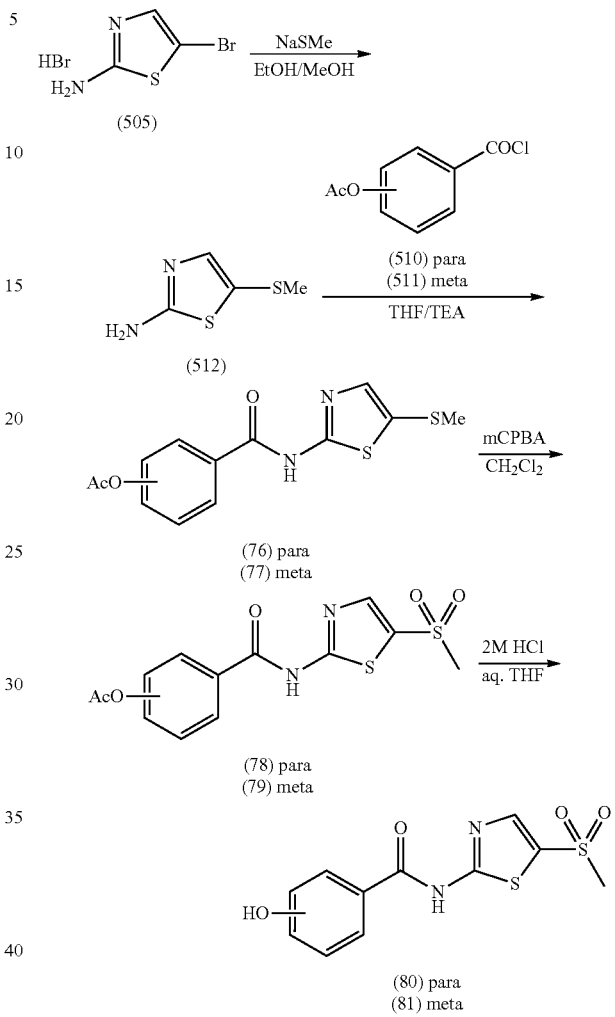

6.1 Synthesis of 5-(methylthio)-1,3-thiazol-2-amine (512)

A solution of sodium thiomethoxide (1.09 g, 14.8 mmol) dissolved in methanol (18.0 mL) was added to a suspension of 2-amino-5-bromothiazole monohydrobromide 505 (2.50 g, 14.0 mmol) in anhydrous ethanol (18.0 mL) over 5 minutes. The reaction became homogeneous. A second solution of sodium thiomethoxide (1.09 g, 14.8 mmol) dissolved in methanol (12.0 mL) was added to the reaction. The reaction was warmed to 45° C. for 40 minutes then the heat was removed and the reaction was allowed to stir at room temperature overnight, when thin layer chromatography (1:1 EtOAc/Hexane) indicated most of the starting material consumed along with the formation of a new product. Additional sodium thiomethoxide (0.20 g, 2.85 mmol) was added to the reaction and the reaction was re-warmed to 50° C. After heating for 2 hours, the reaction was cooled to room temperature and concentrated in vacuo. The residue was dissolved in dichloromethane and washed three times with water, once with brine, dried over anhydrous sodium sulfate and concentrated in vacuo to give 512 (1.12 g, 55%) as an orange solid.

Data for 512: $^1$H-NMR (400 MHz, DMSO-$d_6$) δ 7.20 (s, 2H), 6.97 (s, 1H), 2.29 (s, 3H) ppm.

6.2 Synthesis of 4-{[5-(methylsulfanyl)-1,3-thiazol-2-yl]carbamoyl}phenyl acetate (76)

Following the procedure for the synthesis of example 82, intermediate 510 (0.815 g, 4.10 mmol) dissolved in dry THF (25.0 mL), triethylamine (0.572 mL, 4.10 mmol), and 512 (0.500 g, 3.42 mmol) dissolved in dry THF (10.0 mL) gave 76 (0.887 g, 84%) as a tan solid.

Data for 76: m.p.=193.3-195.5° C.; $^1$H-NMR (400 MHz, DMSO-$d_6$) δ 12.8 (br. s., 1H), 8.13 (d, J=8.71 Hz, 2H), 7.58 (s, 1H), 7.32 (d, J=8.71 Hz, 2H), 2.46 (s, 3H), 2.31 (s, 3H) ppm; MS (ESI+) m/z (rel. intensity): 121.0 (100), 163.2 (48), 309.2 (34) m/z. MS (ESI−) m/z (rel. intensity): 292.2 (100), 307.3 (48).

6.3 Synthesis of 3-{[5-(methylsulfanyl)-1,3-thiazol-2-yl]carbamoyl}phenyl acetate (77)

Following the procedure for the synthesis of example 85, intermediate 511 (0.815 g, 4.10 mmol) dissolved in dry THF (25.0 mL), triethylamine (0.572 mL, 4.10 mmol), and 512 (0.500 g, 3.42 mmol) dissolved in dry THF (10.0 mL) gave 77 (0.681 g, 65%) as a tan solid.

Data for 77: m.p.=135.2-136.2° C.; $^1$H-NMR (400 MHz, DMSO-$d_6$) δ 12.8 (s, 1H), 7.96-8.03 (m, 1H), 7.86 (t, J=2 Hz, 1H), 7.57-7.63 (m, 2H), 7.43 (ddd, J=8, 2, 1 Hz, 1H), 2.47 (s, 3H), 2.32 (s, 3H) ppm; MS (ESI+) m/z (rel. intensity): 121.0 (40), 163.2 (100), 309.2 (85), 331.2 (11) m/z; MS (ESI−) m/z (rel. intensity): 292.3 (100), 307.3 (49).

6.4 Synthesis of 4-{[5-(methylsulfonyl)-1,3-thiazol-2-yl]carbamoyl}phenyl acetate (78)

A solution of m-chloroperbenzoic acid (0.611 g, 2.73 mmol, maximum 77%) dissolved in dichloromethane (10.0 mL) was added drop wise over 15 minutes to a solution of 76 (0.841 g, 2.73 mmol) dissolved in dichloromethane (35.0 mL), and the reaction was stirred at room temperature for 1.25 hours. A second solution of m-chloroperbenzoic acid (0.611 g, 2.73 mmol) dissolved in dichloromethane (10.0 mL) was added to the reaction over 15 minutes, and the resulting solution was stirred for an additional 2.5 hours at room temperature. The reaction was partitioned between dichloromethane and saturated aq. sodium thiosulfate. The organic layer was washed with saturated aq. sodium thiosulfate, twice with saturated aq. sodium bicarbonate, and once with brine. The dichloromethane layer was concentrated in vacuo (without drying) to give crude 78 (0.80 g, 86%). The crude product was stirred with chloroform (250 mL) and the suspension filtered. The pad was washed once with chloroform and air dried to give 78 (0.559 g, 60%) as a white solid.

Data for 78: m.p.=279.6-280.6° C.; $^1$H-NMR (400 MHz, DMSO-$d_6$) δ 13.3 (br. s., 1H), 8.20 (s, 1H), 8.18 (d, J=8.71 Hz, 2H), 7.35 (d, J=8.71 Hz, 2H), 3.39 (s, 3H), 2.32 (s, 3H) ppm; MS (ESI+) m/z (rel. intensity): 121.0 (100), 163.2 (72), 341.2 (63), 363.2 (59) m/z; MS (ESI−) m/z (rel. intensity): 259.3 (17), 339.3 (100).

6.5 Synthesis of 3-{[5-(methylsulfonyl)-1,3-thiazol-2-yl]carbamoyl}phenyl acetate (79)

A solution of m-chloroperbenzoic acid (0.458 g, 2.04 mmol, maximum 77%) dissolved in dichloromethane (8.0 mL) was added drop wise over 15 minutes to a solution of 77 (0.630 g, 2.04 mmol) dissolved in dichloromethane (25.0 mL). The reaction was stirred at room temperature for 1.25 hours. A second solution of m-chloroperbenzoic acid (0.458 g, 2.04 mmol) dissolved in dichloromethane (8.0 mL) was then added to the reaction over 10 minutes, and stirred for an additional 4.5 hours at room temperature. The reaction was then partitioned between dichloromethane and saturated aqueous sodium thiosulfate. The organic layer was washed again with a saturated aqueous sodium thiosulfate, twice with saturated aqueous sodium bicarbonate and once with brine. The dichloromethane layer was dried over magnesium sulfate and concentrated in vacuo to give crude 79 (0.704 g, >100%), which was contaminated with traces of residual 3-chlorobenzoic acid. The crude product was re-dissolved in ethyl acetate and washed three times with a saturated aq. sodium bicarbonate, dried using magnesium sulfate and concentrated in vacuo to give a tan solid. The residue was dissolved in THF, and the light brown solution was filtered through a plug of Magnesol. the filter pad was washed well with THF, and the colorless filtrate was concentrated in vacuo to give 79 (0.530 g, 76%) as a white solid.

Data for 79: m.p.=186.5° C. (dec); $^1$H-NMR (400 MHz, DMSO-$d_6$) δ 13.4 (s, 1H), 8.20 (s, 1H), 8.04 (d, J=8 Hz, 1H), 7.91 (t, J=2 Hz, 1H), 7.63 (t, J=8 Hz, 1H), 7.47 (ddd, J=8, 2, 1 Hz, 1H), 3.40 (s, 3H), 2.32 (s, 3H) ppm; MS (ESI+) m/z (rel. intensity): 121.0 (31), 163.2 (100), 341.2 (75), 363.2 (24) m/z; MS (ESI−) m/z (rel. intensity): 259.2 (22), 339.2 (100).

6.6 Synthesis of 4-hydroxy-N-[5-(methylsulfonyl)-1,3-thiazol-2-yl]benzamide (80)

2 M hydrochloric acid (45.0 mL) was added to a suspension of 78 (0.439 g, 1.29 mmol) in tetrahydrofuran (20.0 mL), and the suspension was warmed to reflux. The reaction became homogeneous upon heating. After refluxing for 4 hours, the reaction was allowed to cool to room temperature, and stood at room temperature overnight before the reaction was filtered. The filter pad was washed with water then dried in vacuo at 70° C. to give 80 (0.2489 g, 64.6%) as a white crystalline solid.

Data for 80: m.p.=ca. 242° C. (dec). The decomposed solids then melt at 252.5-255.5° C.; $^1$H-NMR (400 MHz, DMSO-$d_6$) δ 13.1 (br. s., 1H), 10.5 (s, 1H), 8.22 (s, 1H), 8.09 (d, J=8.71 Hz, 2H), 6.96 (d, J=8.71 Hz, 2H), 3.43 (s, 3H) ppm; MS (ESI+) m/z (rel. intensity): 121.1 (100), 299.2 (10), 321.1 (4) m/z; MS (ESI−) m/z (rel. intensity): 177.2 (16), 217.2 (24), 297.2 (100).

6.7 Synthesis of 3-hydroxy-N-[5-(methylsulfonyl)-1,3-thiazol-2-yl]benzamide (81)

2 M hydrochloric acid (40.0 mL) was added to a suspension of 79 (0.370 g, 1.09 mmol) in tetrahydrofuran (17.0 mL), and the reaction was warmed to reflux. The reaction became homogeneous upon heating. After refluxing for 4 hours, the reaction was allowed to cool to room temperature, and concentrated in vacuo. The residue was suspended in water and filtered. The filter pad was washed with water, air dried, and then re-dissolved in a minimum amount of warm THF. Water was added to the warm THF solution until the solution turned turbid, and the resulting mixture was allowed to cool to room temperature. Additional water was added, and a white solid formed on standing. The crystalline product was filtered, and the filter pad was washed with water, and dried in vacuo at 70° C. to give 81 (0.182 g, 56%) as a white crystalline solid.

Data for 81: m.p.=271.1-272.3° C.; $^1$H-NMR (400 MHz, DMSO-$d_6$) δ 13.2 (s, 1H), 9.91 (s, 1H), 8.19 (s, 1H), 7.58 (d, J=8 Hz, 1H), 7.46 (t, J=2 Hz, 1H), 7.37 (t, J=8 Hz, 1H), 7.06 (dd, J=8, 2 Hz, 1H), 3.39 (s, 3H) ppm; MS (ESI+) m/z (rel. intensity): 100.1 (42) 121.1 (100), 299.2 (44), 321.1 (8) m/z; MS (ESI−) m/z (rel. intensity): 217.2 (29), 297.2 (100).

7.0 Synthesis of 2-hydroxy-N-(5-(methylsulfonyl)thiazol-2-yl)benzamide (6)

The compound, 2-hydroxy-N-(5-(methylsulfonyl)thiazol-2-yl)benzamide (6), was prepared according to the following synthetic scheme:

dried over anhydrous MgSO$_4$. Product purification through flash column chromatography gave the required product, 2-amino-5-methylthiothiazole 512 (1.35 g, 25.2% yield), as a brown solid.

Data for 512: TLC (silica gel) R$_f$=0.2 (1:1, Hex:EtOAc); $^1$H-NMR (CDCl$_3$, 200 MHz), 2.35 (3H, s, CH$_3$), 5.46 (2H, s, NH$_2$), 7.06 (1H, s, CH); $^1$H (DMSO-d, 400 MHz), 2.29 (3H, s, CH$_3$), 6.96 (1H, s, CH), 7.16 (2H, s, NH$_2$); $^{13}$C-NMR (100 MHz, DMSO-d), 22.6, 115.8, 144.9, 171.8; m/z (CI+H)$^+$ 147; HRMS. found, m/z 147.00540, C$_4$H$_7$N$_2$S$_2$ (MH$^+$) requires m/z, 147.00507 (+2.4 ppm).

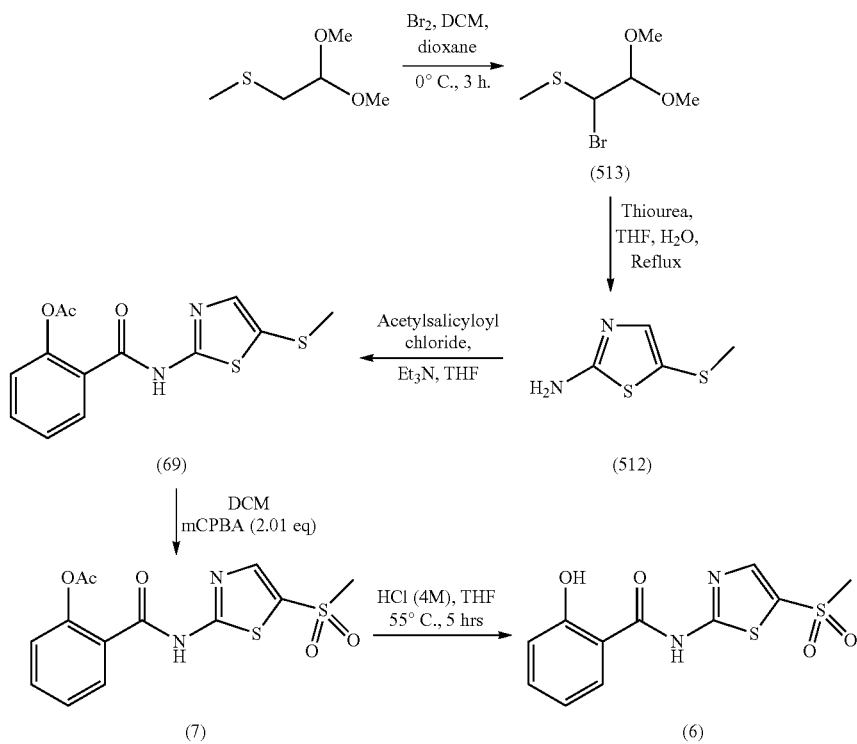

7.1 Alternate synthesis of 5-(methylthio)thiazol-2-amine (512)

7.1 Alternate synthesis of 5-(methylthio)thiazol-2-amine (512)

A solution of bromine (1.9 mL, 37.1 mmol, 1.01 eq.) and dioxane (0.1 cm$^3$, 0.3 eq.) in DCM (20 mL) was added dropwise to a stirred solution of (methylthio)acetaldehyde dimethyl acetal (5.00 g, 36.7 mmol, 1.0 eq.) in DCM (80 mL) at 0° C. over three hours. This mixture was allowed to warm to room temperature and stirred at this temperature for 30 minutes until NMR analysis revealed the disappearance of starting material. DCM was removed under vacuo. Crude bromide 513 was dissolved in THF (50 mL), which was followed by the addition of solution of thiourea (5.58 g, 2.0 eq) in THF (100 mL) and water (20 mL). The solution was refluxed overnight. Solvent was removed under vacuo and the crude product was extracted with EtOAc (50 mL) three times. The combined organic layers were washed with brine solution and

7.2 Synthesis of 2-(5-(methylthio)thiazol-2-ylcarbamoyl)phenyl acetate (69)

Under nitrogen a solution of acetylsalicyloyl chloride (1.237 g, 6.20 mmol, 1.3 eq) in THF (40 mL) was added to a stirred solution of 5-(methylthio)thiazol-2-amine ? (700.0 mg, 4.79 mmol, 1.0 eq) in dry THF (mL). This was followed by the addition of triethylamine (0.67 mL, 4.79 mmol, 1.0 eq). The reaction mixture was stirred at room temperature and monitored by TLC. After two hours, reaction was filtered through sintered funnel and solvent removed in vacuo. The crude product was dissolved in EtOAc (150 mL) and washed twice each with 1M HCl and saturated aq. sodium hydrogen carbonate solutions. The organic fraction was dried over MgSO$_4$ followed the removal of solvent. Flash column chromatography yielded the pure product 69 (1.450 g, 98%) as a solid.

Data for 69: m.p.=145-147° C.; TLC (silica gel) R$_f$=0.36 (Hex:EtOAc, 1:1); $^1$H-NMR (DMSO-d, 400 MHz), 2.23 (3H, s, CH$_3$), 2.47 (3H, s, CH$_3$), 7.28 (1H, dd, J=1.0, 8.0 Hz, ArH), 7.41 (1H, td, J=1.0, 7.6 Hz, ArH), 7.56 (1H, s, CH), 7.63 (1H, td, J=1.7, 8.0 Hz, ArH), 7.78 (1H, dd, J=1.7, 7.6 Hz, ArH), 12.70 (1H, s, NH); $^{13}$C-NMR (DMSO-d, 100 MHz), 21.1, 22.0, 123.7, 124.6, 126.2, 126.9, 130.0, 133.1, 141.6, 148.9, 160.0, 164.5, 169.2; m/z (CI) 309 (MH$^+$); HRMS. found 309.03654, $C_{13}H_{13}N_2O_3S_2$ requires 309.03677, (−0.8 ppm).

7.3 Synthesis of 2-(5-(methylsulfonyl)thiazol-2-ylcarbamoyl)phenyl acetate (7)

A solution of mCPBA (70-75%, 1.04 g, 4.2 mmol, 1.2 eq) in DCM (20 mL) was added dropwise to a stirred solution of 69 (1.1 g, 3.57 mmol, 1.0 eq) in DCM (50 mL) over a period of 30 minutes. Reaction was stirred for further 30 minutes at room temperature. A second portion of mCPBA (70-75%, 1.04 g, ~4.2 mmol, 1.18 eq) in DCM (20 mL) was added dropwise over 30 minutes. The reaction was stirred for 1 hour. The reaction was quenched with saturated aq. sodium thiosulfate solution and the organic layer was extracted two times each with aq. saturated sodium hydrogen carbonate solution and 1M HCl, respectively. The combined organic layers were washed with brine solution and dried over anhydrous MgSO$_4$. Solvent removal in vacuo and flash column chromatography (1:1 EtOAc, Hex→EtOAc) afforded 7 (1.15 g, 95%) as a white solid.

Data for 7: m.p.=173-175° C.; TLC (silica gel) R$_f$=0.27 (EtOAc); $^1$H-NMR (400 MHz, DMSO-d), 2.25 (3H, s, CH$_3$), 3.38 (3H, s, CH$_3$), 7.31 (1H, dd, J=1.0, 8.0 Hz, ArH), 7.44 (1H, td, J=1.0, 7.6 Hz, ArH), 7.67 (1H, td, J=1.6, 7.6 Hz, ArH), 7.83 (1H, dd, J=1.6, 8.0 Hz, ArH), 8.17 (1H, s, CH); $^{13}$C-NMR (100 MHz, DMSO-d), 21.1, 46.2, 123.8, 122.2, 126.3, 130.1, 130.7, 133.6, 144.6, 149.0, 163.3, 165.3, 169.2; MS m/z (CI+H)$^+$ 341, (100%), 299 (36%), 221 (83%).

7.3 Synthesis of 2-hydroxy-N-(5-(methylsulfonyl)thiazol-2-yl)benzamide (6)

A solution of 7 (1.0 g, 2.94 mmol, 1.0 eq) dissolved in THF (20 mL) was added under stirring to 2M HCl (100 mL). The reaction was refluxed for one hour and allowed to cool under stirring over one hour. The product was filtered using a sintered glass funnel, washed with distilled water and THF and dried in high vacuum to afford 834 mg (95%) of 6 as a colorless solid.

Data for 6: m.p.=282-283° C.; $^1$H-NMR (DMSO-d, 400 MHz), 3.39 (3H, s, CH$_3$SO$_2$), 7.01 (1H, t, J=7.5 Hz, ArH), 7.10 (1H, d, J=7.5 Hz, ArH), 7.52 (1H, t, J=7.5 Hz, ArH), 7.96 (1H, d, J=7.5 Hz, ArH) and 8.17 (1H, s, 4'-H); $^{13}$C-NMR (100 MHz, DMSO-d) 46.2, 117.0, 117.6, 120.1, 130.5, 130.8, 135.2, 144.2, 157.7, 163.1 and 165.6; MS (CI) m/z 299 (MH$^+$) and 316 (MNH$_4^+$); HRMS. found, m/z 299.01696, $C_{11}H_{11}N_2O_4S_2$ (MH$^+$) requires m/z, 299.01602.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A compound having a formula (I)

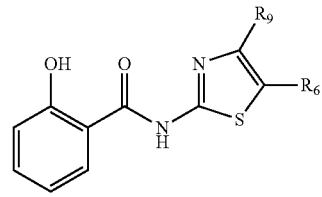

wherein one of R$_6$ or R$_9$ is C$_1$-C$_6$ alkylsulfonyl, and the other is hydrogen, or a pharmaceutically acceptable salt or ester thereof.

2. A compound according to claim 1, selected from the group consisting of structures:

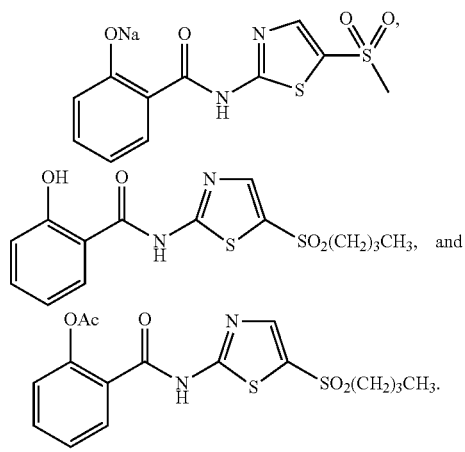

3. A compound according to claim 1, selected from the group consisting of:

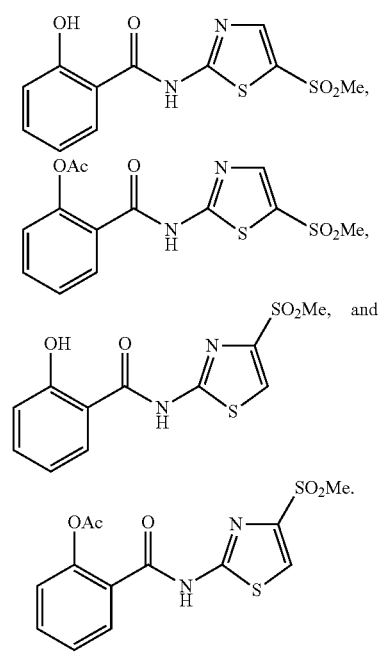

4. The compound of claim 1, wherein R$_6$ or R$_9$ is SO$_2$CH$_3$ and the other R$_6$ or R$_9$ is H.

5. The compound of claim 1, wherein the compound of formula (I) is the pharmaceutically acceptable ester.

6. The compound of claim 5, wherein the pharmaceutically acceptable ester is a $(C_1\text{-}C_6)$-acyloxy.

7. The compound of claim 1, wherein the compound is the pharmaceutically acceptable salt.

8. The compound of claim 7, wherein the pharmaceutically acceptable salt is selected from the group consisting of acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate.

9. The compound of claim 4, wherein the compound of formula (I) is the pharmaceutically acceptable ester.

10. The compound of claim 9, wherein the pharmaceutically acceptable ester is a $(C_1\text{-}C_6)$-acyloxy.

11. A pharmaceutical composition comprising a compound of claim 1 and a carrier.

12. A pharmaceutical composition comprising a compound of claim 2 and a carrier.

13. A pharmaceutical composition comprising a compound of claim 3 and a carrier.

14. A pharmaceutical composition comprising a compound of claim 4 and a carrier.

15. A pharmaceutical composition comprising a compound of claim 5 and a carrier.

16. A pharmaceutical composition comprising a compound of claim 6 and a carrier.

17. A pharmaceutical composition comprising a compound of claim 7 and a carrier.

18. A pharmaceutical composition comprising a compound of claim 8 and a carrier.

19. A pharmaceutical composition comprising a compound of claim 9 and a carrier.

20. A pharmaceutical composition comprising a compound of claim 10 and a carrier.

* * * * *